United States Patent
Charvat et al.

(10) Patent No.: US 11,884,654 B2
(45) Date of Patent: *Jan. 30, 2024

(54) SUBSTITUTED ANILINES AS CCR(4) ANTAGONISTS

(71) Applicant: CHEMOCENTRYX, INC., San Carlos, CA (US)

(72) Inventors: Trevor T. Charvat, San Jose, CA (US); Junfa Fan, Palo Alto, CA (US); Christopher W. Lange, Hayward, CA (US); Manmohan Reddy Leleti, Dublin, CA (US); Yandong Li, San Diego, CA (US); Venkat Reddy Mali, Cupertino, CA (US); Jeffrey P. McMahon, San Francisco, CA (US); Jay Powers, Pacifica, CA (US); Sreenivas Punna, Sunnyvale, CA (US); Ju Yang, Palo Alto, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/470,464

(22) Filed: Sep. 9, 2021

(65) Prior Publication Data

US 2022/0194929 A1   Jun. 23, 2022

Related U.S. Application Data

(60) Continuation of application No. 16/526,338, filed on Jul. 30, 2019, now Pat. No. 11,142,521, which is a continuation of application No. 15/674,230, filed on Aug. 10, 2017, now Pat. No. 10,407,417, which is a continuation of application No. 15/207,315, filed on Jul. 11, 2016, now Pat. No. 9,758,512, which is a division of application No. 14/452,341, filed on Aug. 5, 2014, now Pat. No. 9,567,323, which is a continuation of application No. 13/691,571, filed on Nov. 30, 2012, now Pat. No. 8,835,419.

(Continued)

(51) Int. Cl.
| | |
|---|---|
| *A01N 43/00* | (2006.01) |
| *A61K 31/00* | (2006.01) |
| *C07D 413/06* | (2006.01) |
| *C07D 401/04* | (2006.01) |
| *C07D 401/06* | (2006.01) |
| *C07D 403/06* | (2006.01) |
| *C07D 405/06* | (2006.01) |
| *C07D 417/04* | (2006.01) |
| *C07D 211/56* | (2006.01) |
| *C07D 295/135* | (2006.01) |
| *C07D 211/62* | (2006.01) |
| *C07D 211/26* | (2006.01) |
| *C07D 211/70* | (2006.01) |
| *C07D 241/04* | (2006.01) |
| *C07D 207/16* | (2006.01) |
| *C07D 211/34* | (2006.01) |
| *A61K 31/451* | (2006.01) |
| *A61K 31/454* | (2006.01) |
| *A61K 31/4545* | (2006.01) |
| *A61K 31/495* | (2006.01) |
| *A61K 31/496* | (2006.01) |
| *A61K 31/5377* | (2006.01) |

(52) U.S. Cl.
CPC .......... *C07D 413/06* (2013.01); *A61K 31/451* (2013.01); *A61K 31/454* (2013.01); *A61K 31/4545* (2013.01); *A61K 31/495* (2013.01); *A61K 31/496* (2013.01); *A61K 31/5377* (2013.01); *C07D 207/16* (2013.01); *C07D 211/26* (2013.01); *C07D 211/34* (2013.01); *C07D 211/56* (2013.01); *C07D 211/62* (2013.01); *C07D 211/70* (2013.01); *C07D 241/04* (2013.01); *C07D 295/135* (2013.01); *C07D 401/04* (2013.01); *C07D 401/06* (2013.01); *C07D 403/06* (2013.01); *C07D 405/06* (2013.01); *C07D 417/04* (2013.01)

(58) Field of Classification Search
CPC .. C07D 401/06; C07D 413/06; C07D 207/16; C07D 211/26; C07D 211/34; C07D 211/56; C07D 211/62; C07D 211/70; C07D 241/04; C07D 295/135; C07D 401/04; C07D 403/06; C07D 405/06; C07D 417/04

See application file for complete search history.

(56) References Cited

U.S. PATENT DOCUMENTS

| 8,835,419 B2 | 9/2014 | Charvat et al. |
| 9,567,323 B2 | 2/2017 | Charvat et al. |

(Continued)

FOREIGN PATENT DOCUMENTS

| JP | 2007-210887 A | 8/2007 |
| WO | 2004/010943 A2 | 2/2004 |

(Continued)

OTHER PUBLICATIONS

Wu et al, Bioorganic & Medicinal Chemistry Letters 19 (2009) 6970-6974. (Year: 2009).*
Extended European Search Report dated Apr. 25, 2022 corresponding to EP 19854176.5 filed Aug. 28, 2019; 9 pages.
Agenus Inc. Clinical Trial Identifier NCT02694822, "AGEN1884, an Anti-CTLA-4 Human Monoclonal Antibody in Subjects with Advanced o Refractory Cancer and Who Have Progressed with PD-1/PD-L1 Inhibitor as Their Most Recent Therapy," ClinicalTrials. gov (first published Mar. 1, 2016); 10 pages.

(Continued)

*Primary Examiner* — Jean P Cornet
(74) *Attorney, Agent, or Firm* — Robert Berstein

(57) ABSTRACT

Aniline compounds are provided which bind to CCR(4) and are useful for the treatment of diseases such as allergic diseases, autoimmune diseases, graft rejection and cancer.

15 Claims, 33 Drawing Sheets

Related U.S. Application Data

(60) Provisional application No. 61/565,968, filed on Dec. 1, 2011.

(56) References Cited

U.S. PATENT DOCUMENTS

| | | |
|---|---|---|
| 9,758,512 B2 | 9/2017 | Charvat et al. |
| 10,363,257 B2 | 7/2019 | Quinn et al. |
| 10,407,417 B2 | 8/2019 | Charvat et al. |
| 11,142,521 B2 | 10/2021 | Charvat et al. |
| 11,446,289 B2 | 9/2022 | Li et al. |
| 2011/0009842 A1 | 1/2011 | Minato et al. |
| 2012/0214955 A1 | 8/2012 | Ren et al. |
| 2012/0214957 A1 | 8/2012 | Li et al. |
| 2012/0226005 A1 | 9/2012 | Yao et al. |
| 2012/0232236 A1 | 9/2012 | Li et al. |
| 2014/0050660 A1 | 2/2014 | Chang et al. |
| 2018/0072740 A1 | 3/2018 | Beck et al. |
| 2019/0062440 A1 | 2/2019 | Huang et al. |
| 2020/0069673 A1 | 3/2020 | Li et al. |
| 2022/0162279 A1 | 5/2022 | Dubinett et al. |
| 2023/0097128 A1 | 3/2023 | Li et al. |

FOREIGN PATENT DOCUMENTS

| | | |
|---|---|---|
| WO | 2007/063934 A1 | 6/2007 |
| WO | 2009/037454 A2 | 3/2009 |
| WO | 2009/100140 A1 | 8/2009 |
| WO | 2012/080729 A2 | 6/2012 |
| WO | 2013/082490 A1 | 6/2013 |
| WO | 2017/194265 A1 | 11/2017 |
| WO | 2018/005374 A1 | 1/2018 |
| WO | 2018/035710 A1 | 3/2018 |
| WO | 2018/101448 A1 | 6/2018 |

OTHER PUBLICATIONS

Agenus Inc. Press Release "Agenus Reports Second Quarter 2016 Financial Results and Operational Progress," (Jul. 28, 2016); four pages.

Guzik, Katarzyna et al., "Small-Molecule Inhibitors of the Programmed Cell Death-1/Programmed Death-Ligand 1 (PD-1/PD-L1) Interaction via Transiently Induced Protein States and Dimerization of PD-L1," *J. Med. Chem.* (Jun. 14, 2017) 60:5857-5867.

NYU Langone Health, Clinical Trial Identifier NCT02868632, "Study of Immune Checkpoint Inhibition with Radiation Therapy in Unresectable, Non-metastatic Pancreatic Cancer," ClinicalTrials. gov (first published Apr. 16, 2016); 9 pages.

Zamarin, Dmitriy et al., Mogamulizumab in Combination with Durvalumab or Tremelimumab in Patients with Advanced Solid Tumors: a Phase I Study,' *Clin Cancer Res.* (Sep. 1, 2020) 26(17):4531-4541.

International Search Report and Written Opinion corresponding to PCT/US2012/067385, dated Apr. 3, 2013; 6 pages.

International Search Report dated Nov. 4, 2019 corresponding to PCT/US2019/048461 filed Aug. 28, 2019; 19 pages.

Dermer, Gerald B.; "Another Anniversary for the War on Cancer," *Bio/Technology* (Mar. 1994) 12:320.

Freshney, R. Ian; *Culture of Animal Cells, A Manual of Basic Technique;* Alan R. Liss, Inc. (© 1983, New York, NY; 4 pages.

Gura, Trisha; Systems for Identifying New Drugs are Often Faulty; *Science;* (Nov. 7, 1997); 278:1041-1042.

Solori, Roberto et al., "Targeting chemokine receptors in disease—a case study of CCR4," *European Journal of Pharmacology* (Accepted May 12, 2015); 763:169-177.

Sato, T. et al., "Internalization of CCR4 and inhibition of chemotaxis by K777, a potent and selective CCR4 antagonist," *Pharmacology* (2013; Epub Jun. 5, 2013) 91(5-6):305-313; abstract only.

Ishida, Takashi et al., "CCR4 as a novel molecular target for immunotherapy of cancer," Cancer Sci., Nov. 2006, vol. 97(11), pp. 1139-1146.

Kyowa Kirin ClinicalTrials.gov Identifier: NCT02301130; First posted Nov. 25, 2014; 8 pages.

Tanaka, Atsushi et al., "Regulatory T cells in cancer immunotherapy," *Cell Research* (2017; published online Dec. 20, 2016) 27:109-118.

Wu et al., "Cell-based optimization of novel benzamides as potential antimalarial leads," Bioorganic & Medicinal Chemistry Letters 19, 2009, pp. 6970-6974.

U.S. Appl. No. 18/302,041, filed Apr. 18, 2023, Fan et al.

\* cited by examiner

A = Br or OTf
P = protecting group

P = protecting group eq. 4 eq. 5 eq. 6 eq. 7 eq. 8 eq. 9 eq. 10

LG = leaving group eq. 11 where A = Br or OTf eq. 12 where A = Br or OTf eq. 13 where A = Br or OTf eq. 14 where A = Br or OTf (from Example 2)

(from Example 3)

(from Example 4)

(from Example 5)

(from Example 6)

(from Example 7)

(from Example 8)

(from Example 9)

(from Example 10)

(from Example 11)

(from Example 12)

(from Example 13)

(from Example 14)

(from Example 15)

(from Example 16)

(from Example 17)

(from Example 18)

FIG. 22A

Specific Examples

| # | Structure | CCR4 binding | # | Structure | CCR4 binding |
|---|---|---|---|---|---|
| 1.001 | 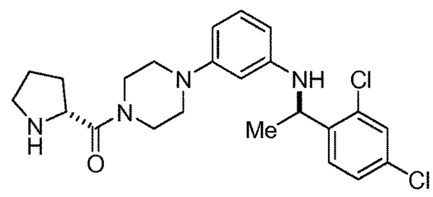 | +++ | 1.002 | 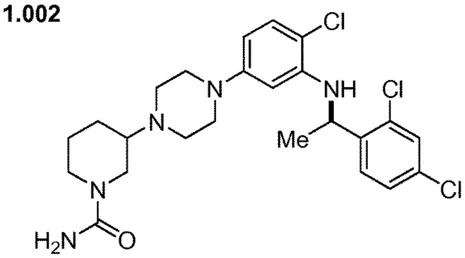 | +++ |
| 1.003 | 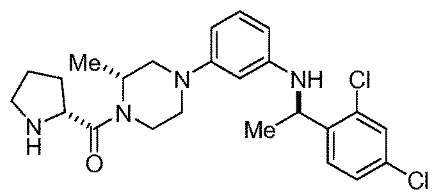 | +++ | 1.004 | 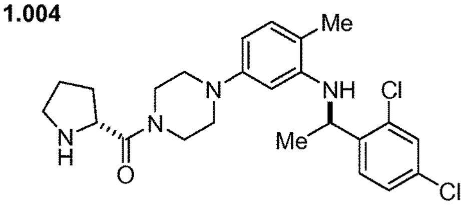 | +++ |
| 1.005 | 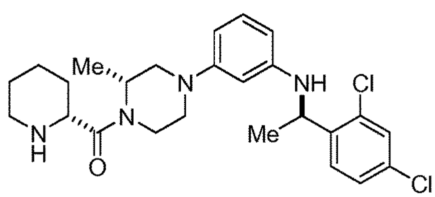 | ++ | 1.006 | 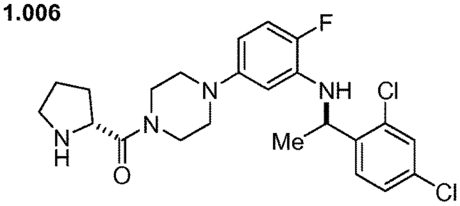 | +++ |
| 1.007 | 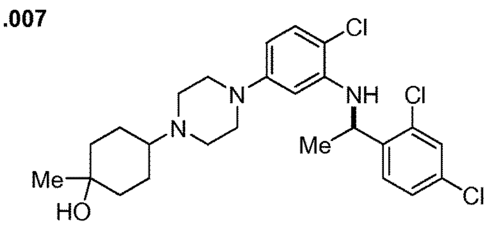 | +++ | 1.008 | 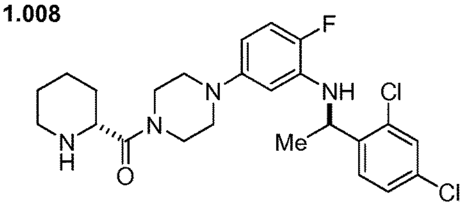 | +++ |

FIG. 22B

| # | Structure | CCR4 binding | # | Structure | CCR4 binding |
|---|---|---|---|---|---|
| 1.009 | 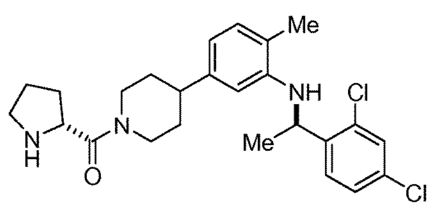 | +++ | 1.010 | 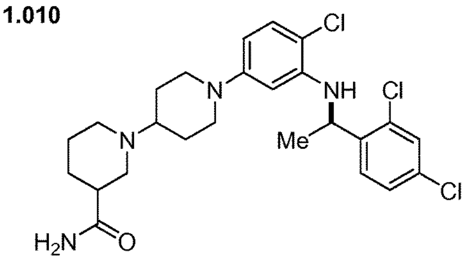 | +++ |
| 1.011 | 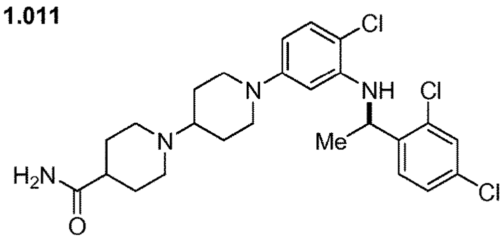 | ++ | 1.012 | 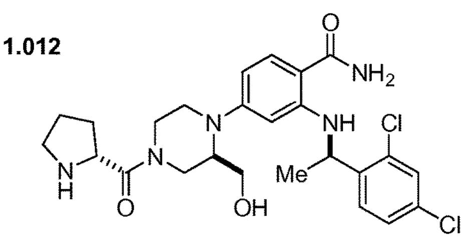 | ++ |
| 1.013 | 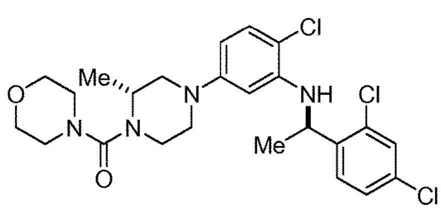 | + | 1.014 | 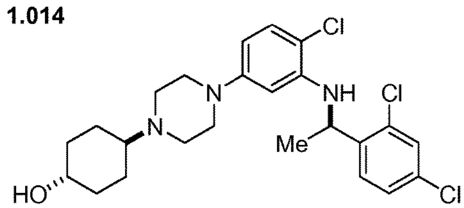 | +++ |
| 1.015 | 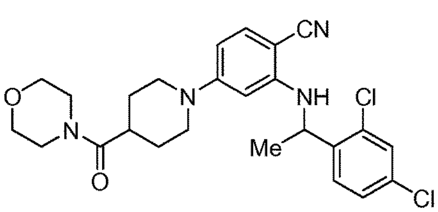 | + | 1.016 | 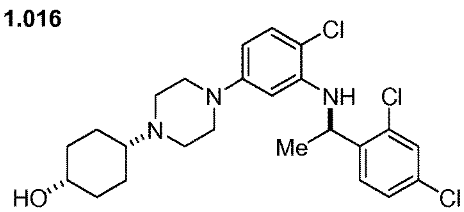 | +++ |

FIG. 22C

| # | Structure | CCR4 binding | # | Structure | CCR4 binding |
|---|---|---|---|---|---|
| 1.017 | 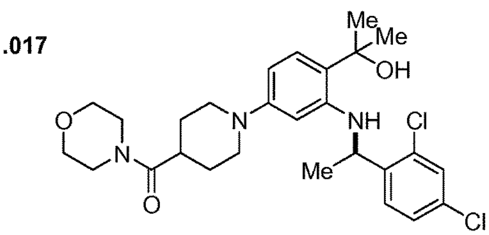 | + | 1.018 | 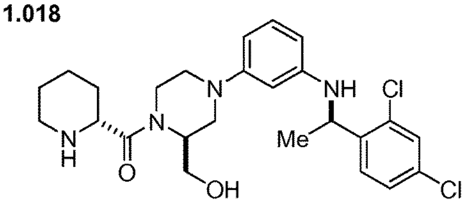 | +++ |
| 1.019 | 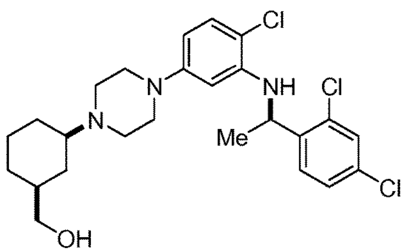 | +++ | 1.020 | 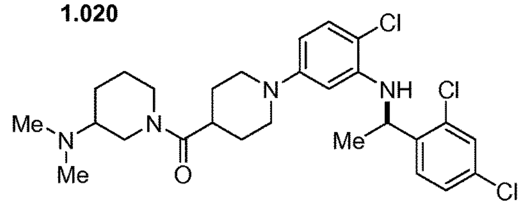 | +++ |
| 1.021 | 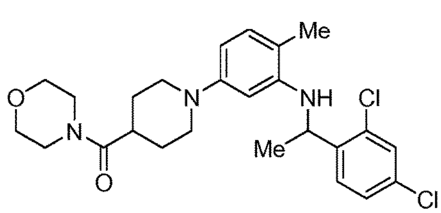 | + | 1.022 | 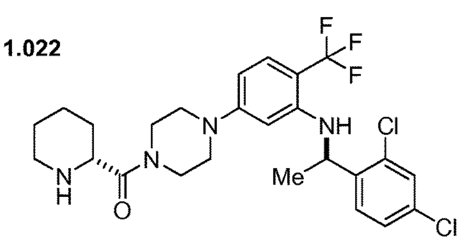 | ++ |
| 1.023 | 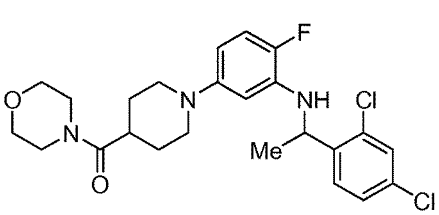 | ++ | 1.024 | 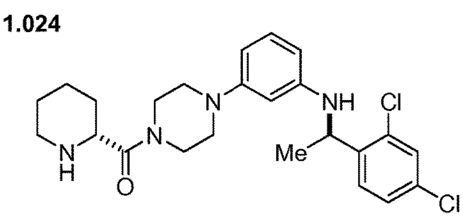 | ++ |

| # | Structure | CCR4 binding | # | Structure | CCR4 binding |
|---|---|---|---|---|---|
| 1.025 | 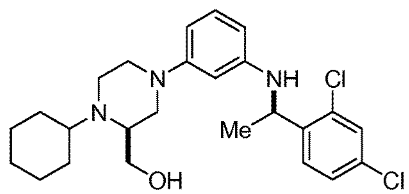 | + | 1.026 | 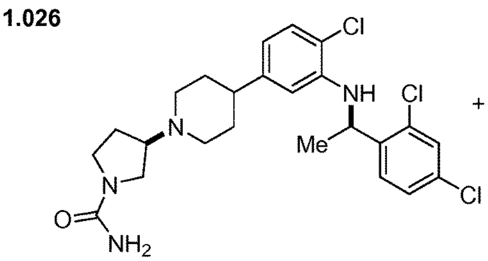 | + |
| 1.027 | 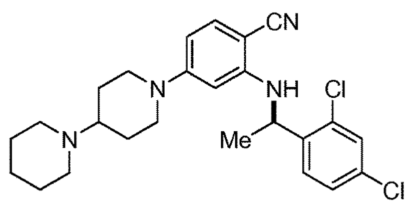 | +++ | 1.028 | 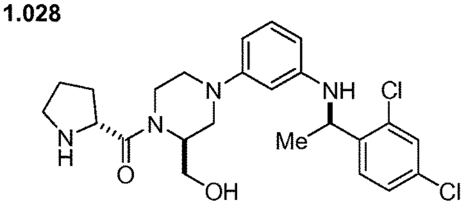 | +++ |
| 1.029 | 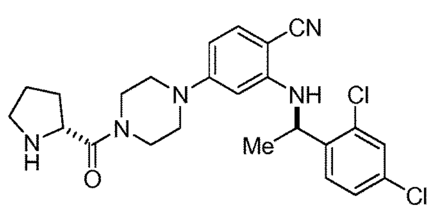 | +++ | 1.030 | 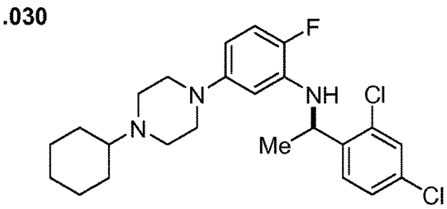 | +++ |
| 1.031 | 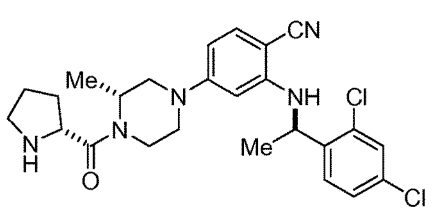 | +++ | 1.032 | 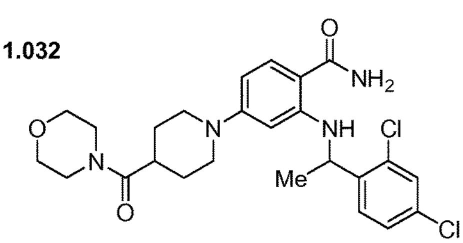 | + |

| # | Structure | CCR4 binding | # | Structure | CCR4 binding |
|---|---|---|---|---|---|
| 1.033 | 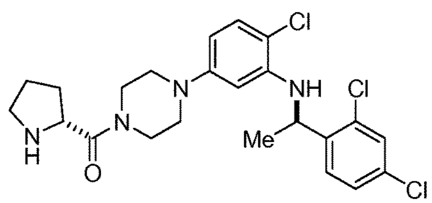 | +++ | 1.034 | 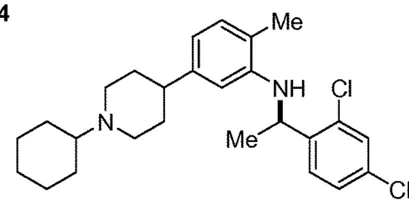 | +++ |
| 1.035 | 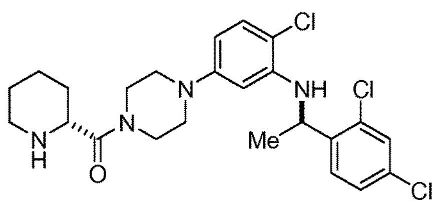 | +++ | 1.036 | 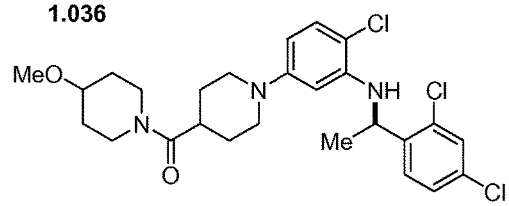 | + |
| 1.037 | 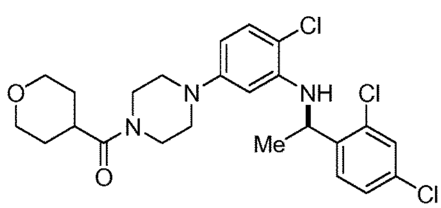 | + | 1.038 | 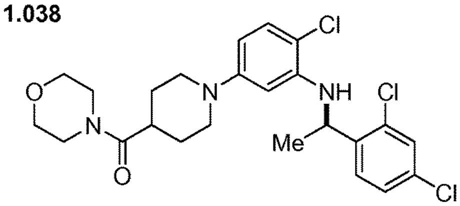 | ++ |
| 1.039 | 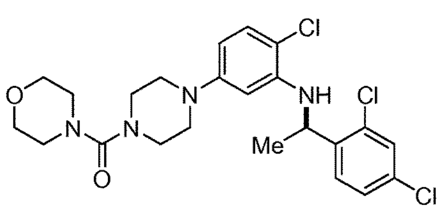 | + | 1.040 | 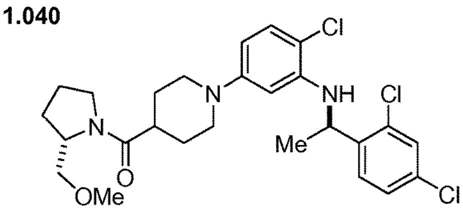 | + |

FIG. 22F

| # | Structure | CCR4 binding | # | Structure | CCR4 binding |
|---|---|---|---|---|---|
| 1.041 | 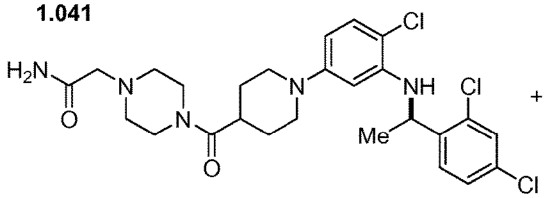 | + | 1.042 | 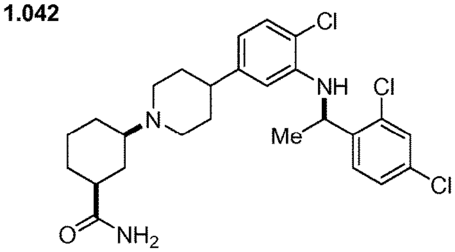 | +++ |
| 1.043 | 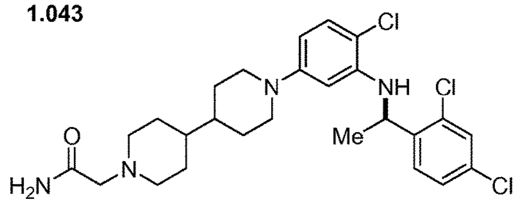 | ++ | 1.044 | 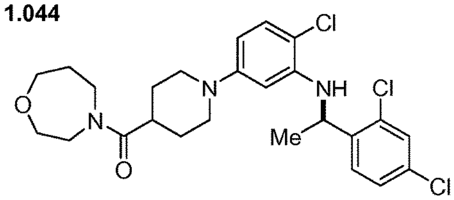 | + |
| 1.045 | 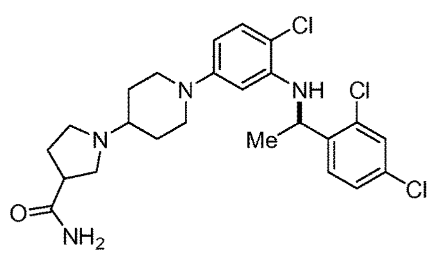 | +++ | 1.046 | 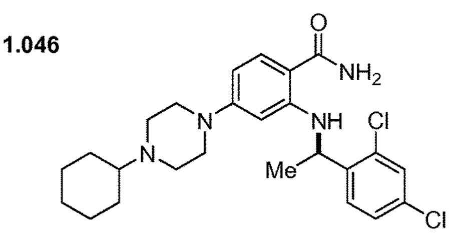 | +++ |
| 1.047 | 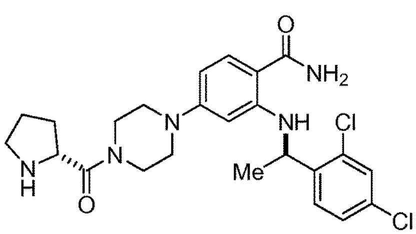 | +++ | 1.048 | 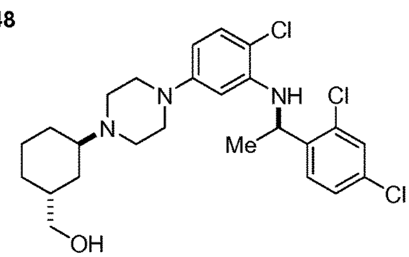 | +++ |

FIG. 22G

| # | Structure | CCR4 binding | # | Structure | CCR4 binding |
|---|---|---|---|---|---|
| 1.057 | 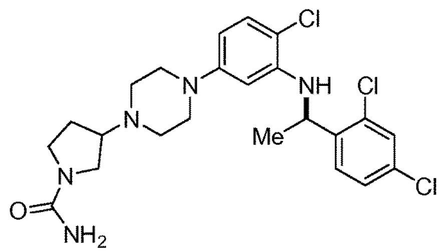 | + | 1.058 | 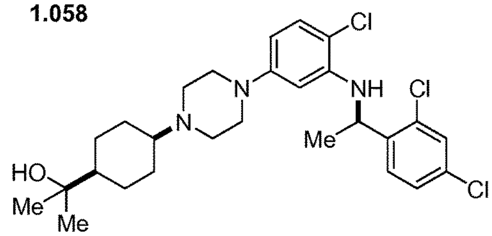 | + |
| 1.059 | 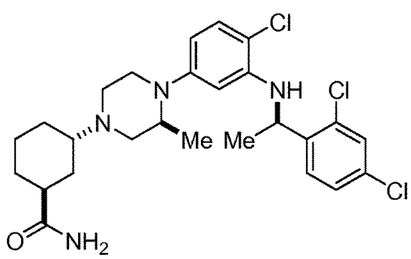 | ++ | 1.060 | 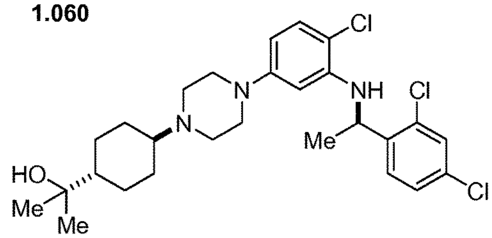 | ++ |
| 1.061 | 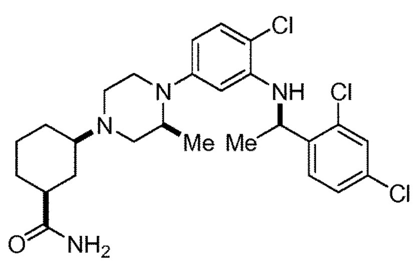 | +++ | 1.062 | 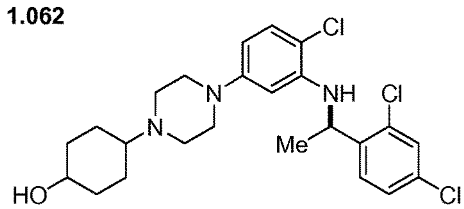 | +++ |
| 1.063 | 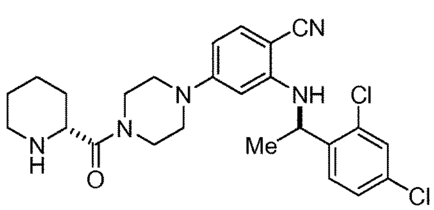 | +++ | 1.064 | 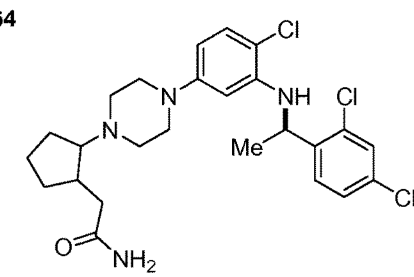 | +++ |

FIG. 22I

| # | Structure | CCR4 binding | # | Structure | CCR4 binding |
|---|---|---|---|---|---|
| 1.065 | 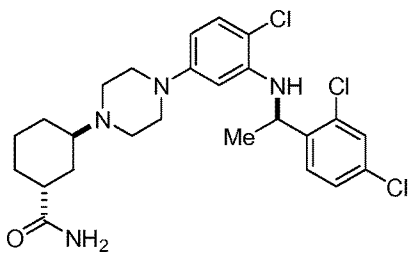 | +++ | 1.066 | 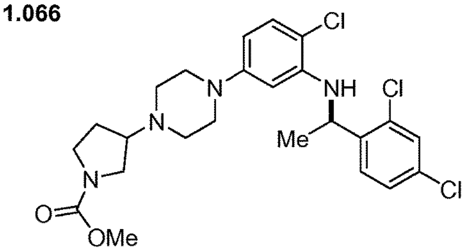 | ++ |
| 1.067 | 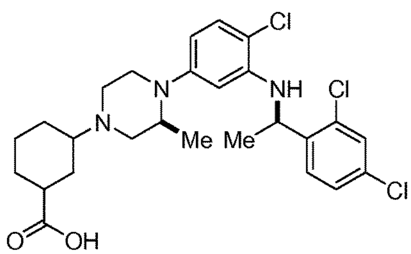 | + | 1.068 | 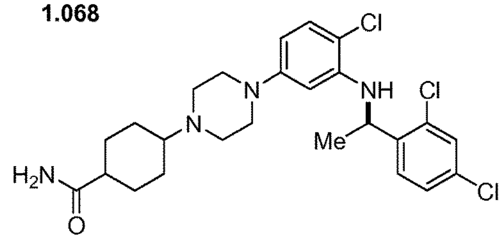 | +++ |
| 1.069 | 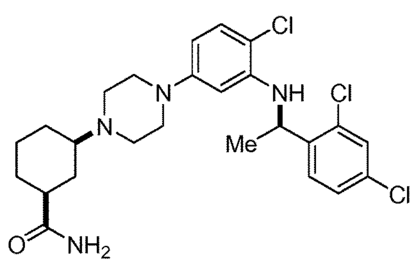 | +++ | 1.070 | 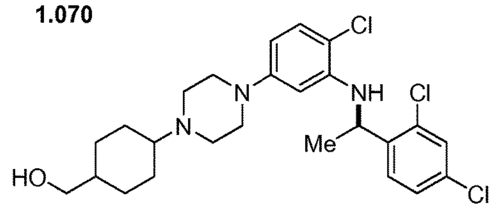 | +++ |
| 1.071 | 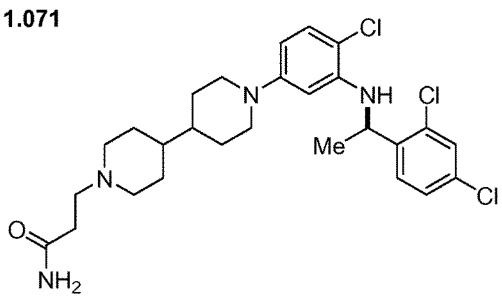 | ++ | 1.072 | 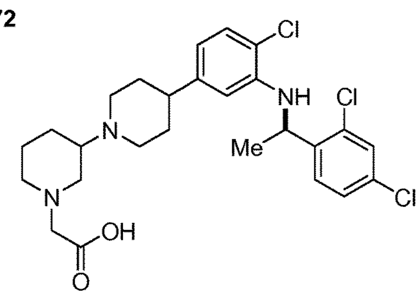 | +++ |

FIG. 22J

| # | Structure | CCR4 binding | # | Structure | CCR4 binding |
|---|---|---|---|---|---|
| 1.073 | 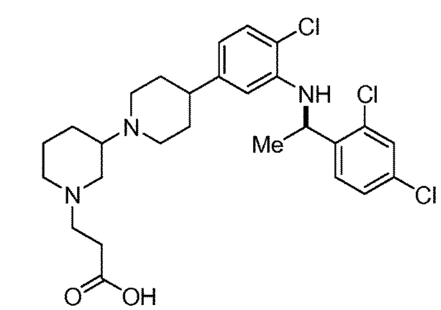 | +++ | 1.074 | 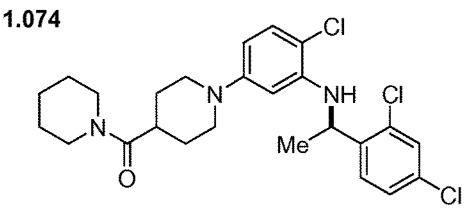 | + |
| 1.075 | 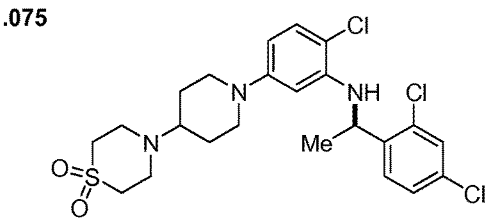 | + | 1.076 | 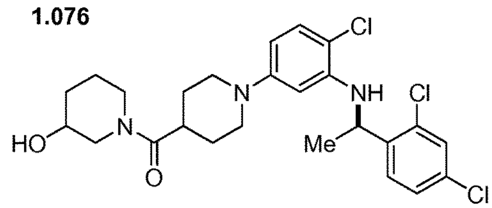 | + |
| 1.077 | 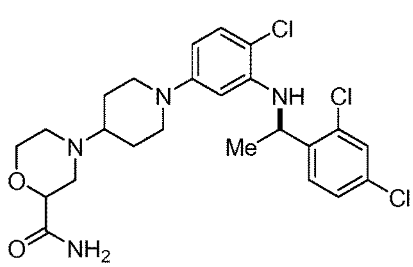 | ++ | 1.078 | 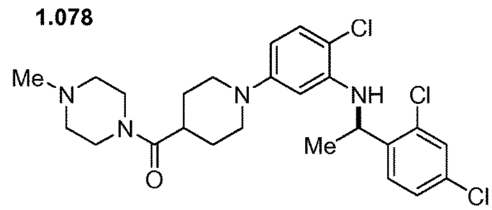 | ++ |
| 1.079 | 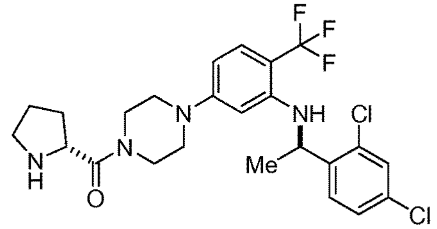 | ++ | 1.080 | 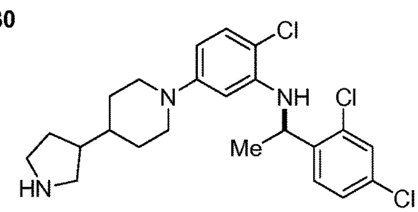 | ++ |

| # | Structure | CCR4 binding | # | Structure | CCR4 binding |
|---|---|---|---|---|---|
| 1.081 | 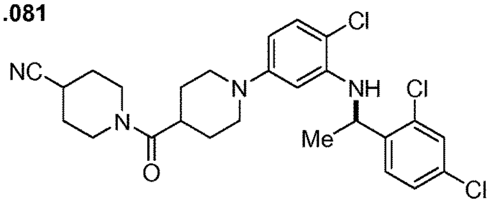 | ++ | 1.082 | 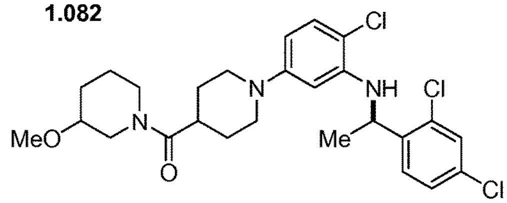 | + |
| 1.083 | 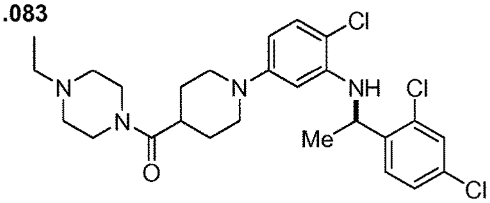 | ++ | 1.084 | 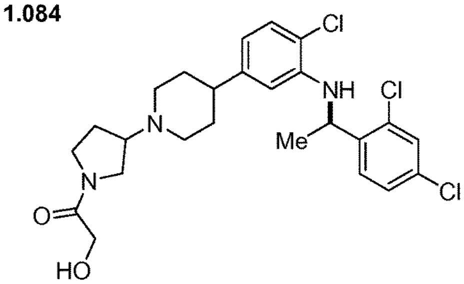 | ++ |
| 1.085 | 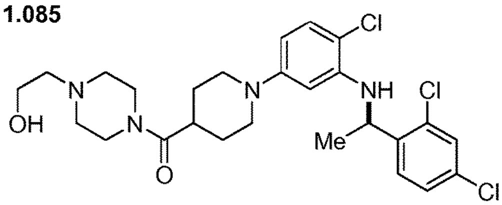 | + | 1.086 | 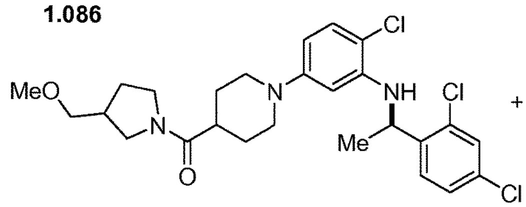 | + |
| 1.087 | 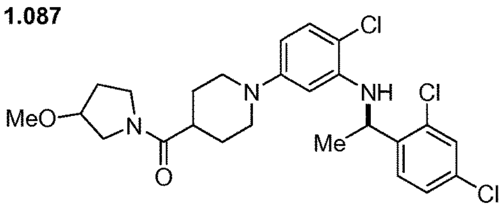 | ++ | 1.088 | 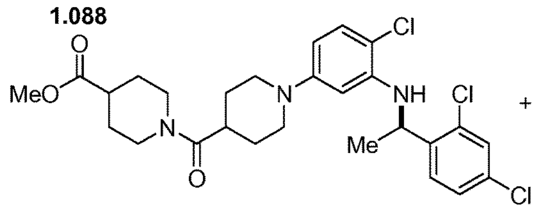 | + |

FIG. 22L

| # | Structure | CCR4 binding | # | Structure | CCR4 binding |
|---|---|---|---|---|---|
| 1.089 | 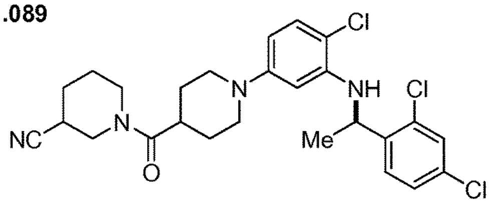 | ++ | 1.090 | 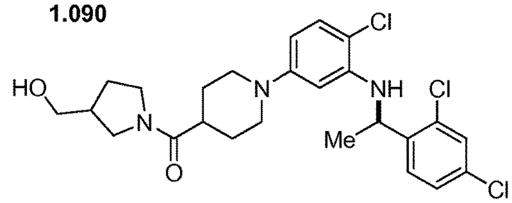 | ++ |
| 1.091 | 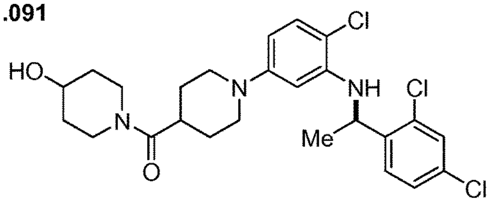 | + | 1.092 | 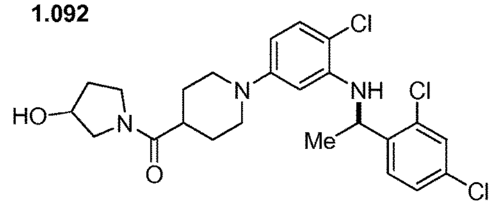 | ++ |
| 1.093 | 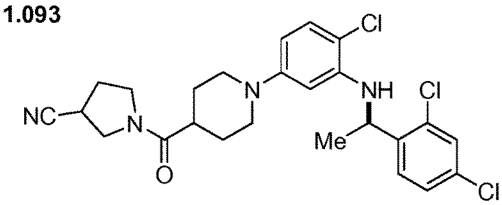 | ++ | 1.094 | 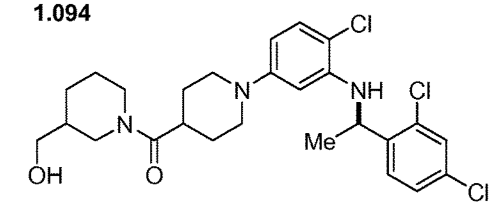 | + |
| 1.095 | 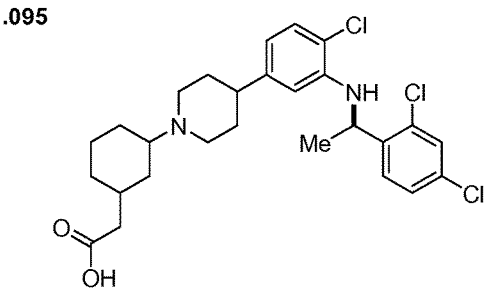 | ++ | 1.096 | 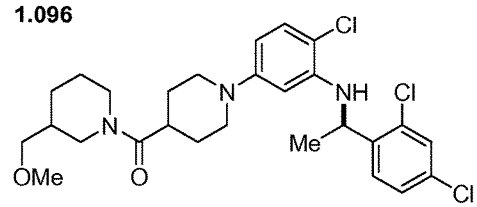 | + |

FIG. 22M

| # | Structure | CCR4 binding | # | Structure | CCR4 binding |
|---|---|---|---|---|---|
| 1.097 | 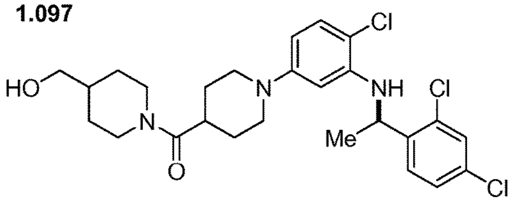 | ++ | 1.098 | 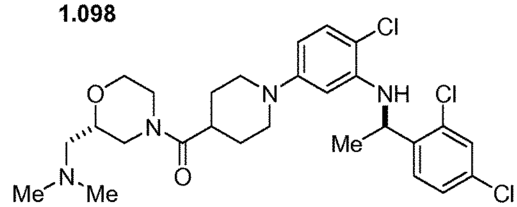 | ++ |
| 1.099 | 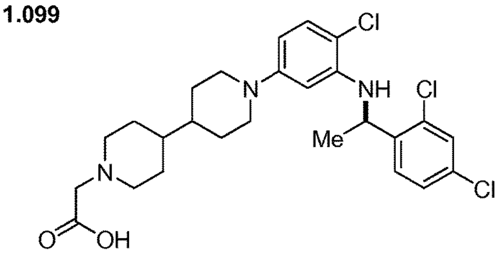 | ++ | 1.100 | 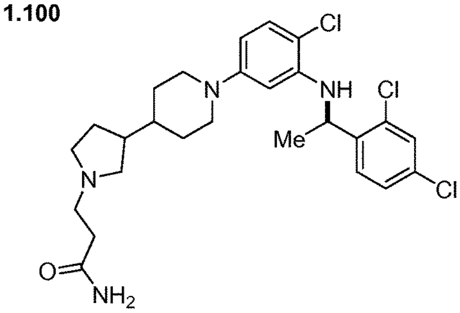 | ++ |
| 1.101 | 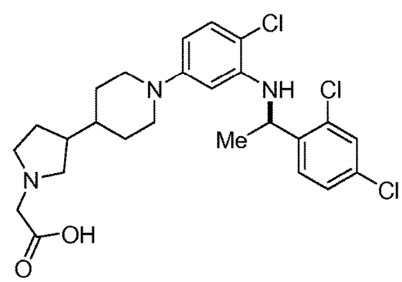 | + | 1.102 | 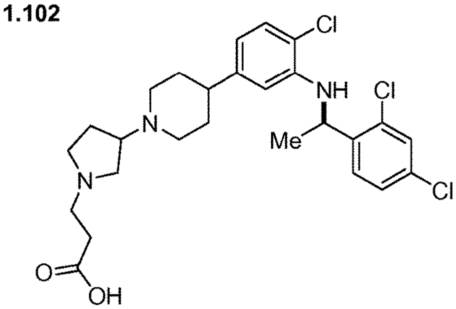 | ++ |
| 1.103 | 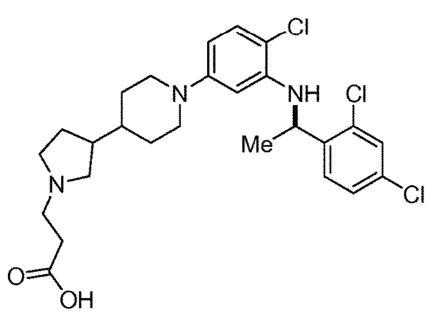 | + | 1.104 | 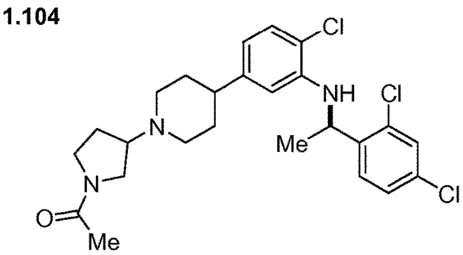 | ++ |

FIG. 22N

| # | Structure | CCR4 binding | # | Structure | CCR4 binding |
|---|---|---|---|---|---|
| 1.105 | 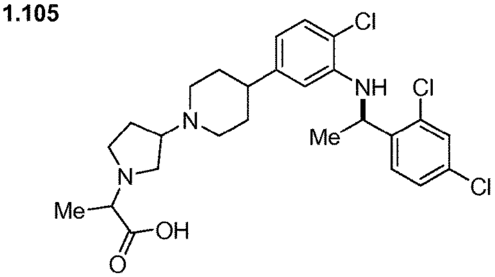 | + | 1.106 | 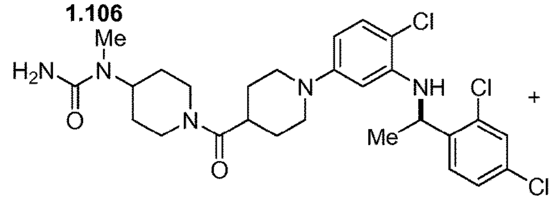 | + |
| 1.107 | 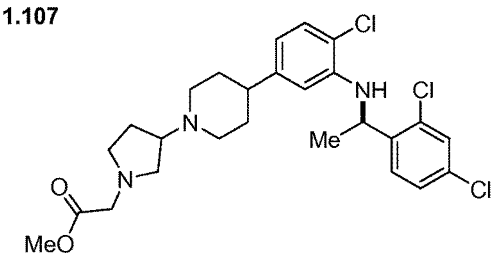 | ++ | 1.108 | 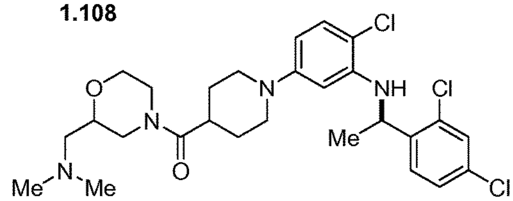 | +++ |
| 1.109 | 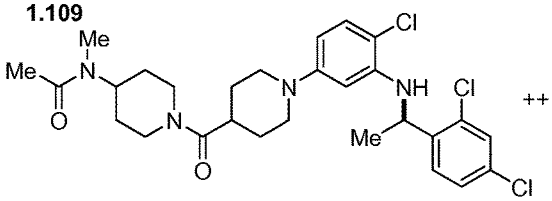 | ++ | 1.110 | 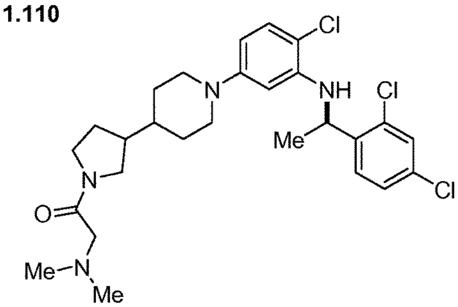 | + |
| 1.111 | 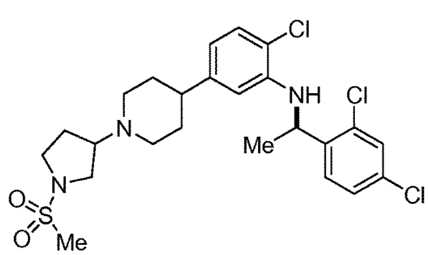 | + | 1.112 | 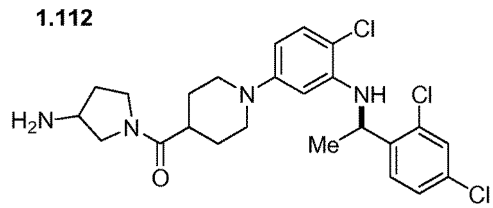 | ++ |

| # | Structure | CCR4 binding | # | Structure | CCR4 binding |
|---|---|---|---|---|---|
| 1.121 | 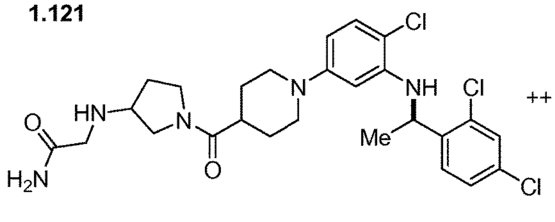 | ++ | 1.122 | 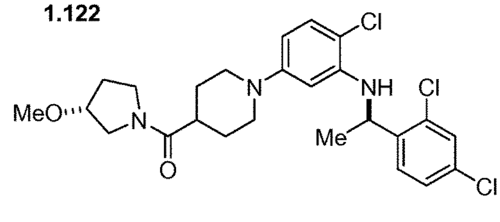 | + |
| 1.123 | 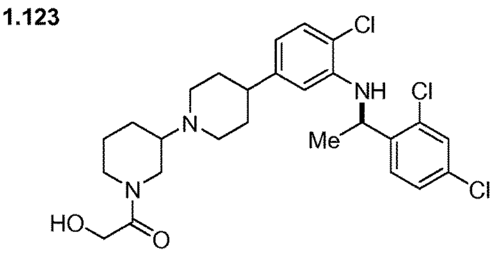 | +++ | 1.124 | 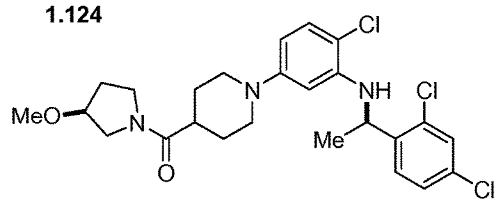 | ++ |
| 1.125 | 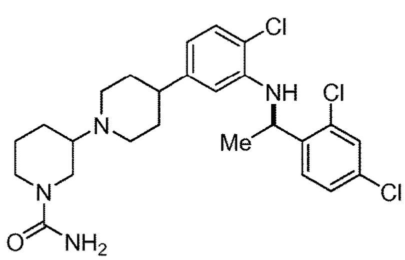 | +++ | 1.126 | 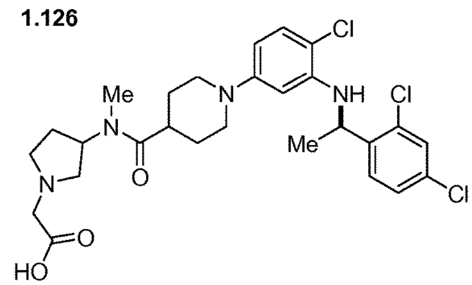 | + |
| 1.127 | 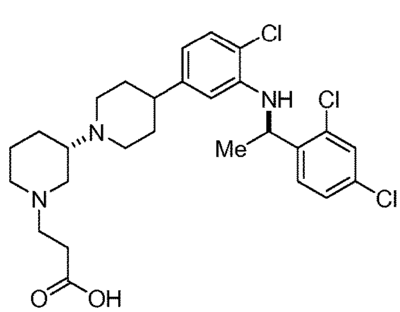 | +++ | 1.128 | 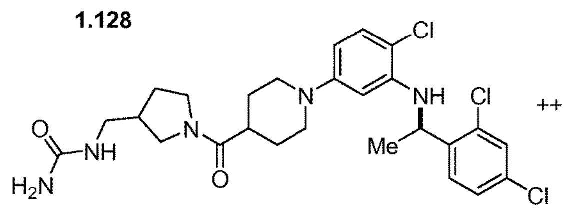 | ++ |

| # | Structure | CCR4 binding | # | Structure | CCR4 binding |
|---|---|---|---|---|---|
| 1.129 | 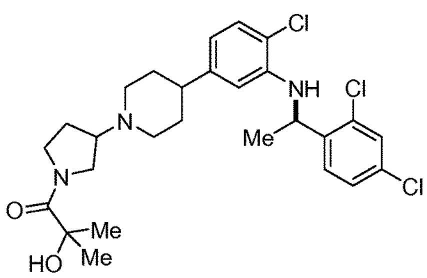 | + | 1.130 | 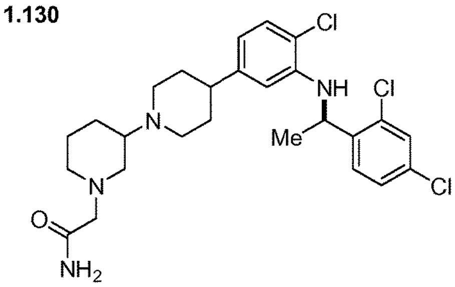 | +++ |
| 1.131 | 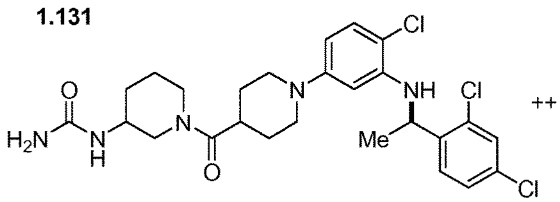 | ++ | 1.132 | 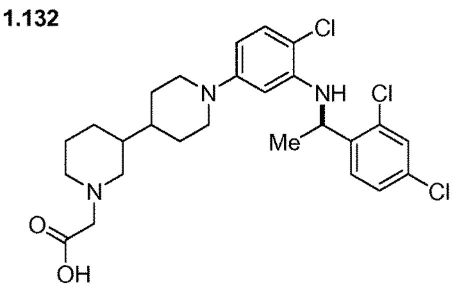 | ++ |
| 1.133 | 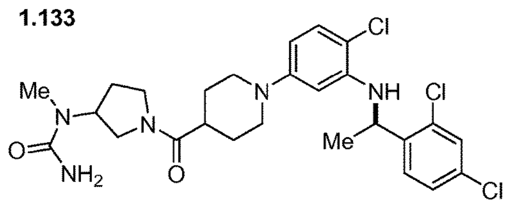 | ++ | 1.134 | 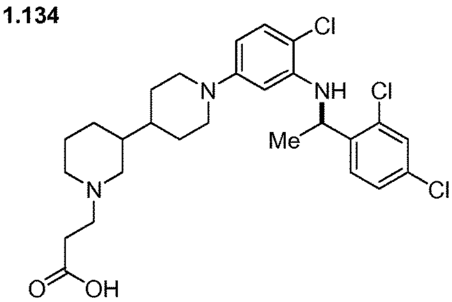 | ++ |
| 1.135 | 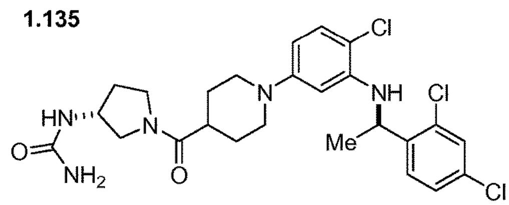 | + | 1.136 | 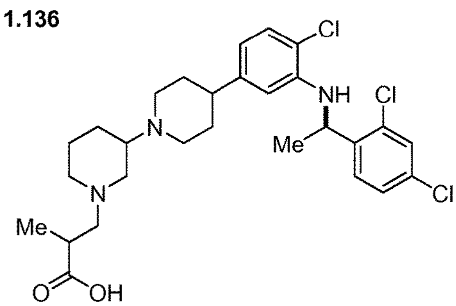 | ++ |

FIG. 22R

| # | Structure | CCR4 binding | # | Structure | CCR4 binding |
|---|---|---|---|---|---|
| 1.137 | 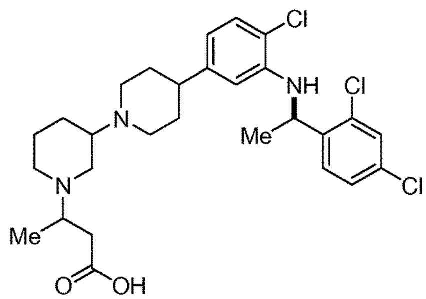 | +++ | 1.138 | 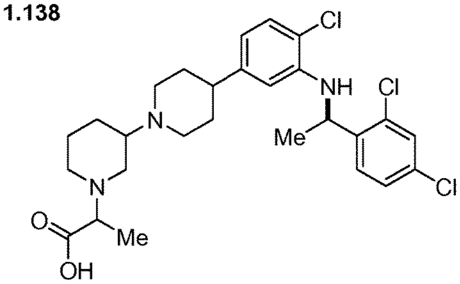 | +++ |
| 1.139 | 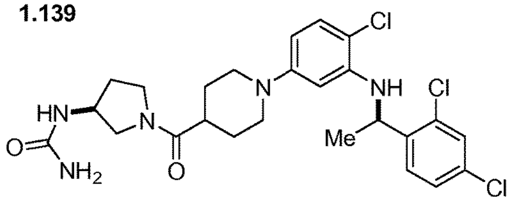 | ++ | 1.140 | 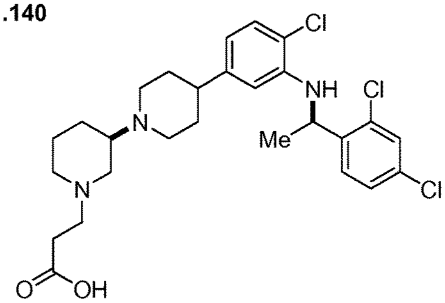 | ++ |
| 1.141 | 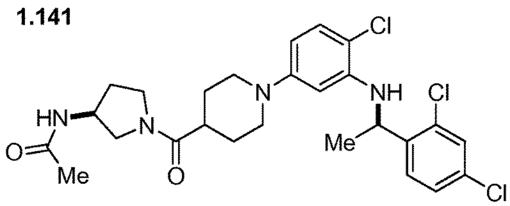 | ++ | 1.142 | 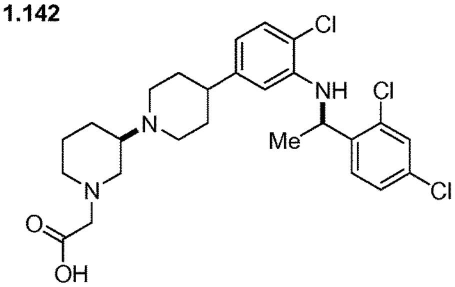 | + |
| 1.143 | 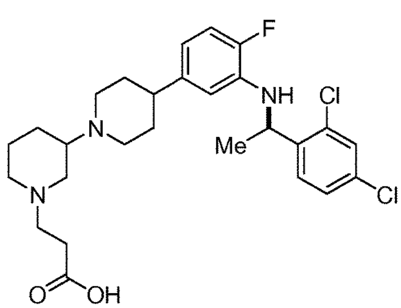 | ++ | 1.144 | 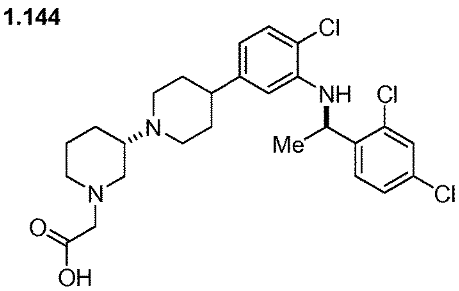 | +++ |

| # | Structure | CCR4 binding | # | Structure | CCR4 binding |

1.145 ++

SUBSTITUTED ANILINES AS CCR(4) ANTAGONISTS

CROSS-REFERENCES TO RELATED APPLICATIONS

This application is a continuation of U.S. patent application Ser. No. 16/526,338 filed Jul. 30, 2019, which is a continuation of U.S. patent application Ser. No. 15/674,230 filed Aug. 10, 2017 (now U.S. Pat. No. 10,407,417), which is a continuation of U.S. patent application Ser. No. 15/207,315 filed Jul. 11, 2016 (now U.S. Pat. No. 9,758,512), which is a divisional of U.S. patent application Ser. No. 14/452,341 filed Aug. 5, 2014 (now U.S. Pat. No. 9,567,323) which is a continuation of U.S. patent application Ser. No. 13/691,571 filed Nov. 30, 2012 (now U.S. Pat. No. 8,835,419) which application claims the benefit of priority to U.S. Provisional Application Ser. No. 61/565,968, filed Dec. 1, 2011, each of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr. Opin. Immunol.* 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ([Ca2+]), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are two main classes of chemokines, CXC (alpha) and CC (beta), depending on whether the first two cysteines are separated by a single amino acid (C—X—C) or are adjacent (C—C). The alpha-chemokines, such as interleukin-8 (IL-8), neutrophil-activating protein-2 (NAP-2) and melanoma growth stimulatory activity protein (MGSA) are chemotactic primarily for neutrophils, whereas beta-chemokines, such as RANTES, MIP-1a, MIP-1b, monocyte chemotactic protein-1 (MCP-1), MCP-2, MCP-3 and eotaxin are chemotactic for macrophages, T-cells, eosinophils and basophils (Deng, et al., *Nature*, 381:661-666 (1996)). The chemokines bind specific cell-surface receptors belonging to the family of G-protein-coupled seven-trans-membrane-domain proteins (reviewed in Horuk, *Trends Pharm. Sci.*, 15:159-165 (1994)) which are termed "chemokine receptors."

On binding their cognate ligands, chemokine receptors transduce an intracellular signal though the associated trimeric G protein, resulting in a rapid increase in intracellular calcium concentration. There are at least eleven human chemokine receptors that bind or respond to beta-chemokines and at least seven human chemokine receptors that bind to the alpha chemokines. Additionally CX3CR1 (fractalkine receptor) can bind to the fractalkine chemokine, which is distinguished by a series of three amino acids between the first two cysteines. Chemokine receptors, have been implicated as being important mediators of inflammatory and immunoregulatory disorders and diseases, including asthma and allergic diseases, as well as autoimmune pathologies such as rheumatoid arthritis and atherosclerosis.

The CC Chemokine receptor 4, CCR(4), first identified by Power et al. (Power et al. (1995) *J. Biol. Chem.* 270:19495-19500), is a G protein-coupled receptor that binds to chemokines including CCL22, also known as Macrophage-Derived Chemokine (MDC; a CC chemokine reported to be a chemoattractant for the Th2 subset of peripheral blood T cells, dendritic cells, and natural killer (NK) cells), and CCL17, also known as TARC (thymus and activation-regulated chemokine), which is also produced by monocytes and dendritic cells.

The full-length human CCR(4) protein (GenBank Accession No. X85740; SWISS-PROT Accession No. P51679) has been described, see, e.g, Imai et al. (1998) *J. Biol. Chem.* 273:1764-1768.

While the global distribution of CCR(4) is unknown, the receptor is expressed primarily in peripheral blood T lymphocytes, and is found on approximately 20% of adult peripheral blood effector/memory CD4+ T cells. CCR(4) is involved in T lymphocyte homing to the skin and lungs (see, e.g., Campbell et al. (1999) *Nature* 400:776-780, Gonzalo et al. (1999) *J. Immunol.* 163:403-5 411, Lloyd et al. (2000)*J. Exp. Med.* 191:265-273, Kawasaki et al. (2001) *J. Immunol.* 166:2055-2062) and is found on almost all T cells that have a skin homing phenotype, the CTLA+ T cells. Thus CCR(4) may be an important player in skin pathologies in which leukocytes participate. It also seems likely that CCR(4) is expressed on some other cell types, probably monocytes/macrophages and dendritic cells, among others. In view of the clinical importance of CCR(4), the identification of compounds that modulate CCR(4) function represent an attractive avenue into the development of new therapeutic agents. Such compounds and methods for their use are provided herein.

BRIEF SUMMARY OF THE INVENTION

In the present disclosure, compounds are provided having formula (I):

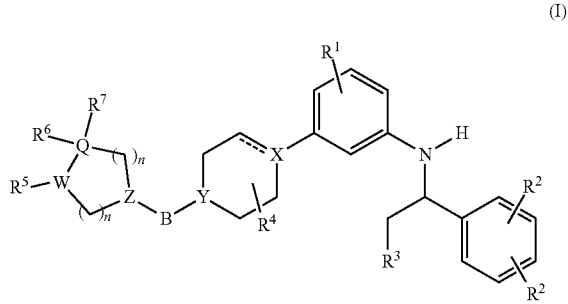

wherein the groups/letters $R^1$, $R^2$, $R^3$, $R^4$, $R^5$, $R^6$, $R^7$, $R^a$, $R^b$, B, Q, W, X, Y, Z having the meanings provided in the Detailed Description.

Compositions containing the compounds of formula (I) are provided as well as methods for treating diseases and conditions modulated by CCR(4) activity. Still further, the compounds provided herein are useful in methods of screening for additional CCR(4)-modulatory compounds.

DETAILED DESCRIPTION OF THE INVENTION

I. Abbreviation and Definitions

Figure 1:
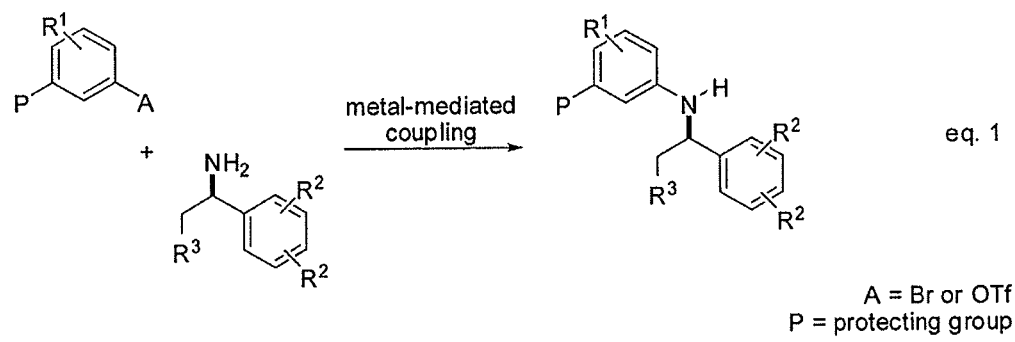
FIG. 1 provides three reaction schemes (eq. 1, eq. 2 and eq. 3) useful in construction of portions of the compounds provided herein.
Figure 1:
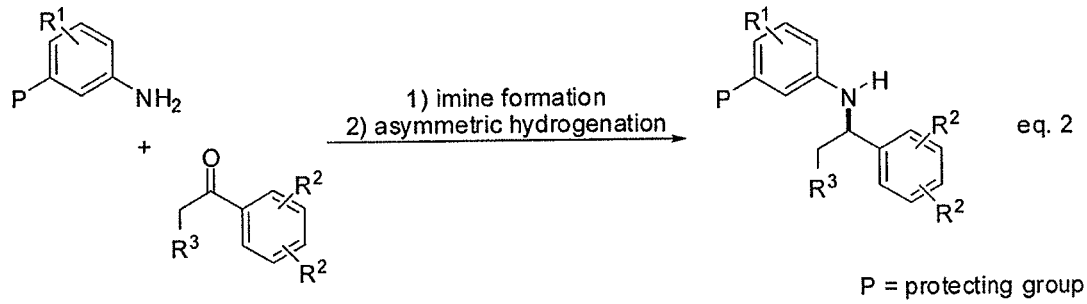
Figure 1:
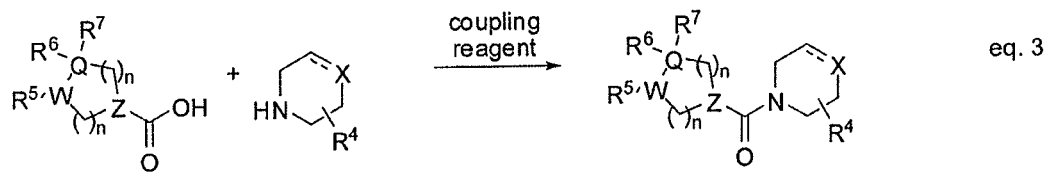
Figure 2:
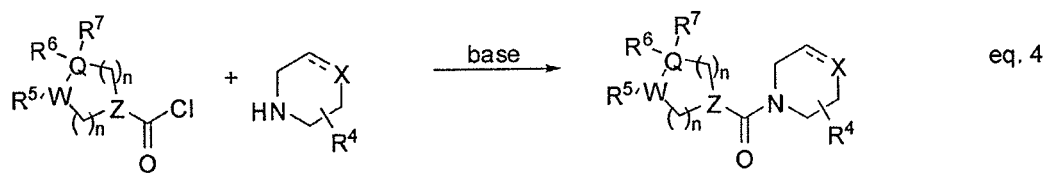
FIG. 2 provides seven reaction schemes (eq. 4, eq. 5, eq. 6, eq. 7, eq. 8, eq. 9, and eq. 10) useful in construction of portions of the compounds provided herein.
Figure 2:
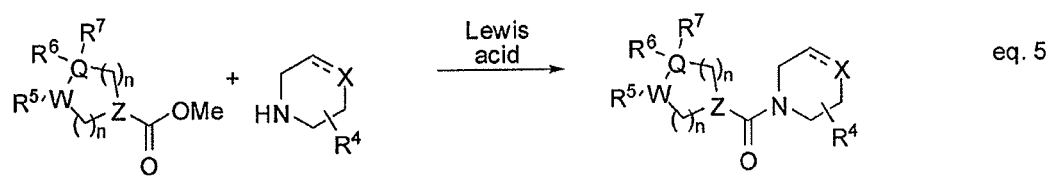
Figure 2:
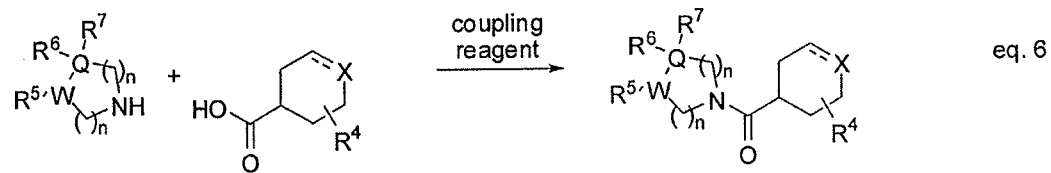
Figure 2:
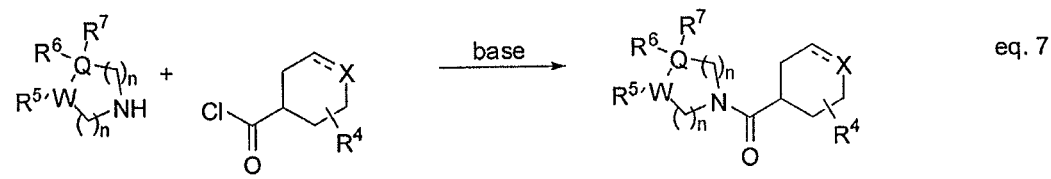
Figure 2:
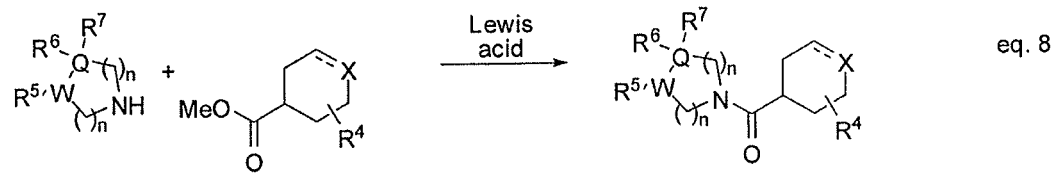
Figure 2:
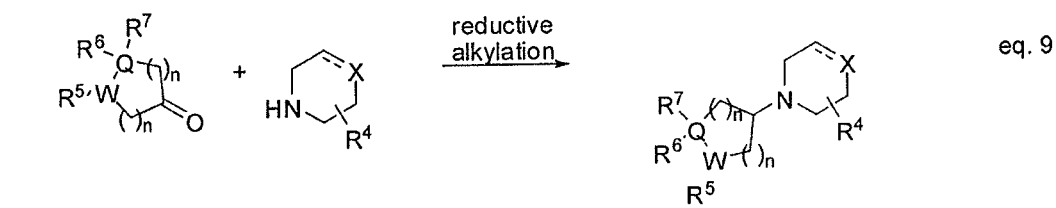
Figure 2:
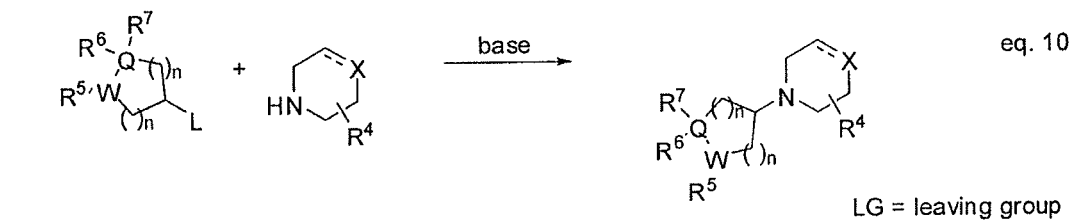
Figure 3:
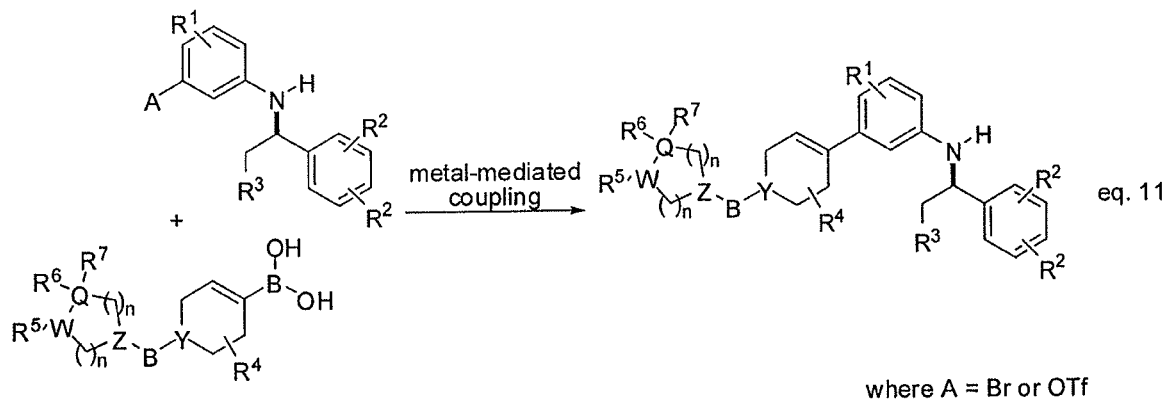
FIG. 3 provides four reaction schemes (eq. 11, eq.12, eq.13, and eq. 14) useful in construction of portions of the compounds provided herein.
Figure 3:
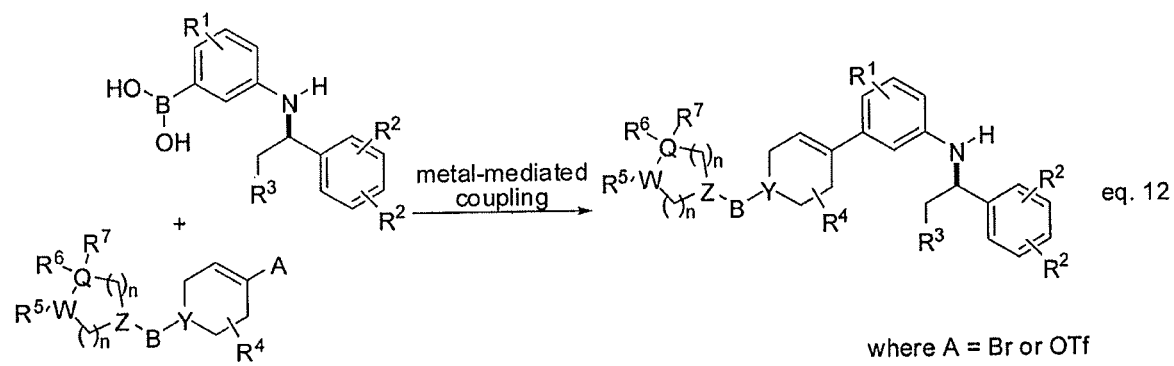
Figure 3:
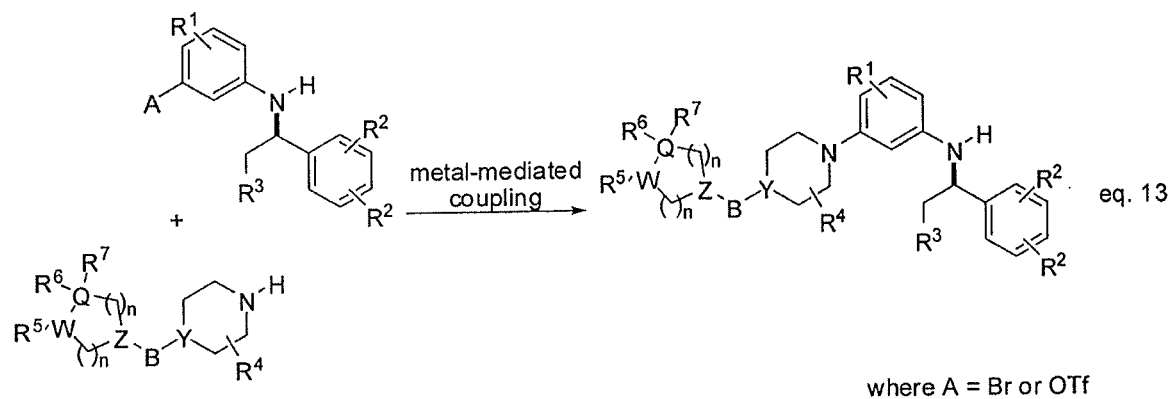
Figure 3:
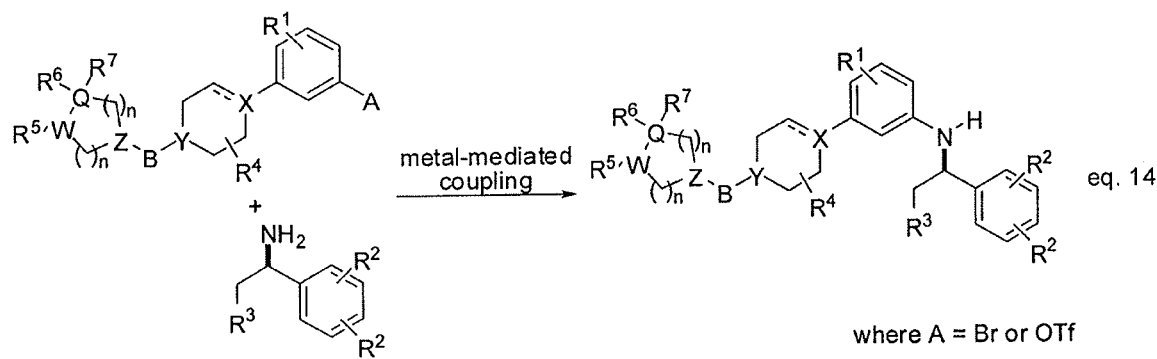
Figure 4:
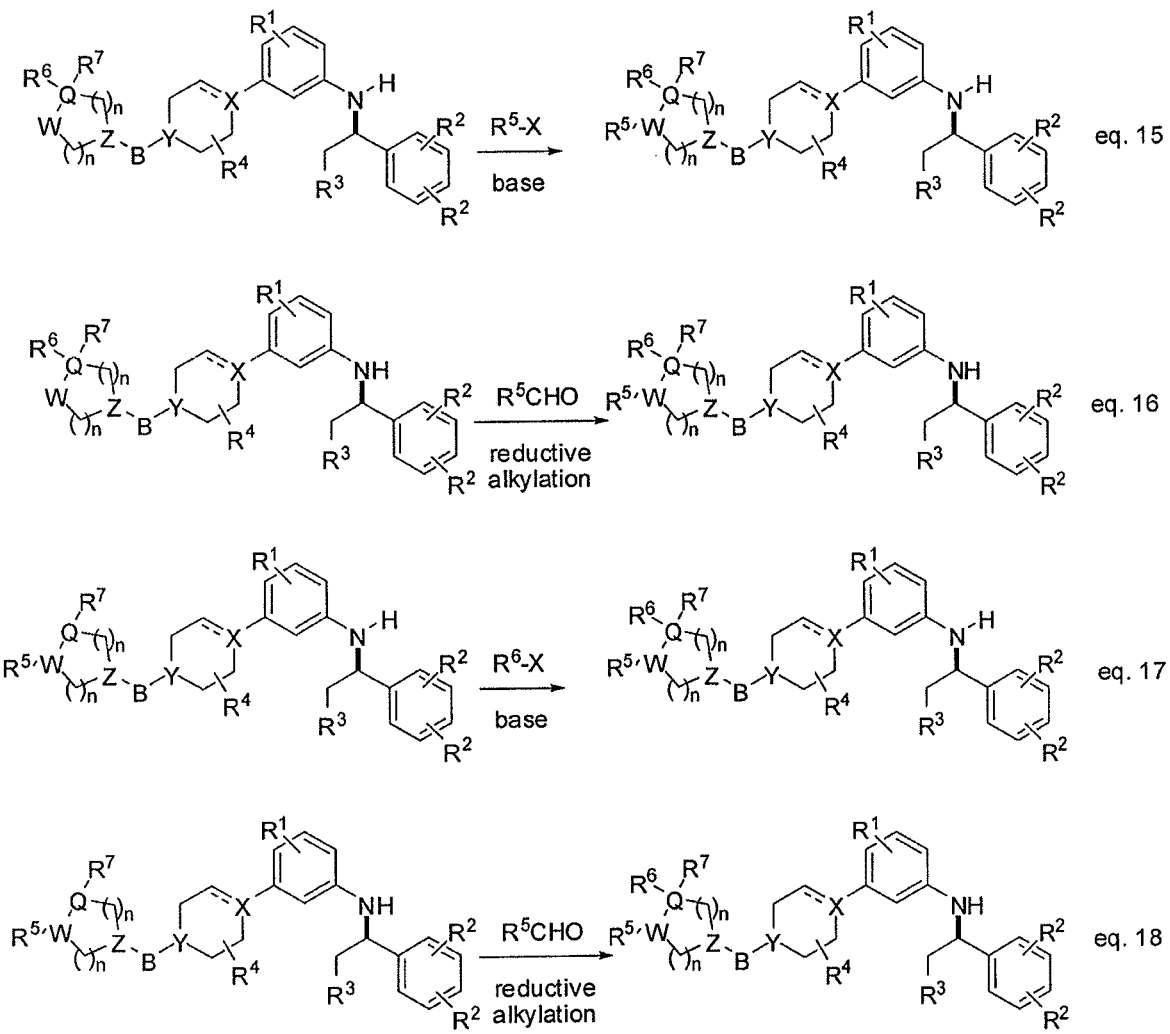
FIG. 4 provides four reaction schemes (eq. 15, eq.16, eq.17, and eq. 18) useful in construction of portions of the compounds provided herein.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "⌇", that intersects a single, double or triple bond in any chemical structure depicted herein, represent the point attachment of the single, double, or triple bond to the remainder of the molecule. A bond represented by ====== is meant to depict an optional double bond. As such, the symbol refers to either a single bond or a double bond.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "di-(C$_{1-4}$alkyl)amino-C$_{1-4}$ alkyl" refers to an amino group bearing two C$_{1-4}$ alkyl groups that can be the same or different (e.g., methyl, ethyl, propyl, isopropyl, n-butyl, sec-butyl, isobutyl and tert-butyl) and which is attached to the remainder of the molecule through a C$_{1-4}$ alkyl group (a one to four carbon alkylene linking group). Examples of di-(C$_{1-4}$ alkyl)amino-C$_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfinic acids, sulfonamides, acyl-sulfonamides, phosphonic acids, phosphinic acids, phosphoric acids, tetrazole, and oxo-oxadiazoles.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will recite both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted C$_{1-8}$ alkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, C$_{1-8}$ alkyl, C$_{1-8}$haloalkyl, C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR(4)-mediated condition or disease" and related phrases and terms refer to a condition or disease characterized by inappropriate, e.g., less than or greater than normal, CCR(4) functional activity. Inappropriate CCR(4) functional activity might arise as the result of CCR(4) expression in cells which normally do not express CCR(4), increased CCR(4) expression (leading to, e.g., inflammatory and immunoregulatory disorders and diseases) or decreased CCR(4) expression. Inappropriate CCR(4) functional activity might also arise as the result of TARC and/or MDC secretion by cells which normally do not secrete TARC and/or MDC, increased TARC and/or MDC expression (leading to, e.g., inflammatory and immunoregulatory disorders and diseases) or decreased T ARC and/or MDC expression. A CCR(4)-mediated condition or disease may be completely or partially mediated by inappropriate CCR(4) functional activity. However, a CCR(4)-mediated condition or disease is one in which modulation of CCR(4) results in some effect on the underlying condition or disease (e.g., a CCR(4) antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

II. General

Compounds of the present invention can modulate CCR (4) function and are useful in the treatment of various inflammatory and immunoregulatory disorders and diseases.

III. Embodiments of the Invention

A. Compounds

In one aspect, the present invention provides compounds having Formula I:

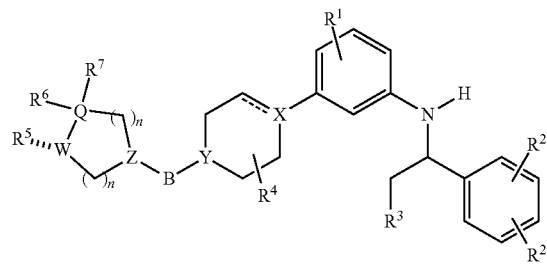

(I)

and any pharmaceutically acceptable salts thereof, wherein
$R^1$ is selected from hydrogen, $C_{1-8}$ alkyl, $C_{1-8}$ haloalkyl, $C_{1-8}$ hydroxyalkyl, $C_{3-8}$ cycloalkyl, halogen, —CN, —SO$_2$Me and —C(O)NH$_2$;
each $R^2$ is selected from $C_{1-8}$ alkyl, $C_{1-8}$ haloalkyl, halogen, —CN and $C_{1-8}$ alkoxy; or two $R^2$ groups attached to adjacent carbon atoms are optionally connected to form a 5 or 6 member ring (aliphatic or aromatic, heterocycle or not) which is optionally substituted with additional $R^2$ groups;
$R^3$ is selected from hydrogen, methyl and $C_{1-4}$ haloalkyl;
$R^4$ is selected from hydrogen, $C_{1-8}$ alkyl, $C_{1-8}$ haloalkyl and $C_{1-8}$ hydroxyalkyl;
each of the subscripts n is independently an integer from 0 to 3;
B is a bond or C(O);
Q is a selected from C, CH, N, O, S, S(O), and SO$_2$;
W, X, Y, and Z are independently selected from C, CH and N, but Q and W are not both N;
$R^5$ and $R^6$ are absent or are independently selected from H, —OH, $C_{1-8}$ alkyl, $C_{1-8}$ hydroxyalkyl, $C_{1-4}$ alkoxy-$C_{1-4}$ alkyl, —C(O)NR$^a$R$^b$, $C_{1-8}$ alkylene-C(O)NR$^a$R$^b$, —NH—$C_{1-4}$ alkylene-C(O)NR$^a$R$^b$, —C(O)—$C_{1-4}$ alkylene-NR$^a$R$^b$, —CO$_2$H and acid isosteres, $C_{1-8}$ alkylene-CO$_2$H and acid isosteres, —N(R$^a$)C(O) NR$^a$R$^b$, $C_{1-8}$ alkylene-N(R$^a$)C(O)NR$^a$R$^b$, —NR$^a$R$^b$, $C_{1-8}$ alkylene-NR$^a$R$^b$, $C_{1-8}$ alkoxy, —C(O)OR$^a$, $C_{1-8}$ alkylene-C(O)OR$^a$, —CN, —C(O)R$^a$, —SO$_2$R$^a$ and —N(R$^a$)C(O)R$^b$;

wherein
each $R^a$ and $R^b$ are independently selected from hydrogen, $C_{1-8}$ alkyl, $C_{1-8}$ hydroxyalkyl, $C_{1-8}$ haloalkyl, and $C_{1-8}$ alkoxy; and
$R^7$ is absent or is selected from H, $C_{1-8}$ alkyl and $C_{1-8}$ haloalkyl.

In one group of embodiments, the compounds provided herein are those wherein X and Y are not both N. In another group of embodiments, $R^3$ is H, and each $R^2$ is independently selected from $C_{1-8}$ alkyl, $C_{1-8}$ haloalkyl, halogen and —CN.

In another group of embodiments, the compounds provided herein have the formula (Ia):

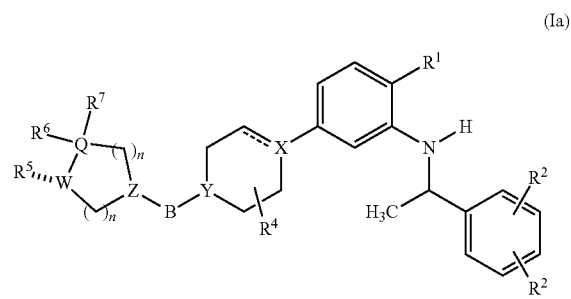

(Ia)

wherein each of $R^1$, $R^2$, $R^4$, $R^5$, $R^6$, $R^7$, X, Y, Z, W, Q, B and the subscripts n, are as described for formula I. In selected embodiments, X is C or CH.

In another group of embodiments, the compounds provided herein have the formula (Ib):

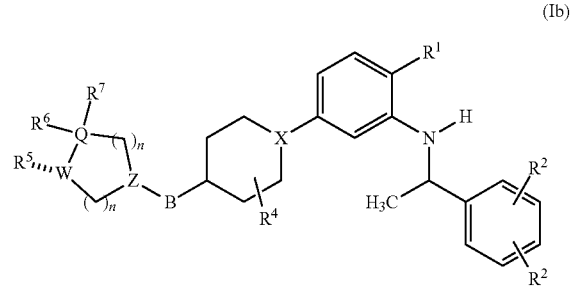

(Ib)

wherein each $R^2$ is selected from $C_{1-8}$ alkyl, $C_{1-8}$ haloalkyl, halogen and —CN, and each of $R^1$, $R^4$, $R^5$, $R^6$, $R^7$, X, Z, W, Q, B and the subscripts n, are as described for formula I.

In another group of embodiments, the compounds provided herein have the formula (Ic):

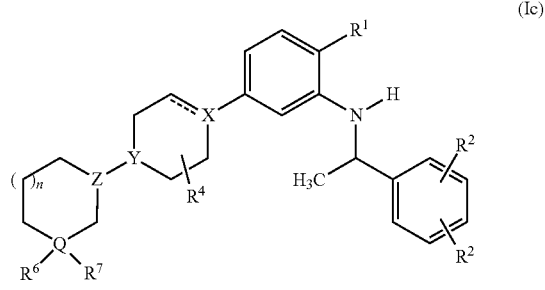

(Ic)

wherein each $R^2$ is selected from $C_{1-8}$ alkyl, $C_{1-8}$haloalkyl, halogen and —CN; the subscript n is 0 or 1; and each of $R^1$, $R^4$, $R^6$, $R^7$, X, Y, Z, and Q, are as described for formula I. In selected embodiments, n is 1, and $R^4$ is hydrogen or methyl.

In another group of embodiments, the compounds provided herein have the formula (Id):

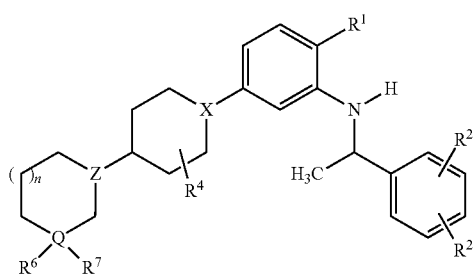

(Id)

wherein each $R^2$ is a member selected from $C_{1-8}$ alkyl, $C_{1-8}$haloalkyl, halogen and —CN; the subscript n is 0 or 1, and each of $R^1$, $R^4$, $R^6$, $R^7$, X, Z, and Q, are as described for formula I. In selected embodiments, n is 1, and $R^4$ is hydrogen or methyl.

In another group of embodiments, the compounds provided herein have the formula (Ie):

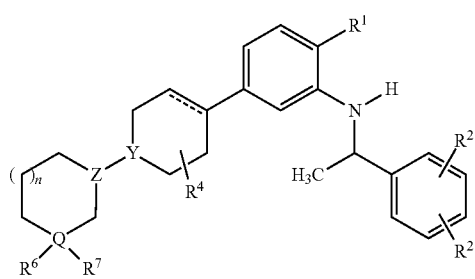

(Ie)

wherein each $R^2$ is selected from $C_{1-8}$ alkyl, $C_{1-8}$haloalkyl, halogen and —CN; the subscript n is 0 or 1; and each of $R^1$, $R^4$, $R^6$, $R^7$, Y, Z, and Q, are as described for formula I. In selected embodiments, n is 1, and $R^4$ is hydrogen or methyl.

In another group of embodiments, the compounds provided herein have the formula (If):

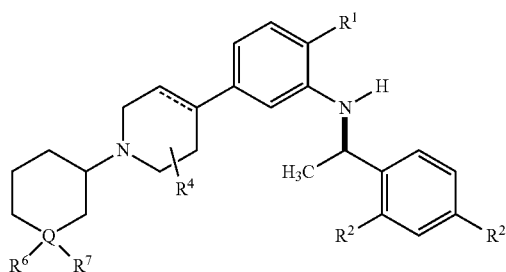

(If)

wherein each $R^2$ is selected from $C_{1-8}$ alkyl, $C_{1-8}$haloalkyl, halogen and —CN; and each of $R^1$, $R^4$, $R^6$, $R^7$, and Q, are as described for formula I. In selected embodiments, $R^4$ is hydrogen or methyl.

In still other embodiments, compounds are provided having formulae (I), (Ia), and (Ib), including specific embodiments provided above, wherein B is C(O). Still further, compounds are provided wherein the ring having Z as a ring vertex is selected from pyrrolidine and piperidine. In selected embodiments, compounds are provided wherein the ring having Z as a ring vertex is selected from pyrrolidin-2-yl and piperidin-2-yl, and at least one of $R^5$, $R^6$ and $R^7$ is other than hydrogen In yet other embodiments, compounds are provided having formulae (I), (Ia), and (Ib), including specific embodiments provided above, wherein B is a bond. In related embodiments, B is a bond and the ring having Z as a ring vertex is selected from pyrrolidine, piperidine and cyclohexane. In specific embodiments, B is a bond and the ring having Z as a ring vertex is selected from pyrrolidin-1-yl, pyrrolidin-2-yl, piperidin-1-yl, piperidin-2-yl, piperidin-3-yl and cyclohexane. In still other embodiments, B is a bond and the ring having Z as a ring vertex is selected from the group consisting of pyrrolidin-1-yl, pyrrolidin-2-yl, piperidin-1-yl, piperidin-2-yl, piperidin-3-yl and cyclohexane; and at least one of $R^5$, $R^6$ and $R^7$ is other than hydrogen.

In one group of embodiments, Z is CH or N.

In a selected group of embodiments, compounds are provided having the structures:

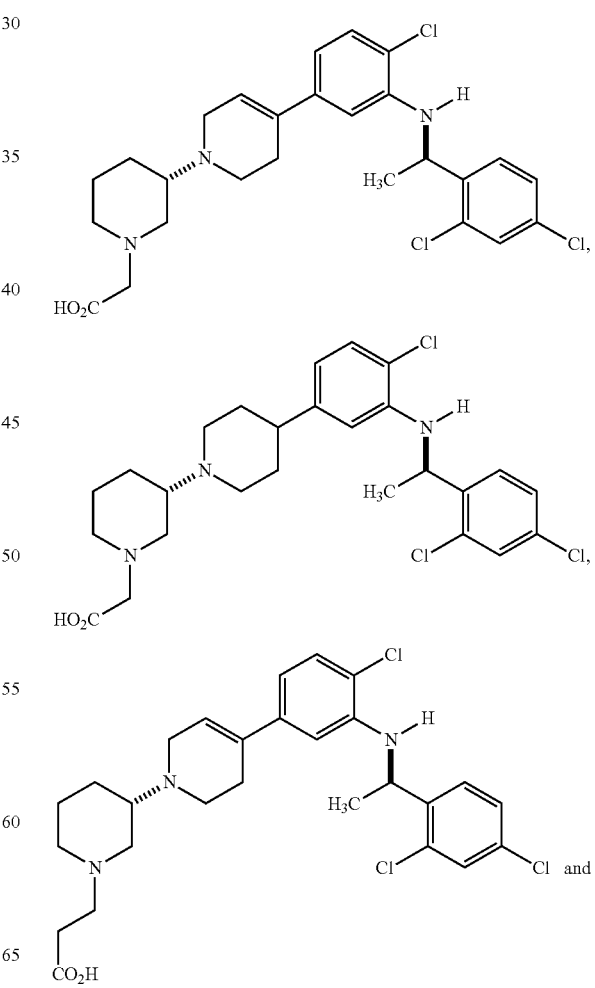

-continued

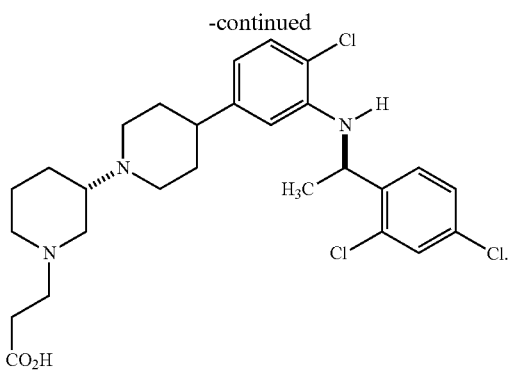

B. Compositions

In addition to the compounds provided above, compositions for modulating CCR(4) activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

C. Methods of Use

In another aspect, the present disclosure provides methods of treating or preventing a CCR(4)-mediated condition or disease by administering to a subject having such a condition or disease, a therapeutically effective amount of any compound of Formula I. Preferred compounds for use in the present methods are those compounds provided herein as preferred embodiments, as well as compounds specifically set forth in the Examples below, in the attached Figures; and provided with specific structures herein.

Diseases and conditions associated with inflammation, infection and cancer can be treated or prevented with the present compounds and compositions. In one group of embodiments, diseases or conditions, including chronic diseases, of humans or other species can be treated with inhibitors of CCR(4) function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, dermatomyositis, lichen planus, bullous pemphigoid, urticaria and pruritus, (5) vasculitis, (6) spondyloarthropathies, (7) scleroderma, (8) asthma and respiratory allergic diseases such as allergic asthma, exercise-induced asthma, allergic rhinitis, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) leukemias, lymphomas, and other blood borne cancers including cutaneous T cell lymphoma, mycosis fungoides, acute lymphoblastic leukemias and the like, and (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

In another group of embodiments, diseases or conditions can be treated with agonists of CCR(4) function. Examples of diseases to be treated with CCR(4) agonists include cancers, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Preferably, the present methods are directed to the treatment of diseases or conditions selected from allergic diseases (including skin allergies and allergic airway disorders), atopic allergic conditions including atopic dermatitis, psoriasis, cancer (including solid tumors and metastatic disease) and asthma. Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CCR(4) activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

In one group of embodiments, the compounds and compositions described herein can be combined with other compounds and compositions having related utilities to prevent and treat cancer and diseases or conditions associated with CCR(4) signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil, corticosteroids, calcineurin inhibitors, NSAIDs, inhibitors of 5-lipoxygenase, and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including psoriasis, dermatomyositis, inflammatory bowel disease, rheumatoid arthritis, osteoarthritis, psoriatic arthritis, polyarticular arthritis, multiple sclerosis, allergic diseases, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prednisolone, dexamethasone, fluticasone, hydrocortisone, budesonide, triamcinolone, salmeterol, salmeterol, salbutamol, formoterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) TNF-alpha modulators such as etanercept (Enbrel®), (k) antibody therapies such as orthoclone (OKT3), daclizumab (Zenapax®), basiliximab (Simulect®), B cell modulators such as rituximab (Rituxan®), and infliximab (Remicade®), (1) other antagonists of the chemokine receptors, especially CCR1, CCR5, CXCR2, CXCR3, CCR2, CCR3, CCR(4), CCR7, CCR9, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) T cell costimulatory modulators such as abatacept (Orencia®), (v) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IV. Examples

The following examples are offered to illustrate, but not to limit the claimed invention.

Reagents and solvents used below can be obtained from commercial sources such as Aldrich Chemical Co. (Milwaukee, Wisconsin, USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; $Pd_2dba_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

EXAMPLES

Preparation of Compounds

Those skilled in the art will recognize that there are a variety of methods available to synthesize molecules represented in the claims. In general, useful methods for synthesizing compounds represented in the claims consist of five parts, which may be done in any order: formation of the chiral amine, formation of the bicycle system, coupling between the chiral amine and the bicycle, installation of substituents at Q or W, and installation and/or modification of functional groups on the various substituents.

Several methods for the preparation of the compounds are illustrated in FIGS. 1-8 (see eq. 1-18). Equations 1-2 demonstrate methods of forming of the chiral amine. Equations 3-10 demonstrate some methods of preparing of the bicycles via amide bond formation or amine formation. Coupling of the chiral amine and the bicycle viz metal-mediated coupling are shown in equations 11-14. Equations 15-18 demonstrate methods to introduce substitution at Q or W then results in the compounds of the invention.

Examples

Example 1

Resolution of (1R)-1-(2,4-dichlorophenyl)ethanamine

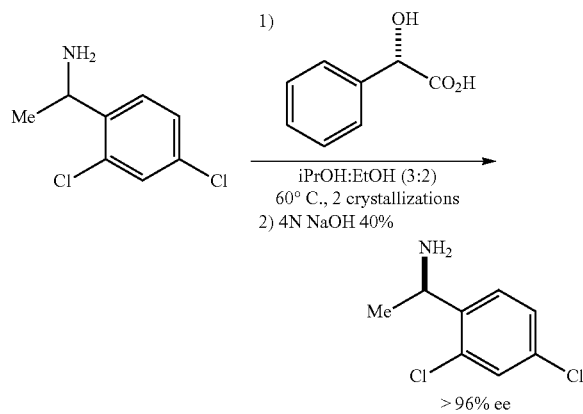

(S)-Mandelic acid (40.2 g, 264.5 mmol) was added to a solution of 3:2 isopropyl alcohol (iPrOH) and ethanol (EtOH) (500 mL) at room temperature, and the suspension was heated at 60° C. until a clear solution formed. Racemic 2,4-dichloro-α-methyl benzylamine (50 g, 264.5 mmol) was added to the hot solution, which was then cooled to 30° C. over 2 h and stirred at this temperature for 24 h. The colorless crystals were collected by filtration and washed with acetone (70 mL). The resulting salt (37.3 g, ~90% ee, determined by Mosher's method, *J. Am. Chem. Soc.,* 1973, 95, 512.) was suspended in 3:2 iPrOH/EtOH (400 mL) at room temperature and the mixture was heated at 60° C. to give a clear solution. The solution was then cooled to room temperature and stirred for 24 h. The colorless crystals were filtered off, and washed with acetone (40 mL) to give the desired salt (32.0 g, >96% ee, determined by to Mosher's method). To a portion of the salt (12.0 g) in dichloromethane ($CH_2Cl_2$) (100 mL) was added aqueous 4 N sodium hydroxide solution (30 mL). The reaction mixture was stirred for 1 h at room temperature, and extracted with dichloromethane (2×100 mL), dried with anhydrous sodium sulfate ($Na_2SO_4$), filtered, and concentrated in vacuo to afford (1R)-1-(2,4-dichlorophenyl)ethanamine as a colorless liquid (7.5 g, 39.5 mmol, 40%).

Example 2

Figure 5:
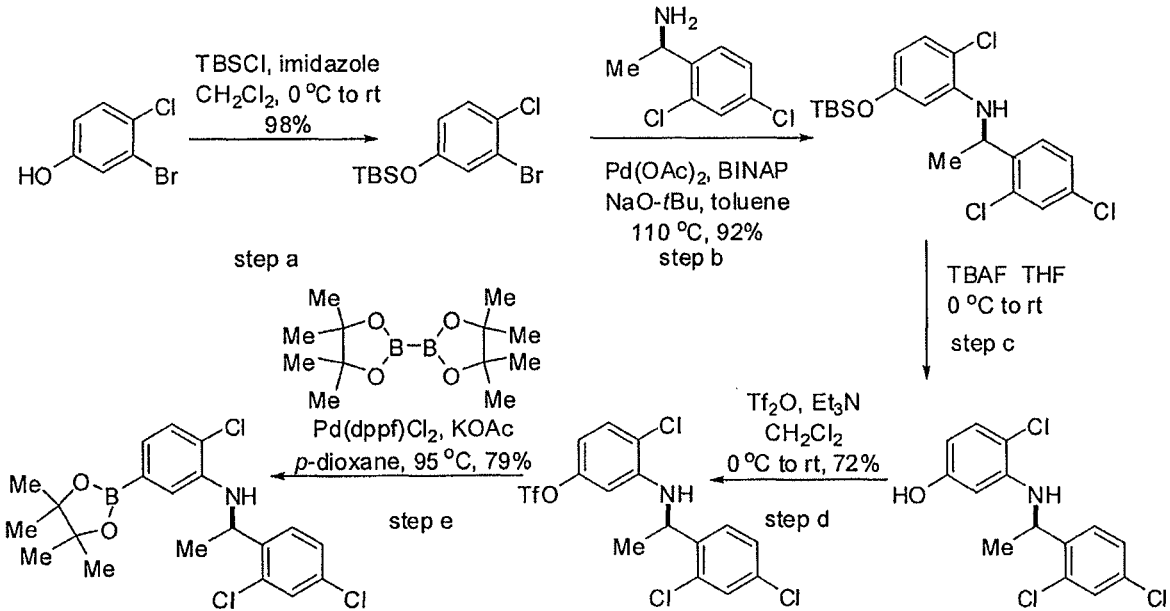
FIG. 5 provides a reaction scheme for the preparation of 2-chloro-N-((1R)-1-(2,4-dichlorophenyl)ethyl)-5-(4,4,5,5-tetramethyl-1,3,2-dioxaborolan-2-yl)aniline (see Example 2).

Synthesis of 2-chloro-N-((1R)-1-(2,4-dichlorophenyl)ethyl)-5-(4,4,5,5-tetramethyl-1,3,2-dioxaborolan-2-yl)aniline (See FIG. 5)

a) To a stirred solution of 3-bromo-4-chlorophenol (25.0 g, 120.5 mmol) in dichloromethane at 0° C. was added imidazole (9.0 g, 132.5 mmol) and t-butyldimethylchlorosilane (TBSCl) (19.0 g, 126.5 mmol). The solution was stirred at 0° C. for 30 min, then at room temperature for 14 h. The reaction mixture was diluted with deionized water, extracted with dichloromethane (2×200 mL). The combined organic layers were dried ($Na_2SO_4$), filtered, and concentrated in vacuo. The crude product was purified by flash chromatography ($SiO_2$, 0-10% ethyl acetate in hexanes) to afford (3-bromo-4-chlorophenoxy)-t-butyldimethylsilane as colorless oil (37.0 g, 115.0 mmol, 98%). MS: (ES) m/z calculated for $C_{12}H_{19}BrClOSi$ [M+H]$^+$ 321.0, found 321.

b) To a mixture of (3-bromo-4-chlorophenoxy)-t-butyldimethylsilane (15.0 g, 46.8 mmol) and (1R)-1-(2,4-dichlorophenyl)ethanamine (9.7 g, 51.5 mmol) in anhydrous toluene (250 mL) were added palladium(II) acetate ($Pd(OAc)_2$) (0.42 g, 1.9 mmol), 2,2'-bis(diphenylphosphino)-1,1'-binaphthyl (BINAP) (1.74 g, 2.80 mmol), and sodium t-butoxide (NaO-tBu) (6.3 g, 65.52 mmol). The resulting mixture was heated at 110° C. under nitrogen for 3 h. After cooling to room temperature, the suspension was filtered through a plug of Celite, and washed with ethyl acetate (EtOAc) (100 mL). The filtrate was concentrated in vacuo. The resulting residue was diluted with deionized water, and extracted with ethyl acetate (500 mL). The organic layer was washed with brine, dried ($Na_2SO_4$), and concentrated in vacuo. The crude residue was purified by flash chromatography ($SiO_2$, 0-15% ethyl acetate in hexanes) to afford (R)-5-(t-butyldimethylsilyloxy)-2-chloro-N-(1-(2,4-dichlorophenyl)ethyl)aniline as a viscous oil (18.5 g, 42.9 mmol, 92%). $^1$H NMR (400 MHz, CDCl$_3$) δ 7.42 (d, J=1.6 Hz, 1H), 7.32 (d, J=8.8 Hz, 1H), 7.19 (dd, J=1.6, 8.4 Hz, 1H), 7.08 (d, J=8.4 Hz, 1H), 6.13 (dd, J=2.2, 8.4 Hz, 1H), 5.71 (d, J=2.4 Hz, 1H), 4.87-4.84 (m, 1H), 4.67 (d, J=4.8 Hz, 1H), 1.58 (d, J=6.8 Hz, 3H), 0.98 (s, 9H), 0.02 (s, 3H), 0.01 (s, 3H).

c) To a stirred solution of (R)-5-(t-butyldimethylsilyloxy)-2-chloro-N-(1-(2,4-dichlorophenyl)ethyl)aniline (18.5 g, 43.0 mmol) in anhydrous tetrahydrofuran (THF) (100 mL) at 0° C. was added a solution of tetrabutylammonium fluoride (TBAF) (1 M solution in THF, 43.0 mL, 43.0 mmol). The reaction mixture was stirred at 0° C. for 30 min, and then warmed to room temperature and stirred for an additional 4 h. The reaction mixture was diluted with deionized water and extracted with ethyl acetate (2×50 mL). The combined organic layers were washed with deionized water, brine, dried (Na$_2$SO$_4$), filtered, and concentrated in vacuo to give (R)-4-chloro-3-(1-(2,4-dichlorophenyl)ethylamino)phenol as a brown solid (15.3 g). The solid compound was carried to the next step without further purification.

d) To a stirred solution of the (R)-4-chloro-3-(1-(2,4-dichlorophenyl)ethylamino)phenol (18.0 g, 56.9 mmol) in dichloromethane (150 mL) at 0° C. was added triethylamine (Et$_3$N) (9.6 g, 91.0 mmol) and trifluoromethanesulfonic anhydride (TFA) (17.6 g, 62.6 mmol). The reaction mixture was stirred at 0° C. for 2 h, then warm to room temperature and stirred for 10 min. The solution was diluted with deionized water, extracted with dichloromethane (2×50 mL). The combined organic layers were washed with brine, dried (Na$_2$SO$_4$), filtered, and concentrated in vacuo. The crude product was purified by flash chromatography (SiO$_2$, 0-25% ethyl acetate in hexanes) to afford (R)-4-chloro-3-(1-(2,4-dichlorophenyl)ethylamino)phenyl trifluoromethanesulfonate as viscous oil (17.8 g, 39.7 mmol, 72%). $^1$H NMR (400 MHz, CDCl$_3$) δ 7.40 (d, J=2.0 Hz, 1H), 7.25-7.23 (m, 2H), 7.16 (dd, J=1.6, 8.4 Hz, 1H), 6.49 (dd, J=2.8, 8.8 Hz, 1H), 6.05 (d, J=3.2, Hz, 1H), 4.91-4.89 (m, 1H), 4.88-4.83 (m, 1H), 1.58 (d, J=6.8 Hz, 3H).

e) A mixture of (R)-4-chloro-3-(1-(2,4-dichlorophenyl)ethylamino)phenyl trifluoromethanesulfonate (6.0 g, 13.3 mmol), bis(pinacolato)diboron (4.08 g, 15.9 mmol), [1,1'-bis(diphenylphosphino)ferrocene]dichloropalladium(II) (Pd(dppf)Cl$_2$) (0.39 g, 0.53 mmol), and potassium acetate (3.93 g, 39.9 mmol) in p-dioxane (100 mL) was purged with nitrogen for 5 min, and then heated at 95° C. for 4 h. After cooling to room temperature, the mixture was filtered and washed with EtOAc (50 mL). The filtrate was concentrated in vacuo. The resulting crude mixture was diluted with ethyl acetate (200 mL), washed with deionized water, brine, dried (Na$_2$SO$_4$), and concentrated in vacuo. The resulting crude was purified by flash chromatography (SiO$_2$, 0-15% ethyl acetate in hexanes) to afford the title compound as a white solid (4.5 g, 10.5 mmol, 79%). $^1$H NMR (400 MHz, CDCl$_3$) δ 7.35 (d, J=6.0 Hz, 1H), 7.27 (d, J=8.4 Hz, 1H), 7.22 (d, J=5.2 Hz, 1H), 7.12 (dd, J=2.0, 8.4 Hz, 1H), 6.98 (dd, J=0.8, 7.6 Hz, 1H), 6.77 (s, 1H), 5.03-4.98 (m, 1H), 4.66 (d, J=6.4 Hz, 1H), 1.52 (d, J=6.8 Hz, 3H), 1.27 (s, 6H), 1.25 (s, 6H); MS: (ES) m/z calculated for C$_{20}$H$_{24}$BCl$_3$NO$_2$ [M+H]$^+$ 426.1, found 426.

Example 3

Figure 6:
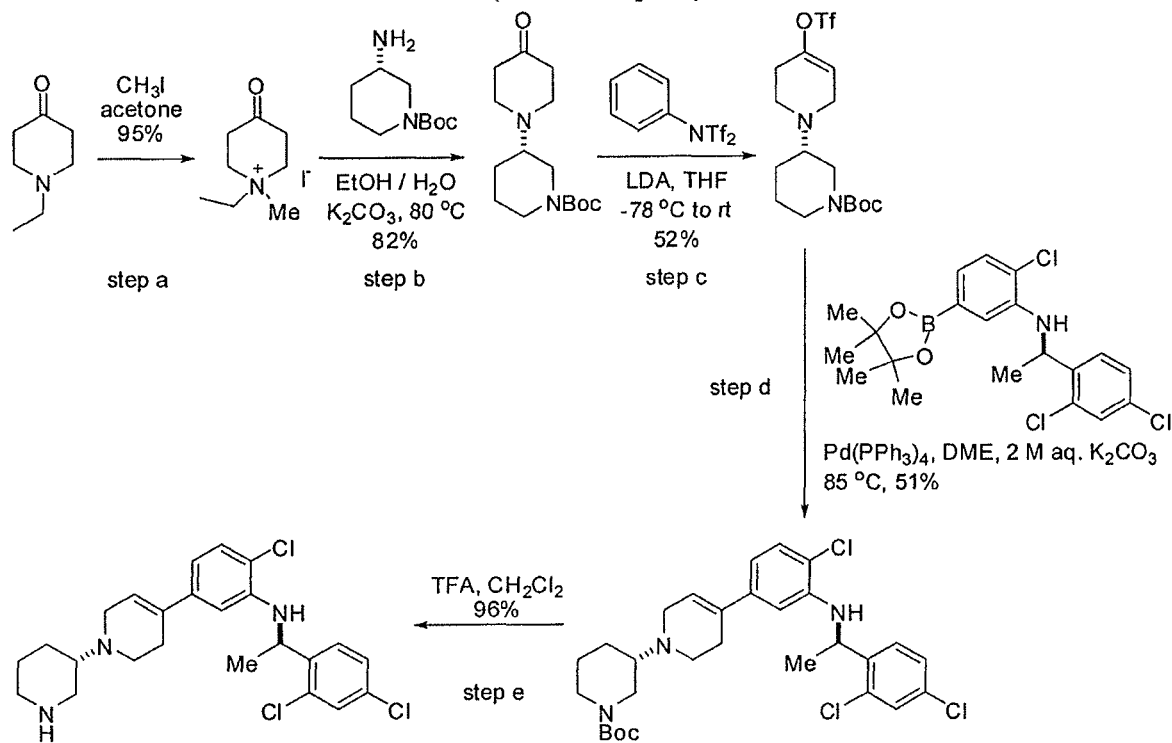
FIG. 6 provides a reaction scheme for the preparation of 2-chloro-N—((R)-1-(2,4-dichlorophenyl)ethyl)-5-(1-((S)-3-piperidyl)-3,6-dihydro-2H-pyridin-4-yl)aniline (see Example 3).

Synthesis of 2-chloro-N—((R)-1-(2,4-dichlorophenyl)ethyl)-5-(1-((S)-3-piperidyl)-3,6-dihydro-2H-pyridin-4-yl)aniline (See FIG. 6)

a) Methyl iodide (7.3 mL, 117.8 mmol) was slowly added to a solution of the N-ethylpiperidone (13.4 mL, 98.2 mmol) in acetone (100 mL) at room temperature. The reaction mixture was stirred for 5 h and a solid was formed. The colorless solid was collected by filtration, washed with acetone (30 mL), and dried under vacuum to give the quaternary salt (25 g, 92.9 mmol, 95%).

b) N-Ethyl-N-methyl-4-oxo-piperidinium iodide (8.0 g, 29.7 mmol) dissolved in deionized water (30 mL) was added to a refluxing solution of (S)-1-boc-3-aminopiperidine (5 g, 25 mmol) and potassium carbonate (K$_2$CO$_3$) (3.5 g, 25 mmol) in ethanol (125 mL) at 80° C. The heating was continued for 4 h and excess solvent was removed in vacuo. The aqueous layer was extracted with ethyl acetate (3×60 mL), and the combined organic layers were dried (Na$_2$SO$_4$), filtered, and concentrated in vacuo. The residue was purified by flash chromatography (SiO$_2$, 1-5% methanol in dichloromethane) to give the desired compound (5.8 g, 20.5 mmol, 82%). MS: (ES) m/z calculated for C$_{15}$H$_{27}$N$_2$O$_3$ [M+H]$^+$ 283.2, found 283.

c) To a solution of 1-((3S)-3-piperidyl)piperidin-4-one (3.3 g, 11.68 mmol) in anhydrous THF (20 mL) at −78° C. under nitrogen was slowly added a solution of lithium diisopropylamide (LDA) (2 M solution in THF, 7 mL, 14 mmol). After the addition is complete, the reaction mixture was warmed to −20° C. over 30 min. The solution was re-cooled to −78° C., and a solution of N-phenyl-bis(trifluoromethanesulfonimide) (5.4 g, 15.2 mmol) dissolved in anhydrous THF (20 mL) was added dropwise. The reaction mixture was warmed to room temperature over 6 h, and quenched with saturated aqueous ammonium chloride (NH$_4$Cl) solution. The aqueous layer was extracted with ethyl acetate (2×50 mL). The combined organic layers were dried (Na$_2$SO$_4$), filtered, and concentrated in vacuo. The residue was purified flash chromatography (SiO$_2$, 0-20% ethyl acetate in dichloromethane) to give the pure compound (2.5 g, 6.0 mmol, 52%). MS: (ES) m/z calculated for C$_{16}$H$_{26}$F$_3$N$_2$O$_5$S [M+H]$^+$ 415.4, found 415.

d) To a solution (S)-t-butyl 3-(4-(trifluoromethylsulfonyloxy)-5,6-dihydropyridin-1(2H)-yl)piperidine-1-carboxylate (2.0 g, 4.8 mmol) and (R)-2-chloro-N-(1-(2,4-dichlorophenyl)ethyl)-5-(4,4,5,5-tetramethyl-1,3,2-dioxaborolan-2-yl)aniline (prepared from example 2, 2.3 g, 5.3 mmol) in dimethoxyethane (12 mL) was added tetrakis(triphenylphosphine)palladium(0) (Pd(PPh$_3$)$_4$) (0.28 g, 0.24 mmol) and 2 M aqueous potassium carbonate solution (6 mL, 12 mmol). The mixture was purged with nitrogen for 5 min, and heated at 85° C. under nitrogen for 5 h. After cooling to room temperature, the reaction mixture was diluted with ethyl acetate. The organic layer was washed with brine, dried (Na$_2$SO$_4$), filtered, and concentrated in vacuo. The residue was purified by flash chromatography (SiO$_2$, 0-5% methanol in dichloromethane) to give the pure compound (1.4 g, 2.5 mmol, 51%). MS: (ES) m/z calculated for C$_{16}$H$_{26}$F$_3$N$_2$O$_5$S [M+H]$^+$ 564.2, found 564.

e) Trifluoroacetic acid (1.5 mL) was added to a solution of (S)-t-butyl 3-(4-(4-chloro-3-((R)-1-(2,4-dichlorophenyl)ethylamino)phenyl)-5,6-dihydropyridin-1(2H)-yl)piperidine-1-carboxylate (0.83 g, 1.5 mmol) in dichloromethane (3 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried (Na$_2$SO$_4$), filtered, and concentrated in vacuo. The crude product was used without further purification (0.65 g, 1.4 mmol, 96%). MS: (ES) m/z calculated for C$_{24}$H$_{29}$ClN$_3$ [M+H]$^+$ 464.1, found 464.

Example 4

Figure 7:
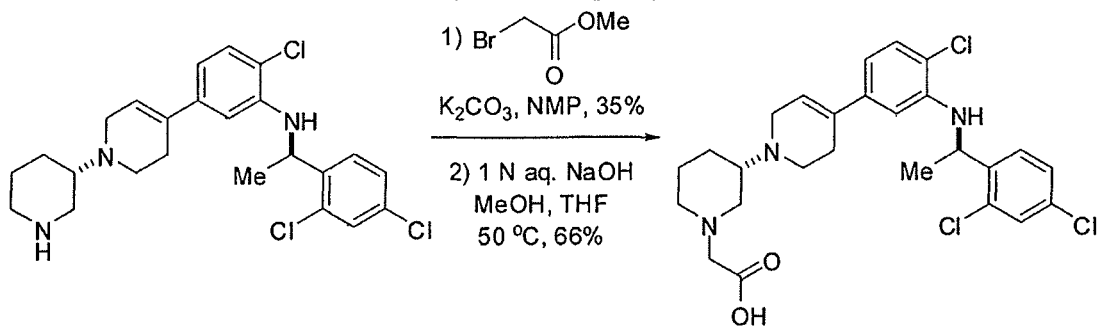
FIG. 7 provides a reaction scheme for the preparation of 2-((S)-3-(4-(4-chloro-3-((R)-1-(2,4-dichlorophenyl)ethylamino)phenyl)-5,6-dihydropyridin-1(2H)-yl)piperidin-1-yl)acetic acid (see Example 4).

Synthesis of 2-((S)-3-(4-(4-chloro-3-((R)-1-(2,4-dichlorophenyl)ethylamino)phenyl)-5,6-dihydropyridin-1(2H)-yl)piperidin-1-yl)acetic Acid (See FIG. 7)

A mixture of the crude 2-chloro-N—((R)-1-(2,4-dichlorophenyl)ethyl)-5-(1-((S)-3-piperidyl)-3,6-dihydro-2H-pyridin-4-yl)aniline (0.10 g, 0.21 mmol), 2-bromomethyl acetate (0.036 g, 0.24 mmol), and potassium carbonate (0.058 g, 0.42 mmol) in 1-methyl-2-pyrrolidinone (NMP) (0.8 mL) was stirred under nitrogen for 12 h. The reaction mixture was diluted with ethyl acetate, washed with deionized water, brine, dried ($Na_2SO_4$), filtered, and concentrated in vacuo. The residue was purified by flash chromatography ($SiO_2$, 0-5% methanol in dichloromethane) to give the desired compound (0.040 g, 0.075 mmol, 35%). MS: (ES) m/z calculated for $C_{27}H_{33}Cl_3N_3O_2$ [M+H]$^+$ 536.2, found 536. The resulting ester was dissolved in methanol (0.14 mL) and THF (0.6 mL), and aqueous 1 N sodium hydroxide solution (0.14 mL, 0.14 mmol) was added. The reaction mixture was heated at 50° C. for 1 h, and cooled to room temperature. The solution was diluted with deionized water (1 mL), and the crude was purified by reverse phase HPLC (C18 column, acetonitrile-$H_2O$ with 0.1% TFA as eluent) to give a light yellow solid as TFA salt (0.037 g, 0.052 mmol, 66%). $^1$H NMR (400 MHz, $CD_3OD$) δ 7.45 (d, J=2.8 Hz, 1H), 7.41 (d, J=8.4 Hz, 1H), 7.25-7.21 (m, 2H), 6.72 (dd, J=2.2, 8.4 Hz, 1H), 6.31 (d, J=2.2 Hz, 1H), 5.91 (bs, 1H), 5.01 (q, J=7.0 Hz, 1H), 4.00-3.90 (m, 2H), 3.70-3.44 (m, 6H), 3.23-3.18 (m, 1H), 3.00 (bs, 1H), 2.90-2.82 (m, 1H), 2.70 (bs, 2H), 2.10-1.90 (m, 5H), 1.84-1.74 (m, 1H), 1.58 (d, J=6.6 Hz, 3H); MS: (ES) m/z calculated for $C_{26}H_{31}Cl_3N_3O_2$ [M+H]$^+$ 522.2, found 522.

Example 5

Figure 8:
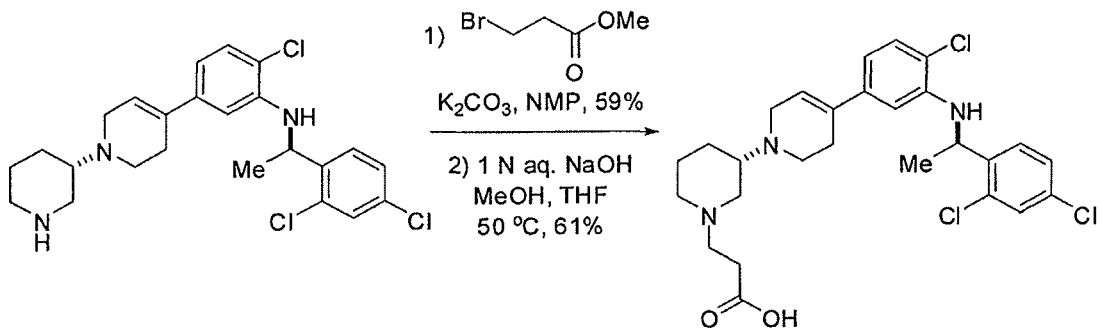
FIG. 8 provides a reaction scheme for the preparation of 3-((S)-3-(4-(4-chloro-3-((R)-1-(2,4-dichlorophenyl)ethylamino)phenyl)-5,6-dihydropyridin-1(2H)-yl)piperidin-1-yl)propanoic acid (see Example 5).

Synthesis of 3-((S)-3-(4-(4-chloro-3-((R)-1-(2,4-dichlorophenyl)ethylamino)phenyl)-5,6-dihydropyridin-1(2H)-yl)piperidin-1-yl)propanoic Acid (See FIG. 8)

The titled compound was prepared as illustrated in example 4 to give a light yellow solid as TFA salt. $^1$H NMR (400 MHz, $CD_3OD$) δ 7.44 (d, J=2.8 Hz, 1H), 7.41 (d, J=8.4 Hz, 1H), 7.25-7.21 (m, 2H), 6.71 (dd, J=2.2, 8.0 Hz, 1H), 6.29 (d, J=2.2 Hz, 1H), 5.91 (bs, 1H), 5.00 (q, J=6.6 Hz, 1H), 4.00-3.70 (m, 5H), 3.60-3.40 (m, 6H), 3.25-3.21 (m, 1H), 3.00-2.92 (m, 1H), 2.88 (t, J=6.9 Hz, 2H), 2.78-2.64 (m, 2H), 2.30-2.10 (m, 2H), 1.96-1.80 (m, 2H), 1.58 (d, J=6.6 Hz, 3H); MS: (ES) m/z calculated for $C_{27}H_{33}Cl_3N_3O_2$ [M+H]$^+$ 536.1, found 536.

Example 6

Figure 9:
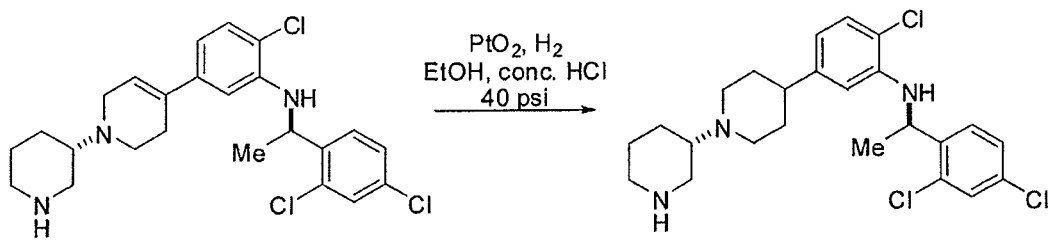
FIG. 9 provides a reaction scheme for the preparation of 5-((S)-1,3'-bipiperidin-4-yl)-2-chloro-N—((R)-1-(2,4-dichlorophenyl)ethyl)aniline (see Example 6).

Synthesis of 5-((S)-1,3'-bipiperidin-4-yl)-2-chloro-N—((R)-1-(2,4-dichlorophenyl)ethyl)aniline (See FIG. 9)

A mixture of the crude 2-chloro-N-((1R)-1-(2,4-dichlorophenyl)ethyl)-5-(1-((3S)-3-piperidyl)-3,6-dihydro-2H-pyridin-4-yl)aniline (0.30 g, 0.63 mmol), platinum(IV) oxide ($PtO_2$) (5% by weight, 0.045 g) in ethanol (3 mL) containing concentrated hydrochloric acid (conc. HCl) (0.20 mL, 2.20 mmol) in a Paar shaker flask was hydrogenated at 40 psi for 45 min. The reaction mixture was diluted with ethanol, and filtered through the Celite. The filtrate was concentrated in vacuo, and the resulting residue was diluted with dichloromethane (25 mL). The organic layer was washed with saturated aqueous sodium bicarbonate solution, dried ($Na_2SO_4$), filtered, and concentrated in vacuo. The residue was used without further purification (0.27 g, 0.058 mmol). MS: (ES) m/z calculated for $C_{24}H_{31}Cl_3N_3$ [M+H]$^+$ 466.2, found 466.

Example 7

Figure 10:
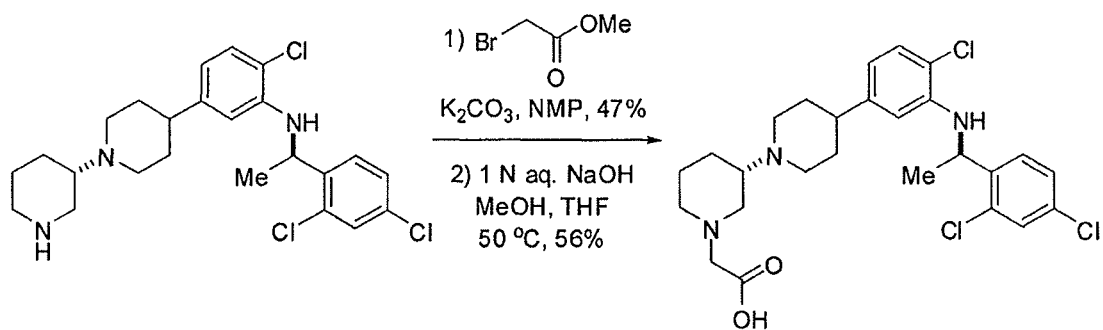
FIG. 10 provides a reaction scheme for the preparation of 2-((S)-4-(4-chloro-3-((R)-1-(2,4-dichlorophenyl)ethylamino)phenyl)-1,3'-bipiperidin-1'-yl)acetic acid (see Example 7).

Synthesis of 2-((S)-4-(4-chloro-3-((R)-1-(2,4-dichlorophenyl)ethylamino)phenyl)-1,3'-bipiperidin-1'-yl)acetic Acid (See FIG. 10)

The titled compound was prepared as illustrated in example 4 to give a white solid as TFA salt. $^1$H NMR (400 MHz, $CD_3OD$) δ 7.46 (d, J=2.2 Hz, 1H), 7.40 (d, J=8.0 Hz, 1H), 7.26-7.24 (m, 1H), 7.20 (d, J=8.0 Hz, 1H), 6.52 (dd, J=1.9, 8.1 Hz, 1H), 6.15 (d, J=1.9 Hz, 1H), 5.01 (q, J=6.6 Hz, 1H), 3.74-3.39 (m, 6H), 3.20-3.06 (m, 5H), 2.87-2.80 (m, 1H), 2.72-2.64 (m, 1H), 2.10-1.78 (m, 9H), 1.57 (d, J=6.6 Hz, 3H); MS: (ES) m/z calculated for $C_{26}H_{33}Cl_3N_3O_2$ [M+H]$^+$ 524.2, found 524.

Example 8

Figure 11:
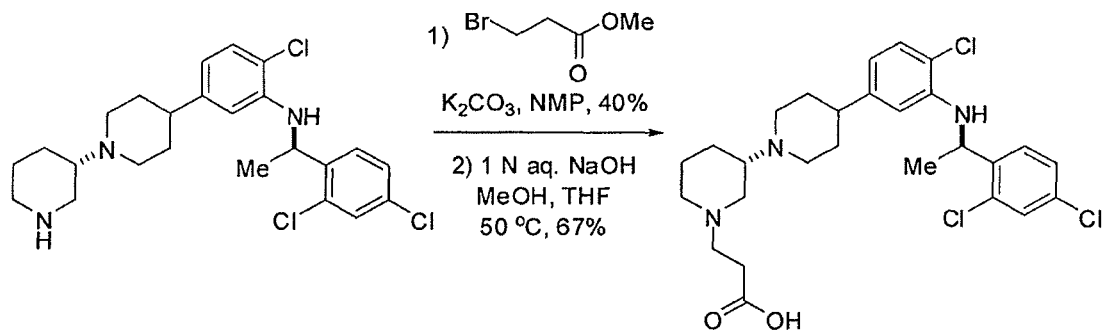
FIG. 11 provides a reaction scheme for the preparation of 3-((S)-4-(4-chloro-3-((R)-1-(2,4-dichlorophenyl)ethylamino)phenyl)-1,3'-bipiperidin-1'-yl)propanoic acid (see Example 8).

Synthesis of 3-((S)-4-(4-chloro-3-((R)-1-(2,4-dichlorophenyl)ethylamino)phenyl)-1,3'-bipiperidin-1'-yl)propanoic Acid (See FIG. 11)

The titled compound was prepared as illustrated in example 4 to give a white solid as TFA salt. $^1$H NMR (400 MHz, $CD_3OD$) δ 7.44 (d, J=2.2 Hz, 1H), 7.40 (d, J=8.4 Hz, 1H), 7.26-7.23 (m, 1H), 7.20 (d, J=8.1 Hz, 1H), 6.51 (dd, J=1.9, 8.1 Hz, 1H), 6.15 (d, J=2.2 Hz, 1H), 4.98 (q, J=6.6 Hz, 1H), 3.91-3.88 (m, 1H), 3.74-3.66 (m, 1H), 3.59-3.56 (m, 3H), 3.50-3.42 (m, 2H), 3.30-3.18 (m, 5H), 3.00-2.92 (m, 1H), 2.89 (t, J=7.0 Hz, 2H), 2.72-2.64 (m, 1H), 2.28-2.15 (m, 2H), 2.02-1.81 (m, 6H), 1.57 (d, J=6.6 Hz, 3H); MS: (ES) m/z calculated for $C_{27}H_{35}Cl_3N_3O_2$ [M+H]$^+$ 538.2, found 538.

Example 9

Figure 12:
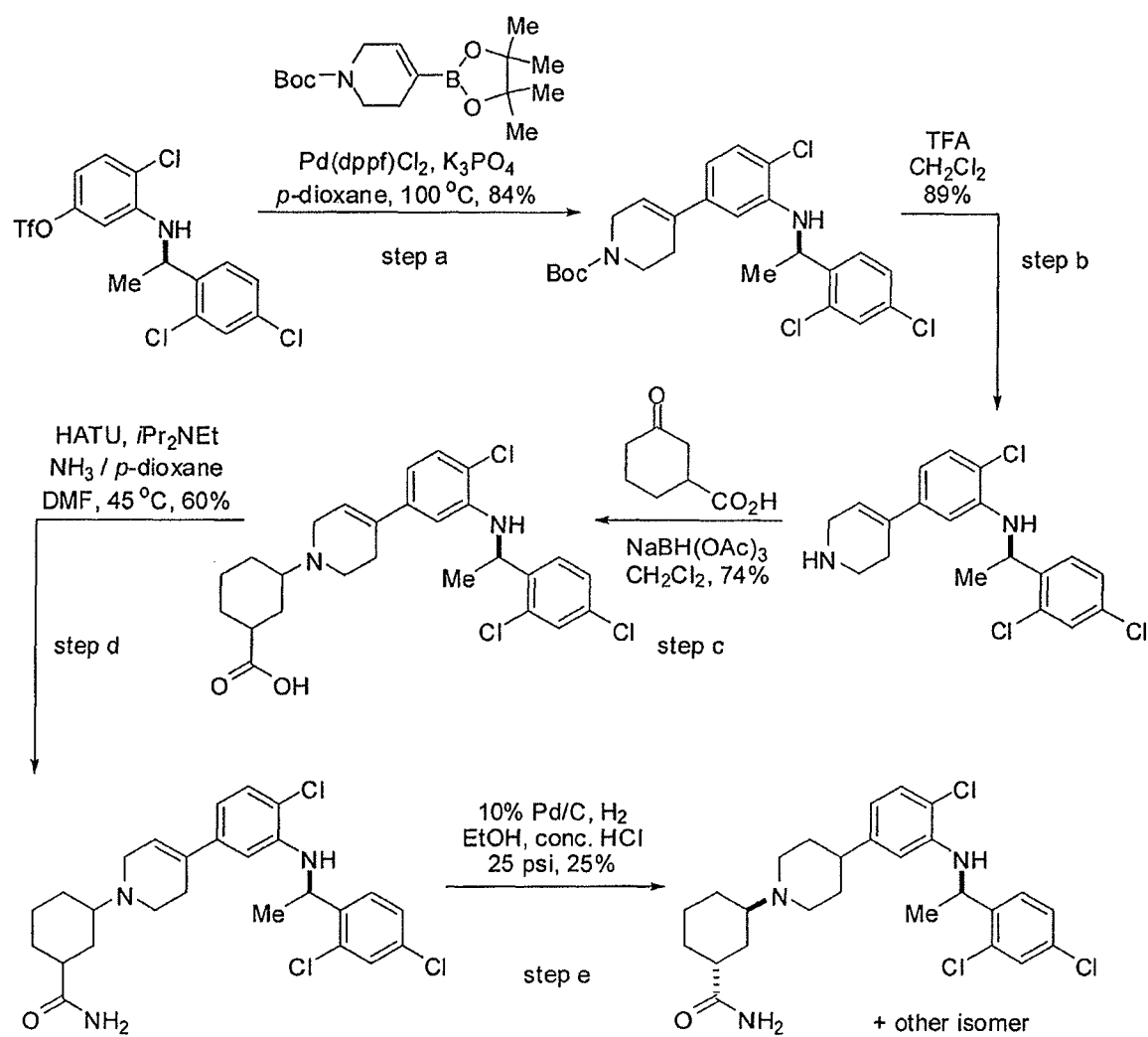
FIG. 12 provides a reaction scheme for the preparation of (1R,3R)-3-(4-(4-chloro-3-((R)-1-(2,4-dichlorophenyl)ethylamino)phenyl)piperidin-1-yl)cyclohexanecarboxamide (see Example 9).

Synthesis of (1R,3R)-3-(4-(4-chloro-3-((R)-1-(2,4-dichlorophenyl)ethylamino)phenyl)piperidin-1-yl)cyclohexanecarboxamide (See FIG. 12)

a) A mixture of (R)-4-chloro-3-(1-(2,4-dichlorophenyl)ethylamino)phenyl trifluoromethanesulfonate (prepared from Example 2 step d, 5.0 g, 11.4 mmol), (N-t-butoxycarbonyl-1,2,3,6-tetrahydropyridin-4-yl)boronic acid pincol ester (5.8 g, 14.8 mmol), Pd(dppf)$Cl_2$ (0.5 g, 0.068 mmol), and potassium phosphate tribasic ($K_3PO_4$) (6.0 g, 34.2 mmol) in p-dioxane (100 mL) was purged with nitrogen for 5 min, and then heated at 100° C. for 1 h. After cooling to room temperature, the mixture was filtered and washed with ethyl acetate (50 mL). The filtrate was concentrated in vacuo. The resulting crude mixture was diluted with ethyl acetate (200 mL), washed with deionized water, brine, dried ($Na_2SO_4$), and concentrated in vacuo. The resulting crude was purified by flash chromatography ($SiO_2$, 0-20% methanol in dichloromethane) to afford the desired product (4.8 g, 9.5 mmol, 84%).

b) Trifluoroacetic acid (2.0 mL) was added to a solution of (R)-t-butyl 4-(4-chloro-3-(1-(2,4-dichlorophenyl)ethylamino)phenyl)-5,6-dihydropyridine-1(2H)-carboxylate (4.8 g, 9.5 mmol) in dichloromethane (6 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried ($Na_2SO_4$), filtered, and concentrated in vacuo. The crude product was used without further purification (3.2 g, 8.4 mmol, 89%).

c) To a stirred solution of the crude (R)-2-chloro-N-(1-(2,4-dichlorophenyl)ethyl)-5-(1,2,3,6-tetrahydropyridin-4-yl)aniline (0.65 g, 0.17 mmol) and 3-oxocyclohexanecarboxylic acid (0.036 g, 0.26 mmol) in dichloromethane (4 mL) was added sodium triacetoxyborohydride (NaBH(OAc)$_3$) (0.054 g, 0.25 mmol). The reaction mixture was stirred at room temperature for 18 h. The reaction mixture was quenched with aqueous saturated sodium bicarbonate and extracted with dichloromethane. The organic layer was dried (Na$_2$SO$_4$), filtered, and concentrated in vacuo. The resulting crude was purified by flash chromatography (SiO$_2$, 10-40% ethyl acetate in hexanes) to afford 3-(4-(4-chloro-3-((R)-1-(2,4-dichlorophenyl)ethylamino)phenyl)-5,6-dihydropyridin-1(2H)-yl)cyclohexanecarboxylic acid as the desired product (0.064 g, 0.13 mmol, 74%).

d) To a stirred solution of the 3-(4-(4-chloro-3-((R)-1-(2,4-dichlorophenyl)ethylamino)phenyl)-5,6-dihydropyridin-1(2H)-yl)cyclohexanecarboxylic acid (0.070 g, 0.14 mmol) and N,N,N',N'-tetramethyl-O-(7-azabenzotriazol-1-yl)uronium hexafluorophosphate (HATU) (0.063 g, 0.165 mmol) in anhydrous N,N-dimethylforamide (DMF) (2.5 mL) was added a solution of ammonia (0.5 M in p-dioxane, 2.7 mL, 1.4 mmol) and iPr$_2$NEt (0.045 g, 0.34 mmol). The reaction was heated at 45° C. for 3 h. After cooling to room temperature, the reaction mixture was quenched with deionized water, extracted with diethyl ether. The organic layer was dried (Na$_2$SO$_4$), filtered, and concentrated in vacuo. The crude product was purified by flash chromatography (SiO$_2$, 0-15% methanol in dichloromethane) to afford the desired product (0.042 g, 0.083 mmol, 60%).

e) A mixture of the 3-(4-(4-chloro-3-((R)-1-(2,4-dichlorophenyl)ethylamino)phenyl)-5,6-dihydropyridin-1(2H)-yl)cyclohexanecarboxamide (0.154 g, 0.20 mmol), palladium on carbon (Pd/C) (10% by weight, 0.05 g) in ethanol (7 mL) containing concentrated hydrochloric acid (4 drops) in a Paar shaker flask was hydrogenated at 25 psi for 1 h. The reaction mixture was diluted with ethanol, and filtered through Celite. The filtrate was concentrated in vacuo, and the resulting residue was purified by flash chromatography (SiO$_2$, 5% triethylamine in ethyl acetate) to separate the desired isomer as a white solid (0.038 g, 0.075 mmol, 25%). $^1$H NMR (400 MHz, CD$_3$OD) δ 7.45-7.41 (m, 2H), 7.26 (dd, J=2.0, 8.4 Hz, 1H), 7.21 (d, J=8.0 Hz, 1H), 6.57 (d, J=8.0 Hz, 1H), 6.21 (s, 1H), 4.99 (dd, J=6.8, 13.2 Hz, 1H), 3.76-3.71 (m, 1H), 3.53-3.52 (m, 3H), 3.20-3.12 (m, 2H), 2.99-2.93 (m, 1H), 2.71-2.65 (m, 1H), 2.47 (d, J=11.6 Hz, 1H), 2.35 (d, J=13.2 Hz, 1H), 2.18-2.10 (m, 2H), 1.99-1.82 (m, 6H), 1.68-1.74 (m, 1H), 1.64-1.51 (m, 6H); MS: (ES) m/z calculated for C$_{26}$H$_{33}$Cl$_3$N$_3$O [M+H]$^+$ 508.2, found 508.4.

Example 10

Figure 13:
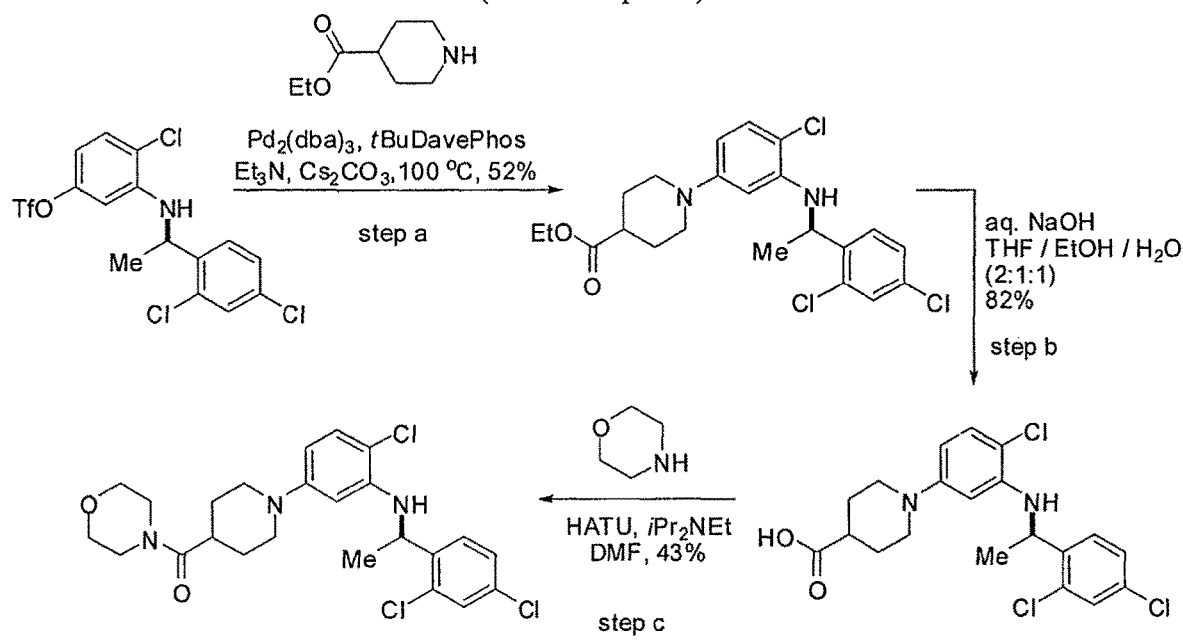
FIG. 13 provides a reaction scheme for the preparation of (R)-(1-(4-chloro-3-(1-(2,4-dichlorophenyl)ethylamino)phenyl)piperidin-4-yl)(morpholino)methanone (see Example 10).

Synthesis of (R)-(1-(4-chloro-3-(1-(2,4-dichlorophenyl)ethylamino)phenyl)piperidin-4-yl)(morpholino)methanone (See FIG. 13)

a) A mixture of (R)-4-chloro-3-(1-(2,4-dichlorophenyl)ethylamino)phenyl trifluoromethanesulfonate (Example 2 step d, 1.5 g, 3.4 mmol), ethyl 4-piperidinecarboxylate (1.18 g, 8.4 mmol), tBuDavePhos (0.12 g, 0.34 mmol), and cesium carbonate (Cs$_2$CO$_3$) (2.7 g, 8.4 mmol) in triethylamine (12 mL) was purged with nitrogen for 5 min. Addition of Pd$_2$(dba)$_3$ (0.15 g, 0.14 mmol) was followed, and the mixture was purged with nitrogen for 1 min. The reaction was then heated at 100° C. for 18 h. After cooling to room temperature, the mixture was filtered and washed with EtOAc (50 mL). The filtrate was concentrated in vacuo. The resulting crude mixture was purified by flash chromatography (SiO$_2$, 0-15% ethyl acetate in hexanes) to afford the coupled product as a viscous oil (0.82, 1.82 mmol, 52%).

b) To a stirred solution of (R)-ethyl 1-(4-chloro-3-(1-(2,4-dichlorophenyl)ethylamino)phenyl)piperidine-4-carboxylate (3.1 g, 6.8 mmol) in 2:1 THF/EtOH (12 mL) was added a solution of sodium hydroxide (1.4 g, 34.1 mmol) dissolved in deionized water (4 mL). The reaction mixture was stirred at room temperature for 4 h, and the mixture was adjusted to pH-7 with aqueous 6 N hydrochloric acid. The aqueous layer was extracted with ethyl acetate (2×50 mL). The combined organic layers were dried (Na$_2$SO$_4$), filtered, and concentrated in vacuo. The crude product was purified by flash chromatography (SiO$_2$, 0-25% methanol in dichloromethane) to give (R)-1-(4-chloro-3-(1-(2,4-dichlorophenyl)ethylamino)phenyl)piperidine-4-carboxylic acid (2.4 g, 5.6 mmol, 82%).

c) To a stirred solution of the (R)-1-(4-chloro-3-(1-(2,4-dichlorophenyl)ethylamino)phenyl)piperidine-4-carboxylic acid (0.0.05 g, 0.12 mmol) and N-methylmorpholine (0.01 g, 0.12 mmol) in DMF (1.5 mL) was added HATU (0.049 g, 0.13 mmol) and iPr$_2$NEt (0.75 g, 5.8 mmol). The reaction mixture was stirred at room temperature for 2 h, and quenched with deionized water. The aqueous layer was extracted with diethyl ether (2×10 mL). The organic layer was dried (Na$_2$SO$_4$), filtered, and concentrated in vacuo. The crude product purified by reverse phase HPLC (C18 column, acetonitrile-H$_2$O with 0.1% TFA as eluent) to give a white solid (0.025 g, 0.050 mmol, 43%). $^1$H NMR (400 MHz, CDCl$_3$) δ 7.36-7.33 (m, 1H), 7.17 (dd, J=1.6, 8.4 Hz, 1H), 7.06 (d, J=8.8 Hz, 1H), 6.18 (dd, J=2.8, 8.4 Hz, 1H), 5.78 (d, J=2.4 Hz, 1H), 4.90 (ddd, J=6.4, 6.4, 12.4 Hz, 1H), 4.65 (d, J=5.2 Hz, 1H), 3.68-3.63 (m, 5H), 3.50-3.47 (m, 3H), 2.64-2.48 (m, 3H), 1.92-1.80 (m, 5H), 1.71-1.67 (m, 2H), 1.53 (d, J=6.4 Hz, 3H); MS: (ES) m/z calculated for C$_{24}$H$_{29}$Cl$_3$N$_3$O$_2$ [M+H]$^+$ 496.1, found 496.3.

Example 11

Figure 14:
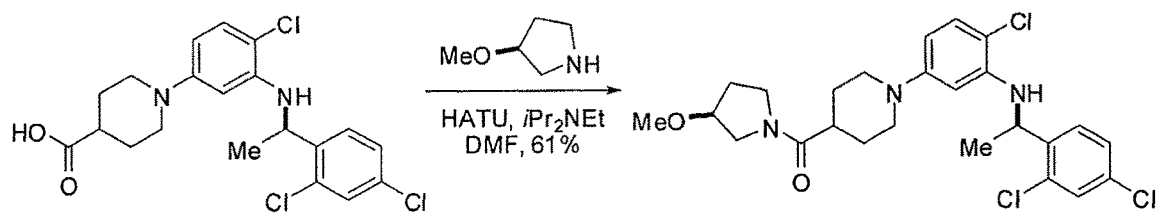
FIG. 14 provides a reaction scheme for the preparation of (1-(4-chloro-3-((R)-1-(2,4-dichlorophenyl)ethylamino)phenyl)piperidin-4-yl)((S)-3-methoxypyrrolidin-1-yl)methanone (see Example 11).

Synthesis of (1-(4-chloro-3-((R)-1-(2,4-dichlorophenyl)ethylamino)phenyl)piperidin-4-yl)((S)-3-methoxypyrrolidin-1-yl)methanone (See FIG. 14)

The titled compound was prepared as illustrated in Example 10 c using (3S)-methoxypyrrolidine as the coupling partner to give a white solid. $^1$H NMR (400 MHz, CDCl$_3$) δ 7.36-7.32 (m, 2H), 7.16 (dd, J=2.2, 8.4 Hz, 1H), 7.04 (d, J=8.6 Hz, 1H), 6.16 (dd, J=2.5, 8.8 Hz, 1H), 5.78 (d, J=2.6 Hz, 1H), 4.87 (q, J=6.6 Hz, 1H), 4.62 (d, J=5.2 Hz, 1H), 4.06-3.92 (m, 1H), 3.70-3.42 (m, 6H), 3.32 (s, 3H). 2.64-2.32 (m, 3H), 2.18-1.70 (m, 6H), 1.52 (d, J=6.6 Hz, 3H); MS: (ES) m/z calculated for C$_{25}$H$_{31}$Cl$_3$N$_3$O$_2$ [M+H]$^+$ 510.1, found 510.

Example 12

Figure 15:
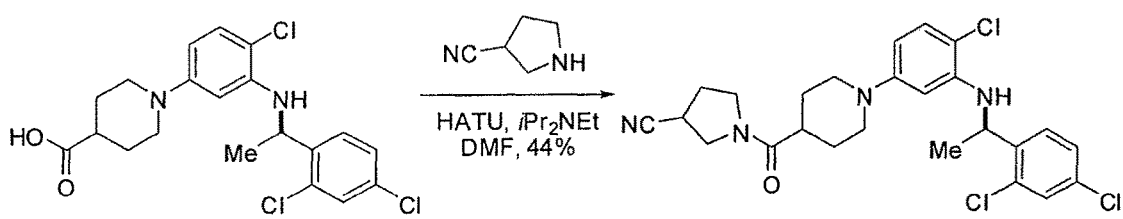
FIG. 15 provides a reaction scheme for the preparation of 1-(1-(4-chloro-3-((R)-1-(2,4-dichlorophenyl)ethylamino)phenyl)piperidine-4-carbonyl)pyrrolidine-3-carbonitrile (see Example 12).

Synthesis of 1-(1-(4-chloro-3-((R)-1-(2,4-dichlorophenyl)ethylamino)phenyl)piperidine-4-carbonyl)pyrrolidine-3-carbonitrile (See FIG. 15)

The titled compound was prepared as illustrated in Example 10 c using 3-pyrrolidinecarbonitrile as the coupling partner to give a white solid. $^1$H NMR (400 MHz, CDCl$_3$) δ 7.37-7.33 (m, 2H), 7.17 (dd, J=2.0, 8.0 Hz, 1H), 7.06 (d, J=8.4 Hz, 1H), 6.18 (dd, J=2.8, 8.4 Hz, 1H), 5.78 (d, J=2.8 Hz, 1H), 4.90 (ddd, J=6.4, 6.4, 12.4 Hz, 1H), 4.64 (d, J=5.2 Hz, 1H), 3.86-3.70 (m, 2H), 3.67-3.58 (m, 1H), 3.51-3.45 (m, 2H), 3.23-3.12 (m, 1H), 2.96 (s, 1H), 2.89 (s, 1H), 2.61-2.53 (m, 2H), 2.39-2.19 (m, 3H), 1.87-1.72 (m, 3H), 1.53 (d, J=6.4 Hz, 3H); MS: (ES) m/z calculated for $C_{25}H_{28}Cl_3N_4O$ [M+H]$^+$ 505.1, found 505.2.

Example 13

Figure 16:
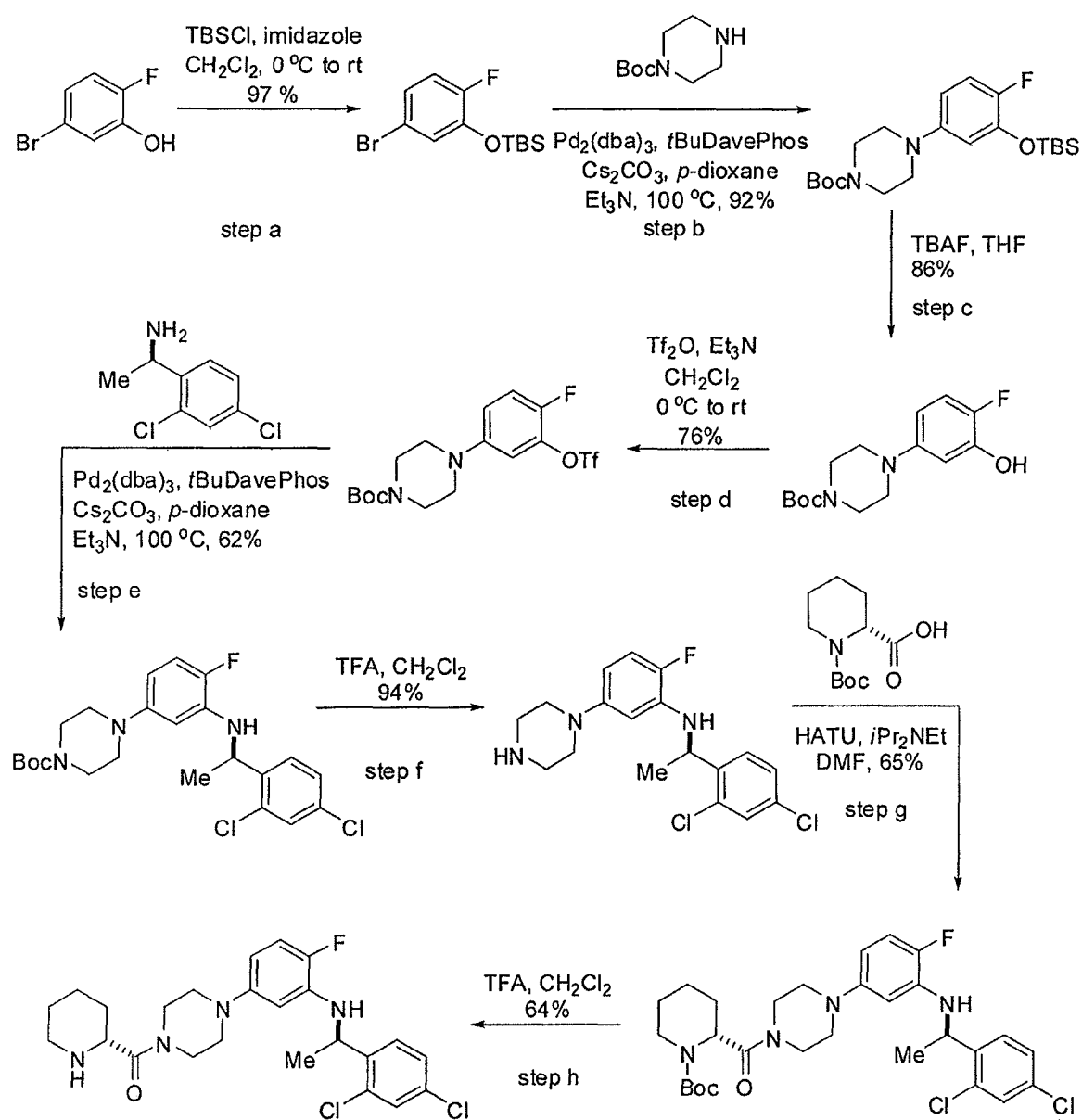
FIG. 16 provides a reaction scheme for the preparation of (4-(3-((R)-1-(2,4-dichlorophenyl)ethylamino)-4-fluorophenyl)piperazin-1-yl)((R)-piperidin-2-yl)methanone (see Example 13).

Synthesis of (4-(3-((R)-1-(2,4-dichlorophenyl)ethylamino)-4-fluorophenyl)piperazin-1-yl)((R)-piperidin-2-yl)methanone (See FIG. 16)

a) To a stirred solution of 5-bromo-2-fluorophenol (3.8 g, 20.0 mmol) in dichloromethane (50 mL) at 0° C. was added iPr$_2$NEt (1.5 g, 11.5 mmol) and t-butyldimethylchlorosilane (TBSCl) (3.6 g, 24.1 mmol). The mixture was stirred at 0° C. for 30 min, then at room temperature for 14 h. The reaction mixture was diluted with deionized water and extracted with dichloromethane (2×50 mL). The combined organic layers were dried (Na$_2$SO$_4$), filtered, and concentrated in vacuo. The crude was used without further purification (5.9 g, 19.4 mmol, 97%).

b) A mixture of (5-bromo-2-chlorophenoxy)-t-butyldimethylsilane (1.23 g, 4.04 mmol), N-t-butyloxycarbonylpiperazine (1.58 g, 10.1 mmol), tBuDavePhos (0.14 g, 0.4 mmol), and Cs$_2$CO$_3$ (3.5 g, 11.7 mmol) in 2:1 p-dioxane/triethylamine (12 mL) was purged with nitrogen for 10 min. Addition of Pd$_2$(dba)$_3$ (0.15 g, 0.16 mmol) was followed, and the mixture was purged with nitrogen for 1 min. The reaction was then heated at 100° C. for 4.5 h. After cooling to room temperature, the mixture was filtered and washed with EtOAc (50 mL). The filtrate was concentrated in vacuo. The resulting crude mixture was purified by flash chromatography (SiO$_2$, 5-30% ethyl acetate in hexanes) to yield t-butyl-4-(3-t-butyldimethylsilyloxy)-4-fluorophenyl)piperazine-1-carboxylate (1.5 g, 3.73 mmol, 92%).

c) To a stirred solution of t-butyl-4-(3-t-butyldimethylsilyloxy)-4-fluorophenyl)piperazine-1-carboxylate (2.5 g, 6.2 mmol) in anhydrous tetrahydrofuran (THF) (20 mL) added a solution of tetrabutylammonium fluoride (TBAF) (1 M solution in THF, 6.2 mL, 6.2 mmol), and the reaction mixture was stirred at room temperature for 1 h. The solution was diluted with deionized water and extracted with ethyl acetate (2×20 mL). The combined organic layers were washed with deionized water, brine, dried (Na$_2$SO$_4$), filtered, and concentrated in vacuo to give t-butyl 4-(4-fluoro-3-hydroxyphenyl)piperazine-1-carboxylate (1.5 g, 5.1 mmol, 86%). The solid compound was carried to the next step with out further purification.

d) To a stirred solution of the t-butyl 4-(4-fluoro-3-hydroxyphenyl)piperazine-1-carboxylate (1.35 g, 4.56 mmol) in dichloromethane (15 mL) at 0° C. was added triethylamine (0.75 g, 7.48 mmol) and TFA (1.58 g, 5.62 mmol). The reaction mixture was stirred at 0° C. for 15 min, then warm to room temperature and stirred for 30 min. The solution was diluted with deionized water, extracted with dichloromethane (2×10 mL). The combined organic layers were washed with brine, dried (Na$_2$SO$_4$), filtered, and concentrated in vacuo. The crude product was purified by flash chromatography (SiO$_2$, 5-25% ethyl acetate in hexanes) to afford t-butyl 4-(4-fluoro-3-(trifluoromethyl sulfonyloxy)phenyl)piperazine-1-carboxylate (1.53 g, 3.57 mmol, 76%).

e) To a mixture of t-butyl 4-(4-fluoro-3-(trifluoromethylsulfonyloxy)phenyl)piperazine-1-carboxylate (0.50 g, 1.17 mmol) and (1R)-1-(2,4-dichlorophenyl)ethanamine (0.58 g, 3.05 mmol), tBuDavePhos (0.025 g, 0.070 mmol), and Cs$_2$CO$_3$ (0.80 g, 2.44 mmol) in triethylamine (3 mL) was purged with nitrogen for 3 min. Addition of Pd$_2$(dba)$_3$ (0.034 g, 0.037 mmol) was followed, and the mixture was purged with nitrogen for 1 min. The resulting mixture was heated at 100° C. under nitrogen for 4 h. After cooling to room temperature, the suspension was filtered through a plug of Celite, and washed with ethyl acetate (25 mL). The filtrate was concentrated in vacuo and the resulting residue purified by flash chromatography (SiO$_2$, 10-50% ethyl acetate in hexanes) to afford (R)-t-butyl 4-(3-(1-(2,4-dichlorophenyl)ethylamino)-4-fluorophenyl)piperazine-1-carboxylate (0.36 g, 42.9 mmol, 62%).

f) Trifluoroacetic acid (1.5 mL) was added to a solution of (R)-t-butyl 4-(3-(1-(2,4-dichlorophenyl)ethylamino)-4-fluorophenyl)piperazine-1-carboxylate (0.52 g, 1.11 mmol) in dichloromethane (5 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried (Na$_2$SO$_4$), filtered, and concentrated in vacuo. The crude product was used without further purification (0.38 g, 1.4 mmol, 94%).

g) To a stirred solution of the (R)—N-(1-(2,4-dichlorophenyl)ethyl)-2-fluoro-5-(piperazin-1-yl)aniline (0.085 g, 0.23 mmol) and (R)-1-(t-butoxycarbonyl)piperdino-2-carboxylic acid (0.053 g, 0.23 mmol) in DMF (1.5 mL) was added HATU (0.11 g, 0.28 mmol) and iPr$_2$NEt (0.075 g, 0.58 mmol). The reaction mixture was stirred at room temperature for 2 h, and quenched with deionized water. The aqueous layer was extracted with diethyl ether (2×10 mL). The organic layer was dried (Na$_2$SO$_4$), filtered, and concentrated in vacuo. The crude product was purified by flash chromatography (SiO$_2$, 10-70% ethyl acetate in hexanes) to afford the desired product (0.080 g, 0.14 mmol, 65%).

h) Trifluoroacetic acid (1.5 mL) was added to a solution (R)-t-butyl 2-(4-(3-((R)-1-(2,4-dichlorophenyl)ethylamino)-4-fluorophenyl)piperazine-1-carbonyl)piperidine-1-carboxylate (0.080 g, 0.14 mmol) in dichloromethane (5 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried (Na$_2$SO$_4$), filtered, and concentrated in vacuo to give the title compound as a white solid (0.042 g, 0.088 mmol, 64%). $^1$H NMR (400 MHz, DMSO-d$_6$) δ 9.25 (s, 1H), 8.60-8.55 (m, 1H), 7.56 (dd, J=8.4, 8.4 Hz, 2H), 7.38 (dd, J=2.4, 8.4 Hz, 1H), 6.92 (dd, J=9.2, 11.2 Hz, 1H), 6.26-6.09 (m, 3H), 4.83 (dd, J=6.4, 13.6 Hz, 1H), 4.37 (t, J=11.2 Hz, 1H), 3.76-3.48 (m, 4H), 3.21 (d, J=11.2 Hz, 1H), 3.09-3.05 (m, 2H), 2.90-2.84 (m, 2H), 1.95 (d, J=13.6 Hz, 1H), 1.73-1.60 (m, 3H), 1.45 (d, J=6.8 Hz, 3H); MS: (ES) m/z calculated for $C_{24}H_{30}Cl_2FN_4O$ [M+H]$^+$ 479.2, found 479.4.

Example 14

Figure 17:
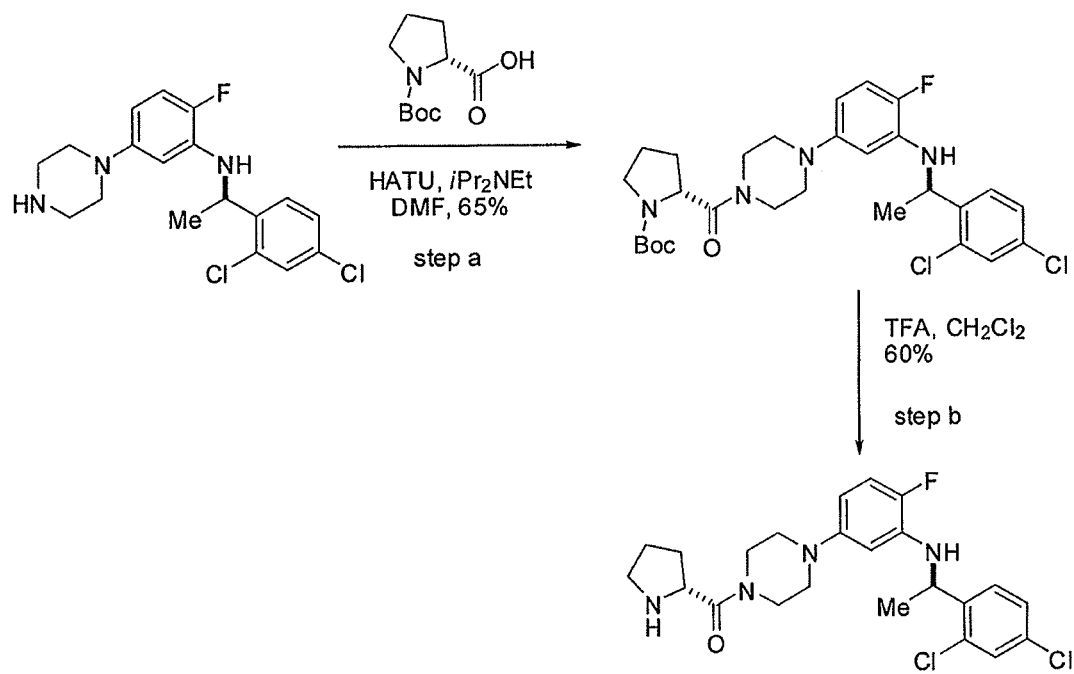
FIG. 17 provides a reaction scheme for the preparation of (4-(3-((R)-1-(2,4-dichlorophenyl)ethylamino)-4-fluorophenyl)piperazin-1-yl)((R)-pyrrolidin-2-yl)methanone (see Example 14).

Synthesis of (4-(3-((R)-1-(2,4-dichlorophenyl)ethylamino)-4-fluorophenyl)piperazin-1-yl)((R)-pyrrolidin-2-yl)methanone (See FIG. 17)

The titled compound was prepared as illustrated in Example 13 g-h using (R)-1-t-butoxycarbonylpyrrolidine-2-carboxylic acid as the coupling partner to give a white solid as the title compound. $^1$H NMR (400 MHz, DMSO-d$_6$) δ 10.0 (s, 1H), 8.47-8.44 (m, 2H), 7.56 (dd, J=2.0, 7.6 Hz, 1H), 7.38 (dd, J=2.0, 8.4 Hz, 1H), 6.92 (dd, J=10.4, 10.4 Hz, 1H), 6.26 (bs, 1H), 6.09 (bs, 1H), 4.83 (q, J=6.6 Hz, 1H), 4.59 (ddd, J=6.8, 6.8, 13.2 Hz, 1H), 3.67-3.65 (m, 4H), 3.24-3.13 (m, 2H), 3.01 (s, 4H), 2.38-2.33 (m, 1H), 1.93-1.76 (m, 3H), 1.49 (d, J=6.8 Hz, 3H); MS: (ES) m/z calculated for C$_{23}$H$_{28}$Cl$_2$FN$_4$O [M+H]$^+$ 465.2, found 465.3.

Figure 18:
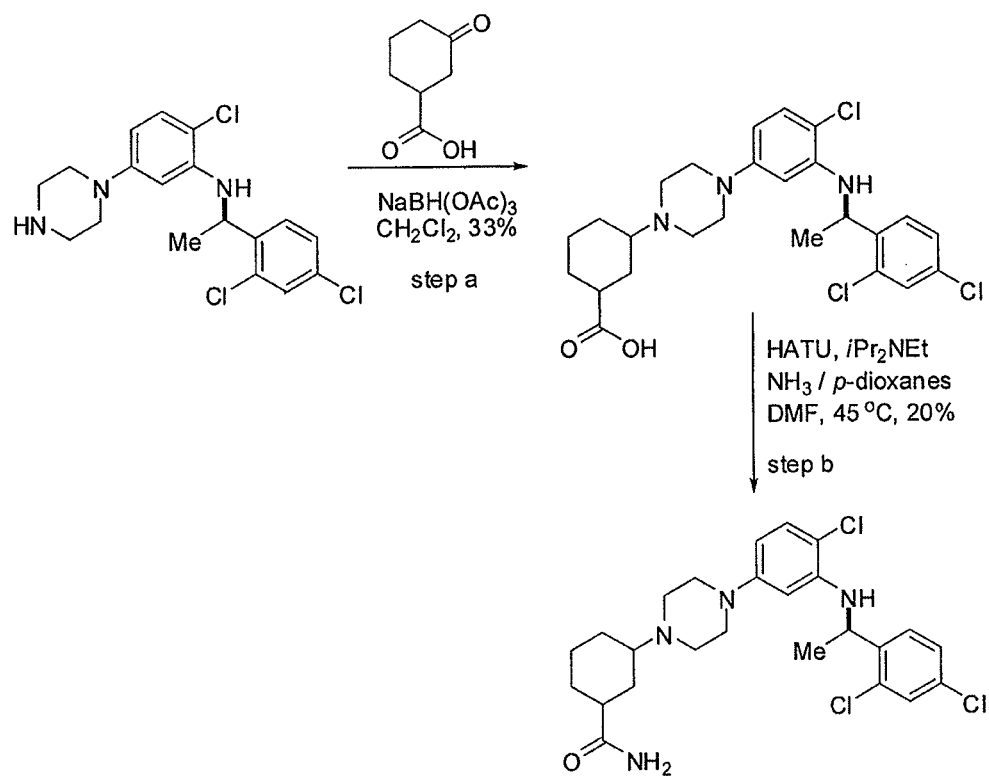
FIG. 18 provides a reaction scheme for the preparation of 3-(4-(4-chloro-3-((R)-1-(2,4-dichlorophenyl)ethylamino)phenyl)piperazin-1-yl)cyclohexanecarboxamide (see Example 15).

Example 15: Synthesis of 3-(4-(4-chloro-3-((R)-1-(2,4-dichlorophenyl)ethylamino)phenyl)piperazin-1-yl)cyclohexanecarboxamide (See FIG. 18)

a) To a stirred solution of (R)-2-chloro-N-(1-(2,4-dichlorophenyl)ethyl)-5-(piperazin-1-yl)aniline (prepared as illustrated in example 13 using 5-bromo-2-chlorophenol as starting material, 0.20 g, 0.54 mmol) and 3-oxocyclohexanecarboxylic acid (0.15 g, 1.1 mmol) in dichloromethane (4 mL) was added NaBH(OAc)$_3$ (0.153 g, 1.1 mmol). The reaction mixture was stirred at room temperature for 18 h, and quenched with diluted with aqueous saturated sodium bicarbonate. The aqueous layer was extracted with dichloromethane. The organic layer was dried (Na$_2$SO$_4$), filtered, and concentrated in vacuo. The resulting crude was purified by flash chromatography (SiO$_2$, 10-50% ethyl acetate in hexanes) to afford the desired product (0.092 g, 0.18 mmol, 33%).

b) To a stirred solution of the 3-(4-(4-chloro-3-((R)-1-(2,4-dichlorophenyl)ethylamino)phenyl)piperazin-1-yl)cyclohexanecarboxylic acid (0.072 g, 0.14 mmol) and HATU (0.11 g, 0.28 mmol) in anhydrous N,N-dimethylformamide (DMF) (1.0 mL) was added a solution of ammonia (0.5 M in p-dioxane, 0.5 mL, 0.25 mmol). The reaction mixture was heated at 45° C. for 18 h. After cooling to room temperature, the reaction mixture was quenched with deionized water, extracted with diethyl ether. The organic layer was dried (Na$_2$SO$_4$), filtered, and concentrated in vacuo. The crude product was purified by flash chromatography (SiO$_2$, 10-50% ethyl acetate in hexanes) to afford the title compound as a white solid (0.014 g, 0.028 mmol, 20%). $^1$H NMR (400 MHz, CDCl$_3$) δ 7.37-7.32 (m, 2H), 7.16 (dd, J=2.4, 8.4 Hz, 1H), 7.07 (d, J=8.4 Hz, 1H), 6.17 (dd, J=2.4, 8.8 Hz, 1H), 5.77 (d, J=4.8 Hz, 1H), 5.43 (br, 1H), 5.29 (br, 1H), 4.93-4.88 (m, 1H), 4.65 (d, J=4.8 Hz, 1H), 3.00-2.93 (m, 3H), 2.65-2.63 (m, 3H), 2.41-2.34 (m, 1H), 2.23-2.17 (m, 1H), 2.11-2.09 (m, 1H), 1.94-1.88 (m, 3H), 1.60 (m, 2H), 1.53 (d, J=6.4 Hz, 3H), 1.46-1.15 (m, 4H); MS: (ES) m/z calculated for C$_{25}$H$_{32}$Cl$_3$N$_4$O [M+H]$^+$ 509.2, found 509.3.

Example 16

Figure 19:
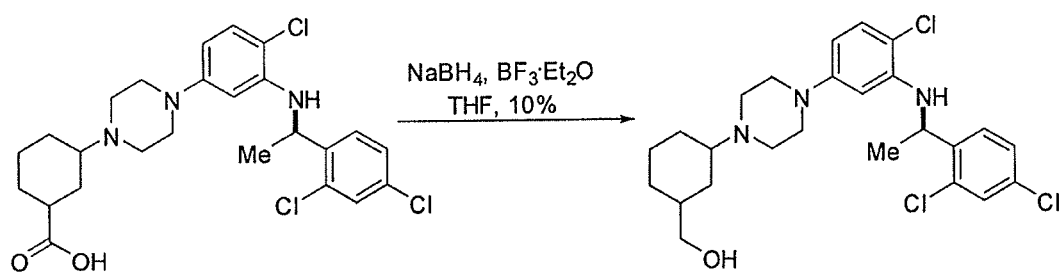
FIG. 19 provides a reaction scheme for the preparation of (3-(4-(4-chloro-3-((R)-1-(2,4-dichlorophenyl)ethylamino)phenyl)piperazin-1-yl)cyclohexyl)methanol (see Example 16).

Synthesis of (3-(4-(4-chloro-3-((R)-1-(2,4-dichlorophenyl)ethylamino)phenyl)piperazin-1-yl)cyclohexyl)methanol (See FIG. 19)

a) To a solution of 3-(4-(4-chloro-3-((R)-1-(2,4-dichlorophenyl)ethylamino)phenyl)piperazin-1-yl)cyclohexanecarboxylic acid (prepared as illustrated in Example 15, 0.077 g, 0.15 mmol) in THF (1 mL) at 0° C. was added sodium borohydride (NaBH$_4$) (0.017 g, 0.5 mmol) and boron trifluoride diethyl etherate (BF$_3$·Et$_2$O) (0.1 mL, 0.8 mmol). The reaction mixture was then stirred at room temperature for 2 h. The reaction was quenched with aqueous saturated sodium bicarbonate and extracted with dichloromethane. The organic layer was dried (Na$_2$SO$_4$), filtered, and concentrated in vacuo. The resulting crude was purified by flash chromatography (SiO$_2$, 10-40% ethyl acetate in hexanes) to afford the desired product as a white solid (0.0074 g, 0.015 mmol, 10%). $^1$H NMR (400 MHz, CDCl$_3$) δ 7.37-7.32 (m, 2H), 7.17 (dd, J=2.0, 8.0 Hz, 1H), 7.06 (d, J=8.8 Hz, 1H), 6.17 (dd, J=2.8, 8.8 Hz, 1H), 5.78 (d, J=2.4 Hz, 1H), 4.90 (dd, J=5.6, 6.4 Hz, 1H), 4.65 (d, J=5.2 Hz, 1H), 3.54 (d, J=7.2 Hz, 2H), 3.03-2.99 (m, 3H), 2.59 (m, 3H), 2.39-2.36 (m, 1H), 2.05-1.95 (m, 1H), 1.75-1.34 (m, 14H); MS: (ES) m/z calculated for C$_{25}$H$_{33}$Cl$_3$N$_3$O [M+H]$^+$ 496.2, found 496.3.

Example 17

Figure 20:
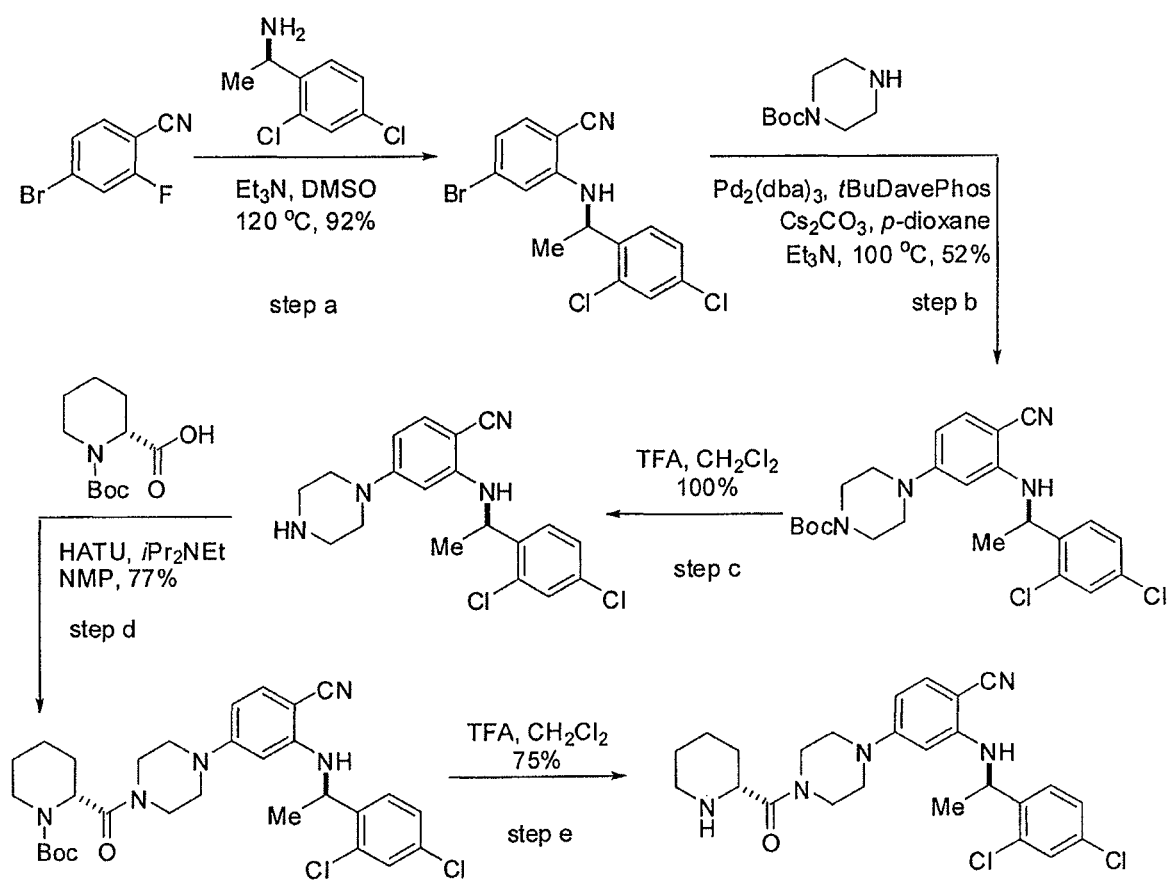
FIG. 20 provides a reaction scheme for the preparation of 2-((R)-1-(2,4-dichlorophenyl)ethylamino)-4-(4-((R)-piperidine-2-carbonyl)piperazin-1-yl)benzonitrile (see Example 17).

Synthesis of 2-((R)-1-(2,4-dichlorophenyl)ethylamino)-4-(4-((R)-piperidine-2-carbonyl)piperazin-1-yl)benzonitrile (See FIG. 20)

a) To a solution of 4-bromo-2-fluoro-benzonitrile (2.0 g, 10.0 mmol) and (1R)-1-(2,4-dichlorophenyl)ethanamine (1.9 g, 10.0 mmol) in dimethyl sulfoxide (DMSO) (4 mL) was added triethylamine (1.45 g, 14.3 mmol). The reaction mixture was heated at 120° C. for 20 h. After cooling to room temperature, the mixture was diluted with deionized water and a brown gummy material was obtained. The aqueous layer was decanted off, and the gum was dissolved in ethyl acetate, washed with deionized water, and brine. The organic layer was dried (Na$_2$SO$_4$), filtered, and concentrated in vacuo. The crude product was used without further purification ((3.4 g, 9.2 mmol, 92%).

b) A mixture of (R)-4-bromo-2-(1-(2,4-dichlorophenyl)ethylamino)benzonitrile (0.51 g, 1.4 mmol), N-t-butyloxycarbonylpiperazine (0.51 g, 2.8 mmol), tBuDavePhos (0.047 g, 0.13 mmol), and Cs$_2$CO$_3$ (1.1 g, 3.5 mmol) in 2:1p-dioxane/triethyl amine (3 mL) was purged with nitrogen for 10 min. Addition of Pd$_2$(dba)$_3$ (0.05 g, 0.05 mmol) was followed, and the mixture was purged with nitrogen for 1 min. The reaction was then heated at 100° C. for 1.5 h. After cooling to room temperature, the mixture was filtered and washed with EtOAc (25 mL). The filtrate was concentrated in vacuo. The resulting crude mixture was purified by flash chromatography (SiO$_2$, 0-20% ethyl acetate in hexanes) to afford the coupled product (0.34 g, 0.72 mmol, 52%).

c) Trifluoroacetic acid (0.5 mL) was added to a solution of (R)-t-butyl 4-(4-cyano-3-(1-(2,4-dichlorophenyl)ethylamino)phenyl)piperazine-1-carboxylate (0.34 g, 0.72 mmol) in dichloromethane (2 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried (Na$_2$SO$_4$), filtered, and concentrated in vacuo. The crude product was used without further purification (0.27 g, 0.72 mmol, 100%).

d) To a stirred solution of the (R)-2-(1-(2,4-dichlorophenyl)ethylamino)-4-(piperazin-1-yl)benzonitrile (0.080 g, 0.21 mmol) and (R)-1-(t-butoxycarbonyl)piperdino-2-carboxylic acid (0.049 g, 0.21 mmol) in 1-methyl pyrrolidinone (NMP) (1.0 mL) was added HATU (0.085 g, 0.22 mmol) and iPr$_2$NEt (0.055 g, 0.43 mmol). The reaction mixture was stirred at room temperature for 2 h, and quenched with deionized water. The aqueous layer was extracted with diethyl ether (2×10 mL). The organic layer was dried (Na$_2$SO$_4$), filtered, and concentrated in vacuo. The crude product was purified by flash chromatography (SiO$_2$, 0-25% ethyl acetate in hexanes) to afford the desired product (0.095 g, 0.16 mmol, 77%).

e) Trifluoroacetic acid (0.3 mL) was added to a solution of (R)-t-butyl 2-(4-(4-cyano-3-((R)-1-(2,4-dichlorophenyl)ethylamino)phenyl)piperazine-1-carbonyl)piperidine-1-carboxylate (0.095 g, 0.16 mmol) in dichloromethane (1 mL) at room temperature, and the solution was stirred for 1 h. Excess solvent was removed in vacuo, and the residue was diluted with dichloromethane. The organic layer was neutralized with aqueous saturated sodium bicarbonate solution, and the aqueous layer was further extracted with dichloromethane. The combined organic layers were dried (Na$_2$SO$_4$), filtered, and concentrated in vacuo to give the title compound as a white solid (0.060 g, 0.12 mmol, 75%). $^1$H NMR (400 MHz, DMSO-d$_6$) δ 9.0 (br, 1H), 8.62-8.52 (m, 1H), 7.62-7.50 (m, 2H), 7.37 (dd, J=2.2, 8.4 Hz, 1H), 7.05 (d, J=8.8 Hz, 1H), 6.19 (dd, J=2.5, 8.8 Hz, 1H), 5.82 (d, J=2.6 Hz, 1H), 5.68 (br, 1H), 4.86 (br, 1H), 3.70-2.80 (m, 9H), 1.98-1.92 (m, 1H), 1.78-1.58 (m, 4H), 1.50-1.40 (m, 5H); MS: (ES) m/z calculated for C$_{25}$H$_{30}$Cl$_2$N$_5$O [M+H]$^+$ 486.2, found 486.

Example 18

Figure 21:
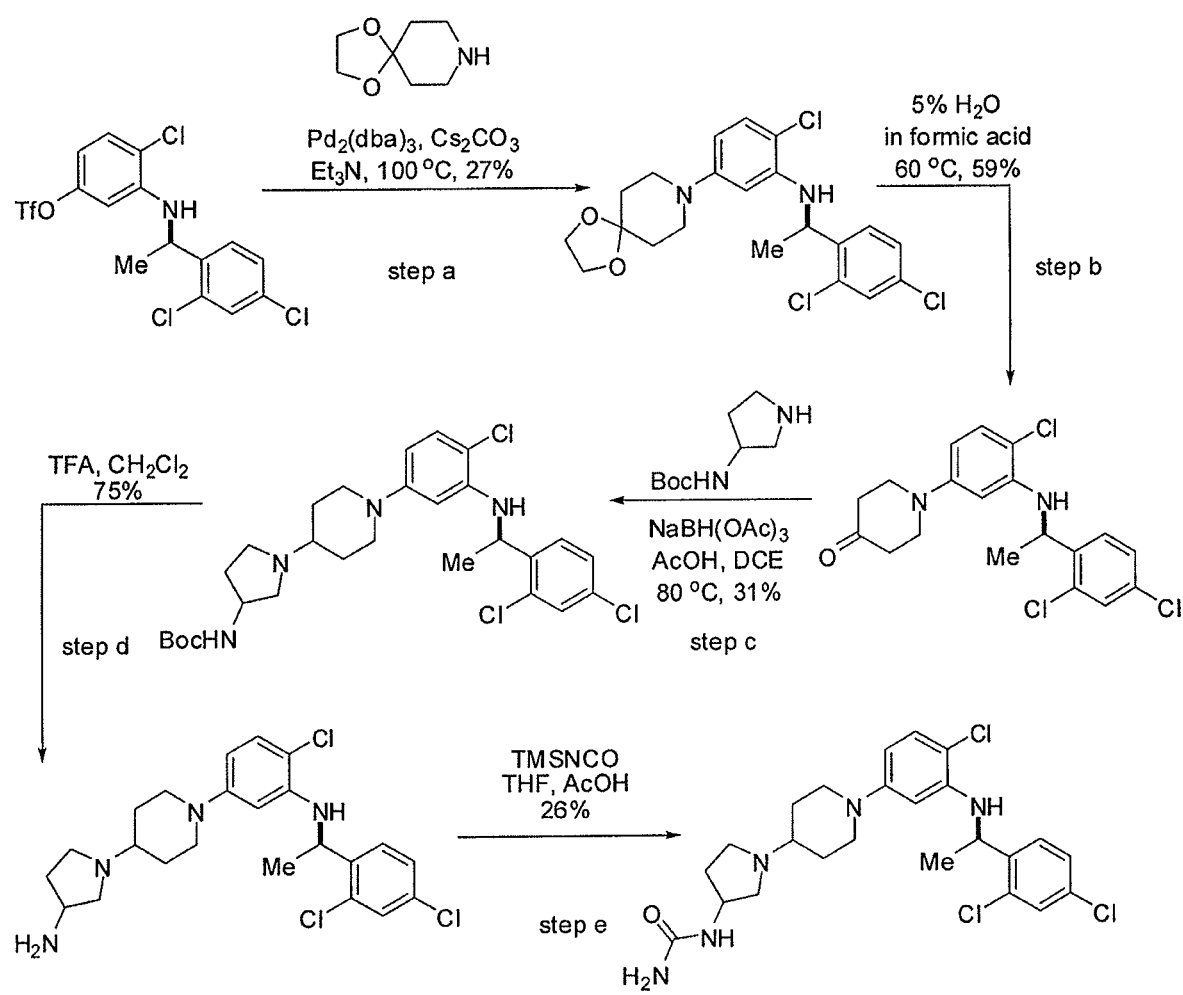
FIG. 21 provides a reaction scheme for the preparation of 1-(1-(1-(4-chloro-3-((R)-1-(2,4-dichlorophenyl)ethylamino)phenyl)piperidin-4-yl)pyrrolidin-3-yl)urea (see Example 18).
Figure 22D:
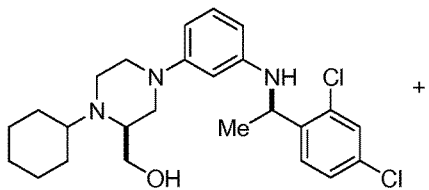
FIGS. 22A-22S provide structure and activity for representative compounds provided herein (see also Biological Example 1).
Figure 22D:
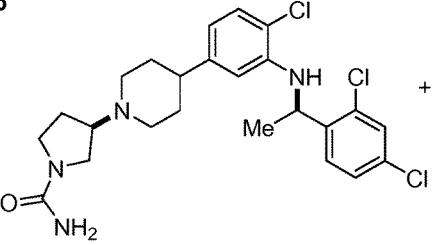
Figure 22D:
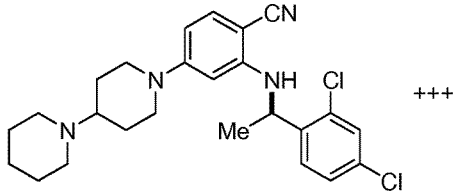
Figure 22D:
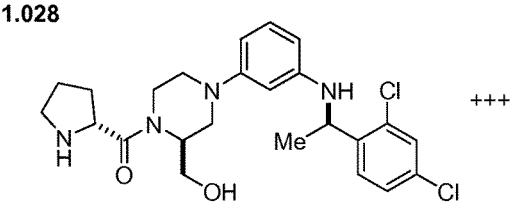
Figure 22D:
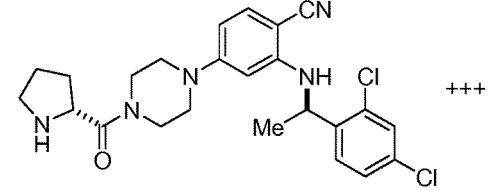
Figure 22D:
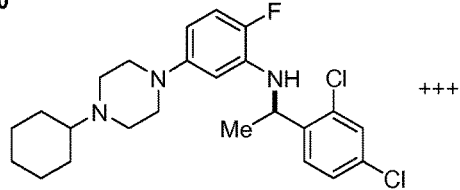
Figure 22D:
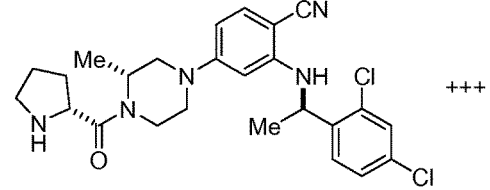
Figure 22D:
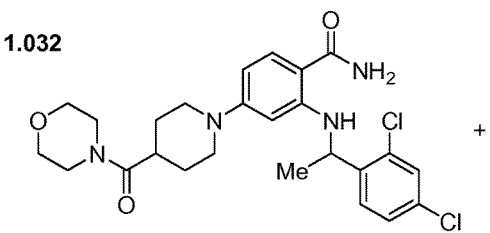
Figure 22E:
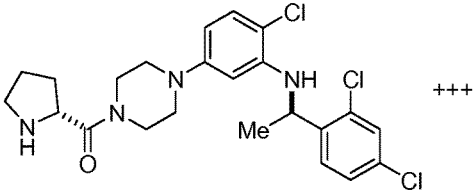
Figure 22E:
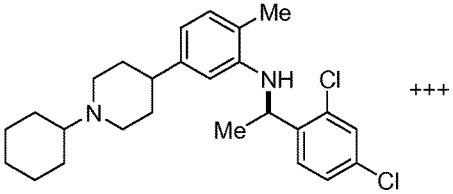
Figure 22E:
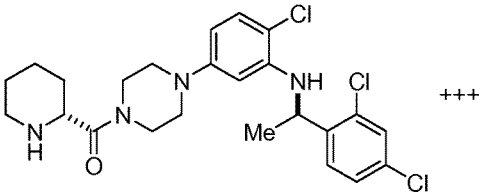
Figure 22E:
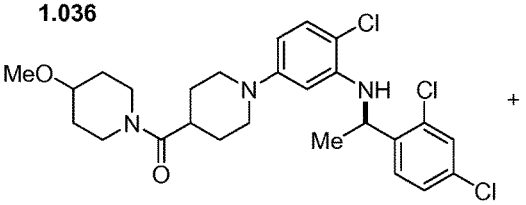
Figure 22E:
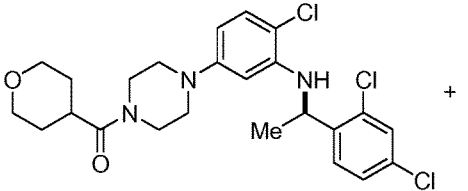
Figure 22E:
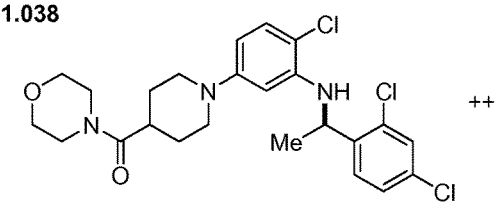
Figure 22E:
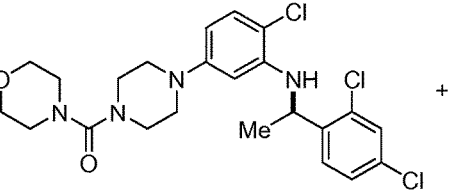
Figure 22E:
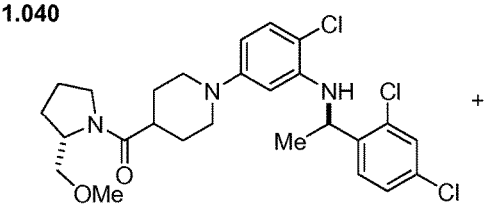
Figure 22H:
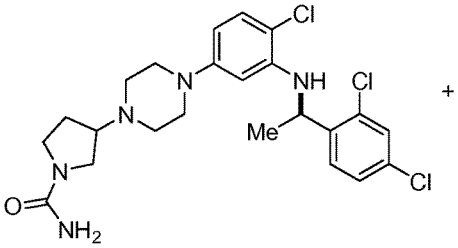
Figure 22H:
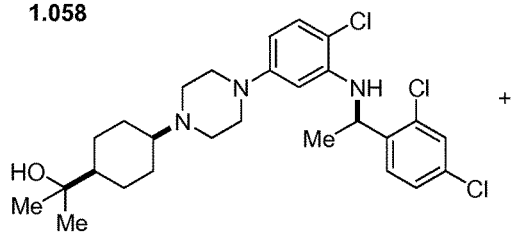
Figure 22H:
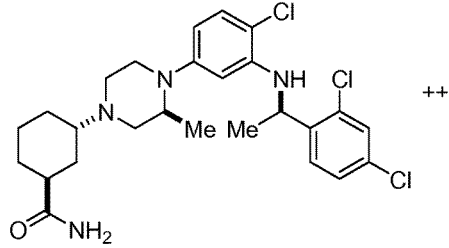
Figure 22H:
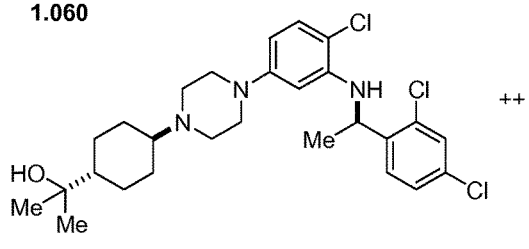
Figure 22H:
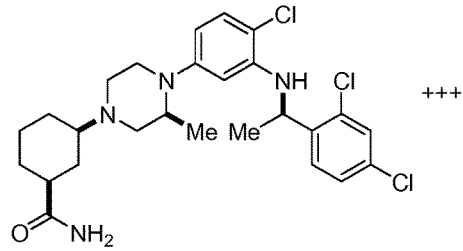
Figure 22H:
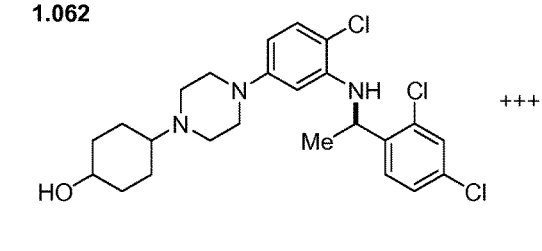
Figure 22H:
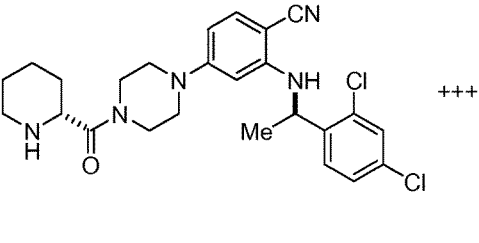
Figure 22H:
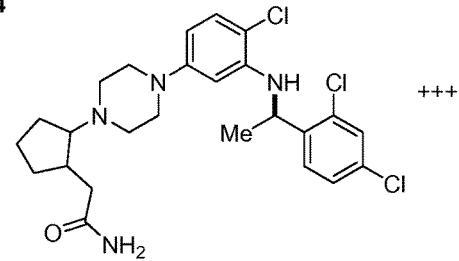
Figure 22K:
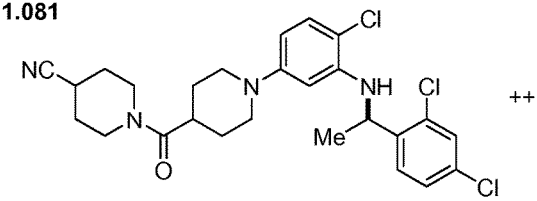
Figure 22K:
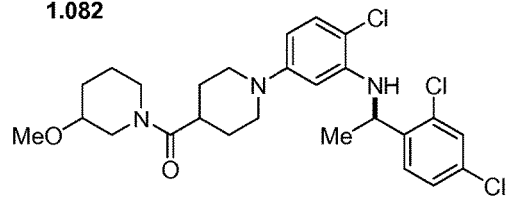
Figure 22K:
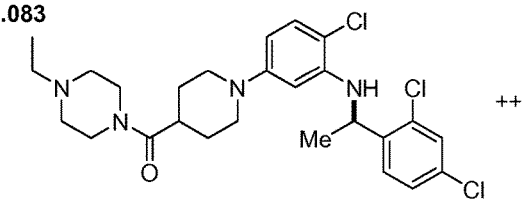
Figure 22K:
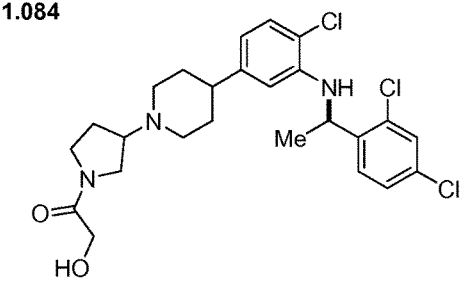
Figure 22K:
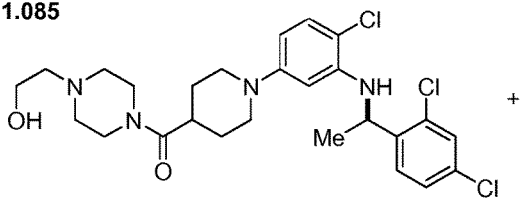
Figure 22K:
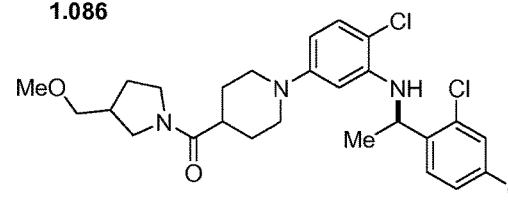
Figure 22K:
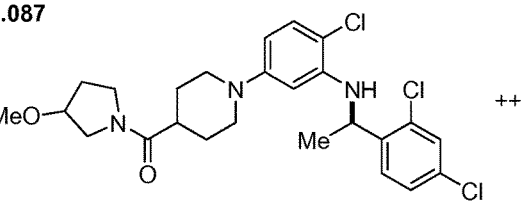
Figure 22K:
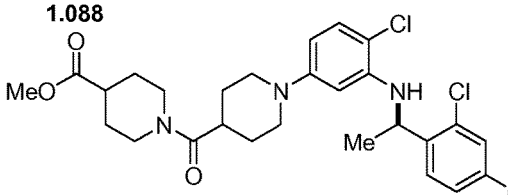
Figure 22Q:
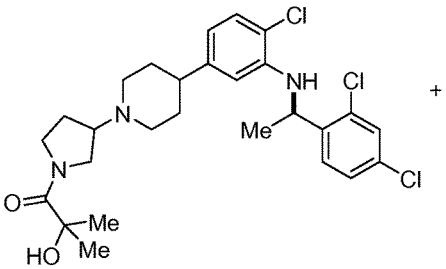
Figure 22Q:
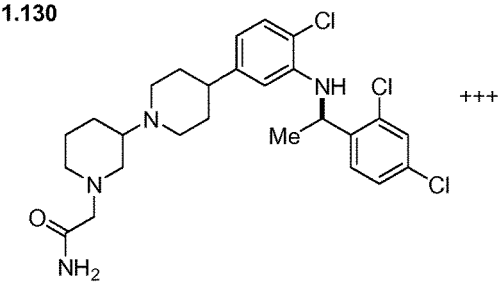
Figure 22Q:
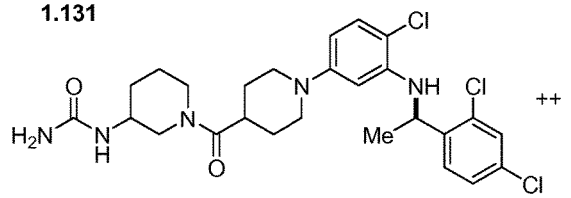
Figure 22Q:
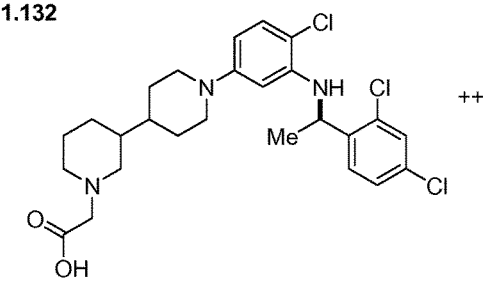
Figure 22Q:
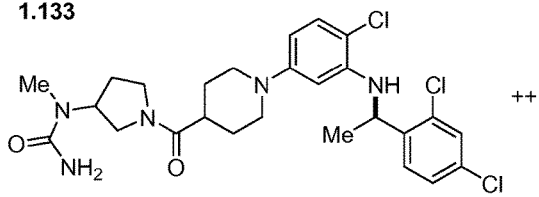
Figure 22Q:
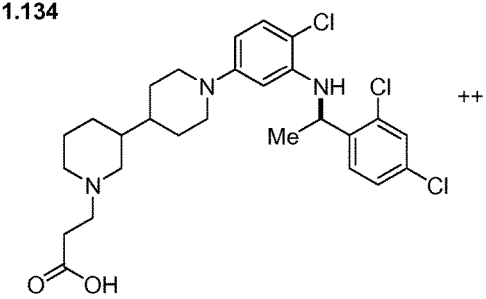
Figure 22Q:
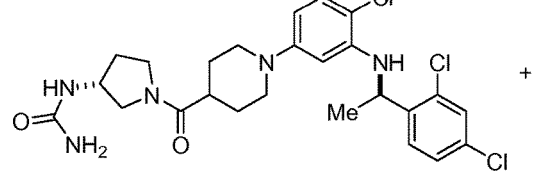
Figure 22Q:
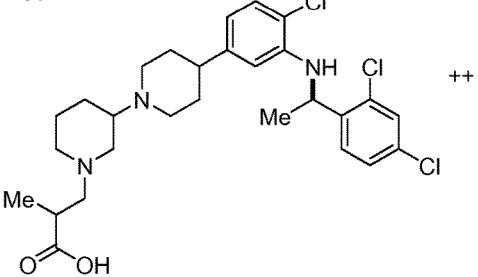
Figure 22S:
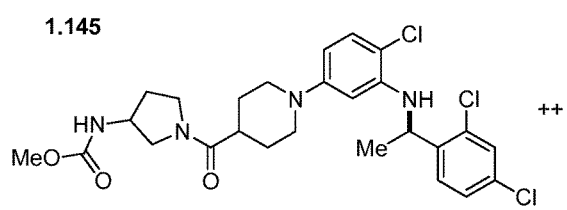

Synthesis of 1-(1-(1-(4-chloro-3-((R)-1-(2,4-dichlorophenyl)ethylamino)phenyl)piperidin-4-yl)pyrrolidin-3-yl)urea (See FIG. 21)

a) A mixture of (R)-4-chloro-3-(1-(2,4-dichlorophenyl)ethylamino)phenyl trifluoromethanesulfonate (Example 2 step d, 5.0 g, 11.1 mmol), 4-piperidone ethylene acetal (4.0 g, 27.9 mmol), tBuDavePhos (0.23 g, 0.66 mmol), and Cs$_2$CO$_3$ (7.2 g, 22.2 mmol) in triethylamine (32 mL) was purged with nitrogen for 5 min. Addition of Pd$_2$(dba)$_3$ (0.31 g, 0.33 mmol) was followed, and the mixture was purged with nitrogen for 1 min. The reaction was then heated at 100° C. for 18 h. After cooling to room temperature, the mixture was filtered and washed with EtOAc (50 mL). The filtrate was concentrated in vacuo, and the resulting crude mixture was purified by flash chromatography (SiO$_2$, 0-20% ethyl acetate in hexanes) to afford the coupled product as a viscous oil (1.3 g, 3.0 mmol, 27%).

b) To a solution of 2-chloro-N—((R)-1-(2,4-dichlorophenyl)ethyl)-5-(1,4-dioxa-8-azaspiro[4.5]decan-8-yl)aniline (1.3 g, 3.0 mmol) in 5% deionized water in formic acid (5 mL) was heated at 60° C. for 18 h. The mixture was concentrated in vacuo, and the residue was partitioned in EtOAc and deionized water. The organic layer was dried (Na$_2$SO$_4$), filtered, and concentrated in vacuo. The crude mixture was purified by flash chromatography (SiO$_2$, 0-60% ethyl acetate in hexanes) to afford the desired product (0.7 g, 1.76 mmol, 59%).

c) To a stirred solution of (R)-1-(4-chloro-3-(1-(2,4-dichlorophenyl)ethylamino)phenyl)piperidin-4-one (0.13 g, 0.32 mmol) and 3-(t-butoxycarbonylamino)pyrrolidine (0.24 g, 1.3 mmol) in dichloroethane (DCE) (2 mL) was added NaBH(OAc)$_3$ (0.094 g, 0.44 mmol). The reaction mixture was heated at 80° C. for 4 h. The reaction mixture was quenched with aqueous saturated sodium bicarbonate and extracted with dichloromethane. The organic layer was dried (Na$_2$SO$_4$), filtered, and concentrated in vacuo. The resulting crude was purified by flash chromatography (SiO$_2$, 1-7% methanol in dichloromethane) to give t-butyl 1-(1-(4-chloro-3-((R)-1-(2,4-dichlorophenyl)ethylamino)phenyl)piperidin-4-yl)pyrrolidin-3-ylcarbamate (0.092 g, 0.16 mmol, 31%).

d) Trifluoroacetic acid (0.5 mL) was added to a solution of t-butyl 1-(1-(4-chloro-3-((R)-1-(2,4-dichlorophenyl)ethylamino)phenyl)piperidin-4-yl)pyrrolidin-3-ylcarbamate (0.092 g, 0.16 mmol) in dichloromethane (1.5 mL) at room temperature, and the solution was stirred for 30 min. The mixture was diluted with dichloromethane, and neutralized with aqueous saturated sodium bicarbonate solution. The aqueous layer was extracted with dichloromethane, and the organic layer was dried (Na$_2$SO$_4$), filtered, and concentrated in vacuo. The crude product was used without further purification (0.056 g, 0.12 mmol, 75%).

e) To a stirred solution of 1-(1-(4-chloro-3-((R)-1-(2,4-dichlorophenyl)ethylamino)phenyl)piperidin-4-yl)pyrrolidin-3-amine (0.056 g, 0.12 mmol) in THF (1 mL) and acetic acid (1 drop) was added a solution of (trimethylsilyl)isocyanate (0.015 g, 0.13 mmol) in THF (0.5 mL). The reaction mixture was stirred at room temperature for 30 min. The reaction mixture was quenched with diluted with aqueous saturated sodium bicarbonate and extracted with EtOAc. The organic layer was dried (Na$_2$SO$_4$), filtered, and concentrated in vacuo. The resulting crude was purified by flash chromatography (SiO$_2$, 2-10% methanol in dichloromethane) to afford the desired product as a white solid (0.016 g, 0.031 mmol, 26%). $^1$H NMR (400 MHz, CDCl$_3$) δ 7.36-7.32 (m, 2H), 7.16 (dd, J=2.2, 8.4 Hz, 1H), 7.04 (d, J=8.6 Hz, 1H), 6.82 (br, 1H), 6.16 (dd, J=2.5, 8.8 Hz, 1H), 5.77 (br, 1H), 5.23 (br, 1H), 4.87 (q, J=6.6 Hz, 1H), 4.64 (d, J=5.2 Hz, 1H), 3.44-3.37 (m, 2H), 3.08-2.82 (m, 3H), 2.69-2.40 (m, 4H), 2.25-1.85 (m, 6H), 1.60-1.42 (m, 5H); MS: (ES) m/z calculated for C$_{24}$H$_{31}$C$_{13}$N$_5$O [M+H]$^+$ 510.2, found 510.

Biological Examples

Biological Example 1

Ligand Binding Assay

Ligand binding assay was used to determine the ability of potential CCR(4) antagonists to block the interaction between CCR(4) and its ligand CCL17 (TARC). CEM cells (ATCC, VA) which naturally express the CCR(4) receptor, were centrifuged and resuspended in assay buffer (20 mM HEPES pH 7.1, 140 mM NaCl, 1 mM CaCl2, 5 mM MgCl2, 0.1% sodium azide and with 0.1% bovine serum albumin) to a concentration of 5×10^5 cells/mL. Binding assays were set up as follows. First, 0.1 mL of cells (5×10$^4$ cells/well) was added to the assay plates containing the compounds, giving a final concentration of ~2-10 uM each compound for screening (or part of a dose response for compound IC50 determinations). Then 0.1 mL of 125I labeled TARC (obtained from PerkinElmer; Waltham, MA) diluted in assay buffer to a final concentration of ~50 pM, yielding ~30,000 cpm per well, was added, the plates sealed and incubated for approximately 3 hours at 25° C. on a shaker platform. Reactions were aspirated onto GF/B glass filters pre-soaked in 0.3% polyethyleneimine (PEI) solution, on a vacuum cell harvester (Packard Instruments; Meriden, CT). Scintillation fluid (50 uL; Microscint 20, Packard Instruments) was added to each well, the plates were sealed and radioactivity measured in a Top Count scintillation counter (Packard Instruments). Control wells containing either diluent only (for total counts) or 20 uM compound were used to calculate the percent of total inhibition for compound. The computer program Prism from GraphPad, Inc. (San Diego, Ca) was used to calculate IC50 values. IC50 values are those concentrations required to reduce the binding of labeled TARC to the receptor by 50%. Compounds in FIG. 22 having an IC50 value in the binding assay of less than 100 nM are labeled (+++); from 100-500 nM are labeled (++); and above 500 nM are labeled (+).

Biological Example 2

A serum chemotaxis assay was used to determine the efficacy of potential receptor antagonists at blocking the migration mediated through chemokine receptors, such as CCR(4). This assay was routinely performed using the ChemoTX® microchamber system with a 5-μm pore-sized polycarbonate membrane. To begin such an assay, chemokine-receptor expressing cells (such as CEM cells for the CCR(4) assay) were collected by centrifugation at 400×g at room temperature, then suspended at 50 million/ml in human serum. The compound being tested or an equivalent volume of its solvent (DMSO) was then added to the cell/serum mixture at a final DMSO concentration of 0.25% (v/v). Separately, recombinant human CCL22 (MDC) was diluted with chemotaxis buffer (HBSS+0.1% BSA), generally spanning a range from 0.01 nM to 500 nM, after which 29 μl of diluted chemokine was placed in the lower wells of the ChemoTX® plate. The 5-μm (pore size) polycarbonate membrane was placed onto the plate, and 20 μL of the cell/compound mixture was transferred onto each well of the membrane. The plates were incubated at 37° C. for 90 minutes, after which the polycarbonate membranes were removed and 5 μl of the DNA-intercalating agent CyQUANT (Invitrogen, Carlsbad, CA) was added to the lower wells. The amount of fluorescence, corresponding to the number of migrated cells, was measured using a Spectrafluor Plus plate reader (TECAN, San Jose, CA).

Biological Example 3

Compounds of the invention were assessed in the murine model of dermal delayed type hypersensitivity induced by oxazolone. Briefly, 8-10 week old BALB/c mice were sensitized topically with a 1% solution of oxazolone dissolved in ethanol on their shaved abdomens on day 0. On day 6 post sensitization mice were dosed orally with either vehicle or increasing doses of compound 1.127 of the invention immediately prior to and 4 hours following a topical challenge with a 0.5% solution of oxazolone in ethanol on the right ear. The following day (day 7), ear thicknesses were measured using caliper measurements. Animals treated with compound had significantly reduced ear swelling compared to vehicle treated controls indicating a compound mediated decrease in oxazolone induced dermal hypersensitivity.

Biological Example 4

CCR(4)Compounds of the invention were assessed in the murine model of allergic asthma. Asthma was induced in 8-10 week old BALB/c mice by sensitizing mice with OVA in Alum adjuvant on days 0 and 10. On day 20 mice were challenged with OVA in PBS intranasally to elicit airway inflammation. Groups of mice were either treated with vehicle, or increasing doses of compound 1.127 of the invention starting on day 20 and lasting until day 23. Animals were subsequently analyzed at day 23 after the intranasal OVA challenge for cellular infiltrates in bronchoalveolar lavage (BAL). Mice treated with a compound of the invention displayed significantly reduced BAL leukocyte numbers relative to vehicle treated mice at all doses tested.

Biological Example 5

This example describes a procedure to evaluate the efficacy of CCR(4) antagonists for treatment of rheumatoid arthritis. An animal model of rheumatoid arthritis can be induced in rodents by injecting them with type II collagen in selected adjuvants. Three series of rodent groups consisting of 15 genetically-susceptible mice or rats per group are injected sub-cutaneously or intra-dermally with type II collagen emulsified in Complete Freund's Adjuvant at days 0 and 21. One series of rodents additionally receives PBS and Tween 0.5% i.p. at the initial sensitization, and at different dosing schedules thereafter. A second series consists of groups of rodents receiving different doses of the CCR(4) antagonist given either intra-peritoneally, intra-venously, sub-cutaneously, intramuscularly, orally, or via any other mode of administration at the initial sensitization, and at different dosing schedules thereafter. A third series of rodents, serving as positive control, consists of groups treated with either mouse IL-10 i.p., or anti-TNF antibodies i.p. at the initial sensitization, and at different dosing schedules thereafter. Animals are monitored from weeks 3 till 8 for the development of swollen joints or paws, and graded on a standard disease severity scale. Disease severity is confirmed by histological analysis of joints.

Biological Example 6

This example describes a procedure to evaluate efficacy of CCR(4) antagonists for treatment of Systemic Lupus Erythematosus (SLE). Female NZB/W FI mice spontaneously develop an SLE-like pathology commencing at 6 months of age that is characterized by proteinuria, serum autoantibodies, glomerulonephritis, and eventually death. Three series of NZB/W FI mouse groups comprising 20 mice per group are tested for efficacy of CCR(4) antagonist as follows: One series of mice additionally receives phosphate buffered saline (PBS) and Tween 0.5% i.p. soon after weaning, and thereafter at varying dosing schedules. A second series consists of groups of mice receiving different doses of the CCR(4) antagonist given either intra-peritoneally, intra-venously, sub-cutaneously, intramuscularly, orally, or via any other mode of administration soon after weaning, and thereafter at varying dosing schedules. A third series of mice, serving as positive control, consists of groups treated with anti-IL10 antibodies given soon after weaning, and thereafter at varying dosing schedules. Disease development is monitored in terms of eventual mortality, kidney histology, serum autoantibody levels, and proteinuria.

Biological Example 7

This example describes a procedure to evaluate efficacy of CCR(4) antagonists for treatment of malignancy. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR(4) antagonist efficacy as follows: One series of mice additionally receives PBS and Tween 0.5% i.p. soon after tumor transplant, and thereafter at varying dosing schedules. A second series consists of groups of mice receiving different doses of the CCR(4) antagonist given either intra-peritoneally, intra-venously, sub-cutaneously, intramuscularly, orally, or via any other mode of administration soon after tumor transplant, and thereafter at varying dosing schedules. A third series of mice, serving as positive control, consists of groups treated with either anti-IL4 antibodies, anti-IFNg antibodies, IL4, or TNF, given i.p. soon after tumor transplant, and thereafter at varying dosing schedules. Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours.

Biological Example 8

This example describes procedures to evaluate the efficacy of CCR(4) antagonists in psoriasis. A rodent model of psoriasis can be obtained by intra-venously transferring a population of purified T cells (designated CD45Rbhi T cells) obtained from the spleens of BALB/c mice into immunodeficient recipient CB.17 scid/scid mice. Mice develop signs of redness, swelling, and skin lesions resembling those of human psoriasis in their ear, feet and tail by 8 weeks after transfer. Three series of mouse groups, comprising 10-15 CB.17 scid/scid mice per group, are injected with purified CD45Rbhi T cells. One series of mice additionally receives phosphate buffered saline (PBS) and Tween 0.5% i.p. at the initial cell transfer, and at different dosing schedules thereafter. A second series consists of groups of mice receiving different doses of the CCR(4) antagonist given either intraperitoneally, intra-venously, sub-cutaneously, intra-muscularly, orally, or via any other mode of administration at the initial cell transfer, and at different dosing schedules thereafter. A third series of mice, serving as positive control, consists of groups treated with antibodies to either IL-12, IL-4, IFNg, or TNF, or with cytokine IL-10 at the initial cell transfer, and at different dosing schedules thereafter. Animals are monitored for development of psoriatic-like lesions for 3 months after cell transfer.

Biological Example 9

This example describes a procedure to evaluate the efficacy of CCR(4) antagonists in Inflammatory Bowel Disease (IBD). Several mouse models of IBD (including Crohn's Disease and Ulcerative Colitis) have been developed. Some of these are spontaneous models occurring in genetically engineered transgenic mice that have been depleted of certain cytokine genes (e.g. IL-I0, or IL-2). Another mouse model of IBD is obtained by transferring highly purified populations of CD4+ T lymphocytes bearing a particular surface marker phenotype (namely CD45 RB hi) into SCID mice. Three series of mouse groups from anyone of these models can be used to evaluate CCR(4) antagonist efficacy as follows. One group of mice additionally receives PBS and Tween 0.5% i.p. soon after weaning in the case of the spontaneous models in transgenic mice, or at time of cell transfer into SCID mice and varying dosings thereafter for the cell transfer model. A second series consists of groups of mice receiving different doses of the CCR(4) antagonist given either intraperitoneally, intra-venously, sub-cutaneously, intra-muscularly, orally, or via any other mode of administration soon after weaning in the case of the spontaneous models in transgenic mice, or at time of cell transfer into SCID mice and varying dosings thereafter for the cell transfer model. A third series of mice, serving as positive control, consists of groups treated with antibodies to either IFNg, or TNF, or with cytokine IL-10 soon after weaning in the case of the spontaneous models in transgenic mice, or at time of cell transfer into SCID mice and varying dosings thereafter for the cell transfer model. Mice are evaluated for 6-8 weeks for disease development, monitored initially via weight loss and/or prolapsed rectum, and eventually by histological evaluation of the animals colon and intestinal tract.

Biological Example 10

The mouse RENCA tumor model accurately mimics the progression of human adult renal cell carcinoma specifically with reference to spontaneous metastasis to lungs and serves as a model for solid tumors. Balb/c 6-8 week old female mice are inoculated with approximately 5e5 RENCA cells (mouse renal adenocarcinoma; ATCC cat #CRL-2947) under the kidney capsule and kidney tumor growth is observed over 22 days, with lung metastasis observed as early as day 15. Animals are dosed with either vehicle or a compound of the invention eg daily subcutaneously, from the time of tumor implantation to monitor effects on primary growth, or at a later time (eg day 7) to monitor the compound effect on metastasis. Primary tumor areas are measured twice a week using mechanical calipers. Tumor volumes are calculated by the formula v=pab2/6, where a is the longest diameter and b is the next longest diameter perpendicular to a. A reduction in tumor volume or incidence of metastasis indicates efficacy of compound in this indication.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A pharmaceutical composition comprising a compound of formula (Ic)

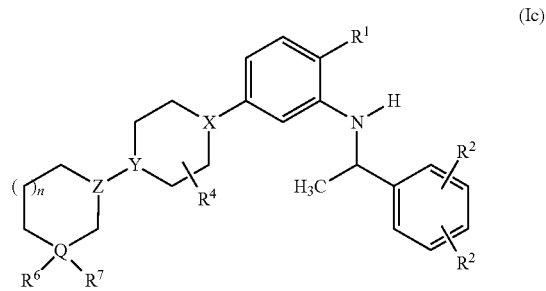

or a pharmaceutically acceptable salt thereof and a pharmaceutically acceptable excipient,
wherein
X and Y are each N;
Z is CH;
Q is CH or N;
$R^1$ is selected from hydrogen, $C_{1-8}$ alkyl, $C_{1-8}$ haloalkyl, and halogen;
each $R^2$ is a member selected from the group consisting of $C_{1-8}$ alkyl, $C_{1-8}$ haloalkyl, halogen and —CN;
$R^4$ is hydrogen or methyl;
$R^6$ is absent or is a member selected from the group consisting of H, —OH, $C_{1-8}$ alkyl, $C_{1-8}$ hydroxyalkyl, $C_{1-4}$ alkoxy-$C_{1-4}$ alkyl, —C(O)NR$^a$R$^b$, —CO$_2$H, —C(O)OR$^a$, —C(O)R$^a$, and —SO$_2$R$^a$;

R$^7$ is absent or is selected from the group consisting of H, $C_{1-8}$ alkyl and $C_{1-8}$ haloalkyl;

each R$^a$ and R$^b$ are independently selected from the group consisting of hydrogen, $C_{1-8}$ alkyl, $C_{1-8}$ hydroxyalkyl, $C_{1-8}$ haloalkyl, and $C_{1-8}$ alkoxy; and the subscript n is 1.

2. The pharmaceutical composition of claim 1, where in the compound of Formula (Ic) is selected from the group consisting of

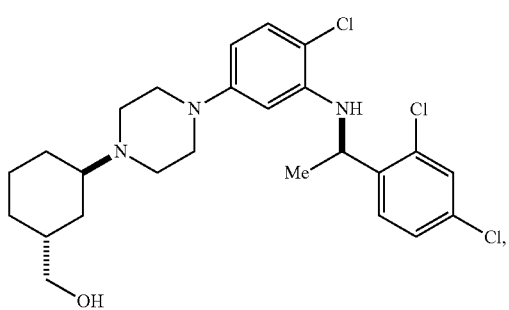

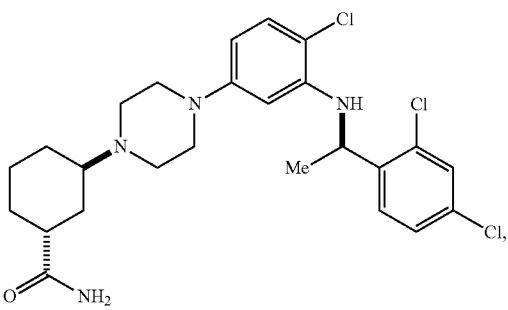

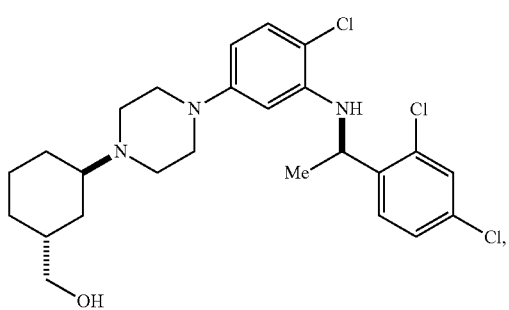

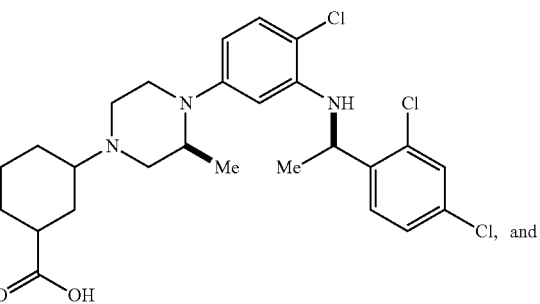

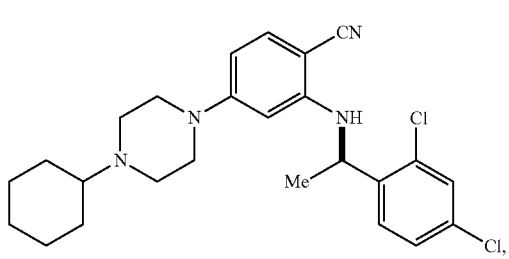

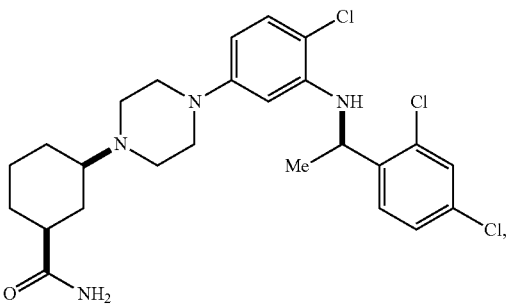

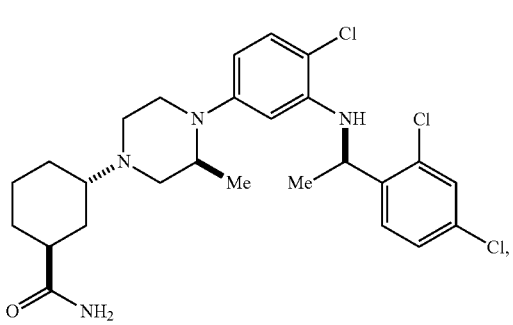

or a pharmaceutically acceptable salt thereof.

3. The pharmaceutical composition of claim 1, where in the compound of Formula (Ic) is

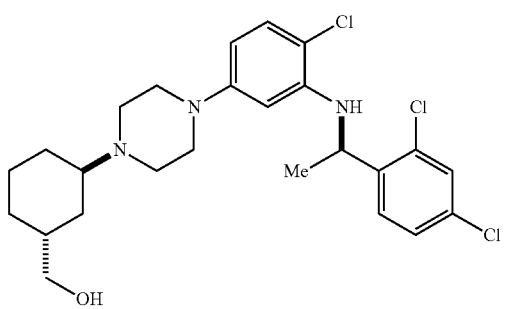

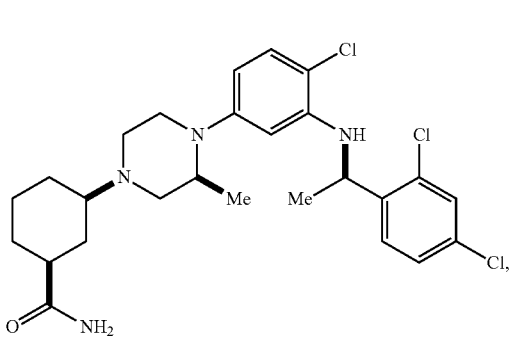

or a pharmaceutically acceptable salt thereof.

4. The pharmaceutical composition of claim 1, where in the compound of Formula (Ic) is

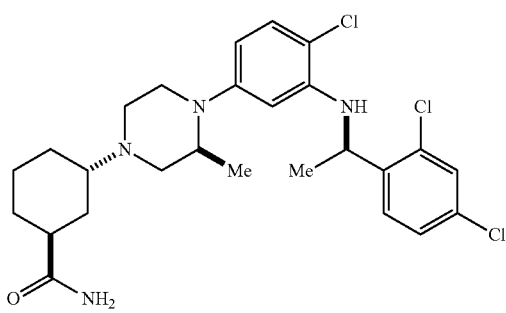

or a pharmaceutically acceptable salt thereof.

5. The pharmaceutical composition of claim 1, where in the compound of Formula (Ic) is

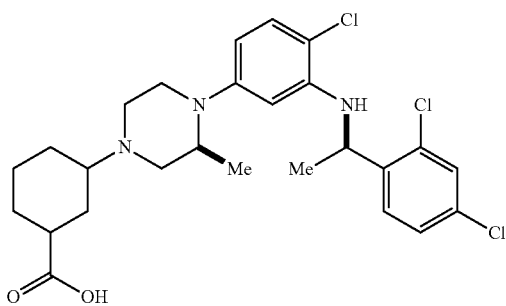

or a pharmaceutically acceptable salt thereof.

6. A method of assaying a small organic molecule for CCR(4) antagonistic activity, said method comprising
   (a) contacting the small organic molecule with cells expressing CCR(4) and a radioactive CCR(4) ligand to form a reaction mixture;
   (b) aspirating the reaction mixture onto a polyethyleneimine-treated GF/B glass filter;
   (c) measuring the amount radioactivity remaining on the GF/B glass filter,
   wherein said method comprises performing steps (a)-(c) with a positive control sample having a formula selected from the group consisting of formula (Ie):

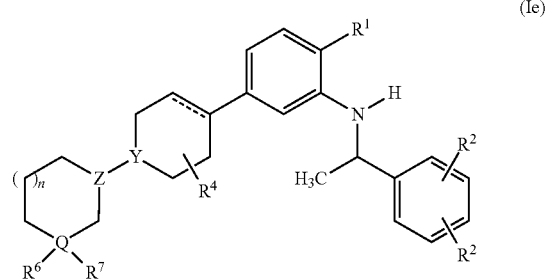

or a pharmaceutically acceptable salt thereof and a pharmaceutically acceptable excipient, wherein
   the bond represented by ═════ in the ring comprising Y is a single bond or a double bond;
   $R^1$ is a member selected from the group consisting of hydrogen, $C_{1-8}$ alkyl, $C_{1-8}$ haloalkyl, $C_{1-8}$ hydroxyalkyl, $C_{3-8}$ cycloalkyl, halogen, —CN, —SO$_2$Me and —C(O)NH$_2$;

each $R^2$ is a member selected from the group consisting of $C_{1-8}$ alkyl, $C_{1-8}$ haloalkyl, halogen, —CN and $C_{1-8}$ alkoxy;
$R^4$ is a member selected from the group consisting of hydrogen, $C_{1-8}$ alkyl, $C_{1-8}$ haloalkyl and $C_{1-8}$ hydroxyalkyl;
the subscripts n is independently an integer from 0 to 3;
Q is a member selected from the group consisting of C and N;
Y and Z are independently selected from the group consisting of CH and N;
$R^6$ is selected from the group consisting of H, —OH, $C_{1-8}$ alkyl, $C_{1-8}$ hydroxyalkyl, $C_{1-4}$ alkoxy-$C_{1-4}$ alkyl, —C(O)NR$^a$R$^b$, $C_{1-8}$ alkylene-C(O)NR$^a$R$^b$, —NH—$C_{1-4}$ alkylene-C(O)NR$^a$R$^b$, —C(O)—$C_{1-4}$ alkylene-NR$^a$R$^b$, —CO$_2$H, $C_{1-8}$ alkylene-CO$_2$H, —N(R$^a$)C(O)NR$^a$R$^b$, $C_{1-8}$ alkylene N(R$^a$)C(O)NR$^a$R$^b$, —NR$^a$R$^b$, $C_{1-8}$ alkylene-NR$^a$R$^b$, $C_{1-8}$ alkoxy, —C(O)OR$^a$, $C_{1-8}$ alkylene-C(O)OR$^a$, —CN, —C(O)R$^a$, —SO$_2$R$^a$ and —N(R$^a$)C(O)R$^b$;
wherein
   each R$^a$ and R$^b$ are independently selected from the group consisting of hydrogen, $C_{1-8}$ alkyl, $C_{1-8}$ hydroxyalkyl, $C_{1-8}$ haloalkyl, and $C_{1-8}$ alkoxy; and
$R^7$ is absent or is selected from the group consisting of H, $C_{1-8}$ alkyl and $C_{1-8}$ haloalkyl.

7. The method of claim 6, wherein said cells expressing CCR(4) are CEM cells or isolated human monocytes.

8. The method of claim 6, wherein said radioactive CCR(4) ligand is CCL17.

9. The method of claim 6, wherein step (a) further comprises a binding buffer.

10. The method of claim 9, wherein the binding buffer comprises 25 mM HEPES, 140 mM NaCl, 1 mM CaCl$_2$, 5 mM MgCl$_2$, and 0.1% bovine serum albumin, at pH 7.1.

11. The method of claim 6, wherein said measuring comprises adding scintillation fluid to the aspirated GF/C glass filter.

12. The method of claim 6, wherein n is 1, and $R^4$ is hydrogen or methyl.

13. The method of claim 6, wherein the compounds of formula (Ie) has formula (If):

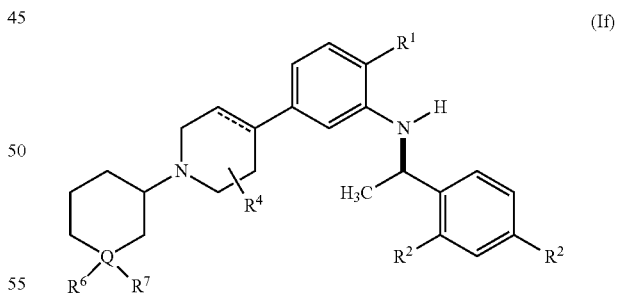

wherein each $R^2$ is a member selected from the group consisting of $C_{1-8}$ alkyl, $C_{1-8}$ haloalkyl, halogen and —CN.

14. The method of claim 6, wherein the ring having Z as a ring vertex is selected from the group consisting of pyrrolidine and piperidine.

15. The method of claim 6, wherein the ring having Z as a ring vertex is selected from the group consisting of pyrrolidin-2-yl and piperidin-2-yl, and at least one of $R^6$ and IC is other than hydrogen.

* * * * *